(12) United States Patent
Popovici et al.

(10) Patent No.: US 11,241,226 B2
(45) Date of Patent: Feb. 8, 2022

(54) DEVICES AND METHODS FOR ADVANCING KNOTS

(71) Applicant: Anchor Orthopedics XT Inc., Mississauga (CA)

(72) Inventors: Ilinca Popovici, Toronto (CA); Neil Godara, Milton (CA); Robert Harrison, Milton (CA); Jeffery Arnett, Gilbert, AZ (US)

(73) Assignee: Anchor Orthopedics XT Inc., Mississauga (CA)

( * ) Notice: Subject to any disclaimer, the term of this patent is extended or adjusted under 35 U.S.C. 154(b) by 666 days.

(21) Appl. No.: 15/108,974

(22) PCT Filed: Jul. 9, 2014

(86) PCT No.: PCT/IB2014/062988
§ 371 (c)(1),
(2) Date: Jun. 29, 2016

(87) PCT Pub. No.: WO2015/101846
PCT Pub. Date: Jul. 9, 2015

(65) Prior Publication Data
US 2016/0317144 A1    Nov. 3, 2016

(30) Foreign Application Priority Data
Jan. 2, 2014 (WO) .................. PCT/IB2014/058026

(51) Int. Cl.
*A61B 17/04* (2006.01)
*A61B 17/00* (2006.01)

(52) U.S. Cl.
CPC ...... *A61B 17/0469* (2013.01); *A61B 17/0483* (2013.01); *A61B 2017/00738* (2013.01); *A61B 2017/00907* (2013.01); *A61B 2017/0474* (2013.01); *A61B 2017/0475* (2013.01); *A61B 2017/0477* (2013.01); *A61B 2017/0496* (2013.01)

(58) Field of Classification Search
CPC ............ A61B 17/0469; A61B 17/0483; A61B 2017/0474; A61B 2017/0475; A61B 2017/0477; A61B 2017/0496
See application file for complete search history.

(56) References Cited

U.S. PATENT DOCUMENTS 2,595,086 A * 4/1952 Larzelere ......... A61B 17/12013
606/139
4,403,797 A * 9/1983 Ragland, Jr. ........... A01K 91/04
289/17

(Continued)

*Primary Examiner* — Sarah A Simpson
(74) *Attorney, Agent, or Firm* — Nir Lifshitz

(57) ABSTRACT

Embodiments of a knot pusher and methods of use thereof are disclosed, that are usable for pushing a knot formed from a suture, two limbs of the suture extending from the knot. The knot pusher comprises a distal head defining top and bottom walls terminating in a distal knot pushing surface. The distal head includes at least two side grooves defined between the top and bottom walls that extend proximally from the knot pushing surface. Each of these side grooves is operable to receive one of the limbs of suture. The distal head additionally comprises at least one suture guide coupled to the top and bottom walls for guiding the one of the limbs of suture into one of the side grooves.

15 Claims, 44 Drawing Sheets

(56) References Cited

U.S. PATENT DOCUMENTS

| | | | | |
|---|---|---|---|---|
| 5,403,330 | A | * | 4/1995 | Tuason ............ A61B 17/12013 606/139 |
| 5,439,470 | A | * | 8/1995 | Li ...................... A61B 17/0469 289/17 |
| 5,601,576 | A | * | 2/1997 | Garrison ............ A61B 17/0469 606/139 |
| 5,752,964 | A | * | 5/1998 | Mericle .............. A61B 17/0469 606/144 |
| 5,759,189 | A | * | 6/1998 | Ferragamo ......... A61B 17/0469 606/139 |
| 6,010,515 | A | * | 1/2000 | Swain ................ A61B 1/00089 600/104 |
| 7,981,125 | B1 | * | 7/2011 | Colvin ............... A61B 17/0467 606/148 |
| 2015/0335325 | A1 | * | 11/2015 | Harrison ............ A61B 17/0469 606/148 |

* cited by examiner

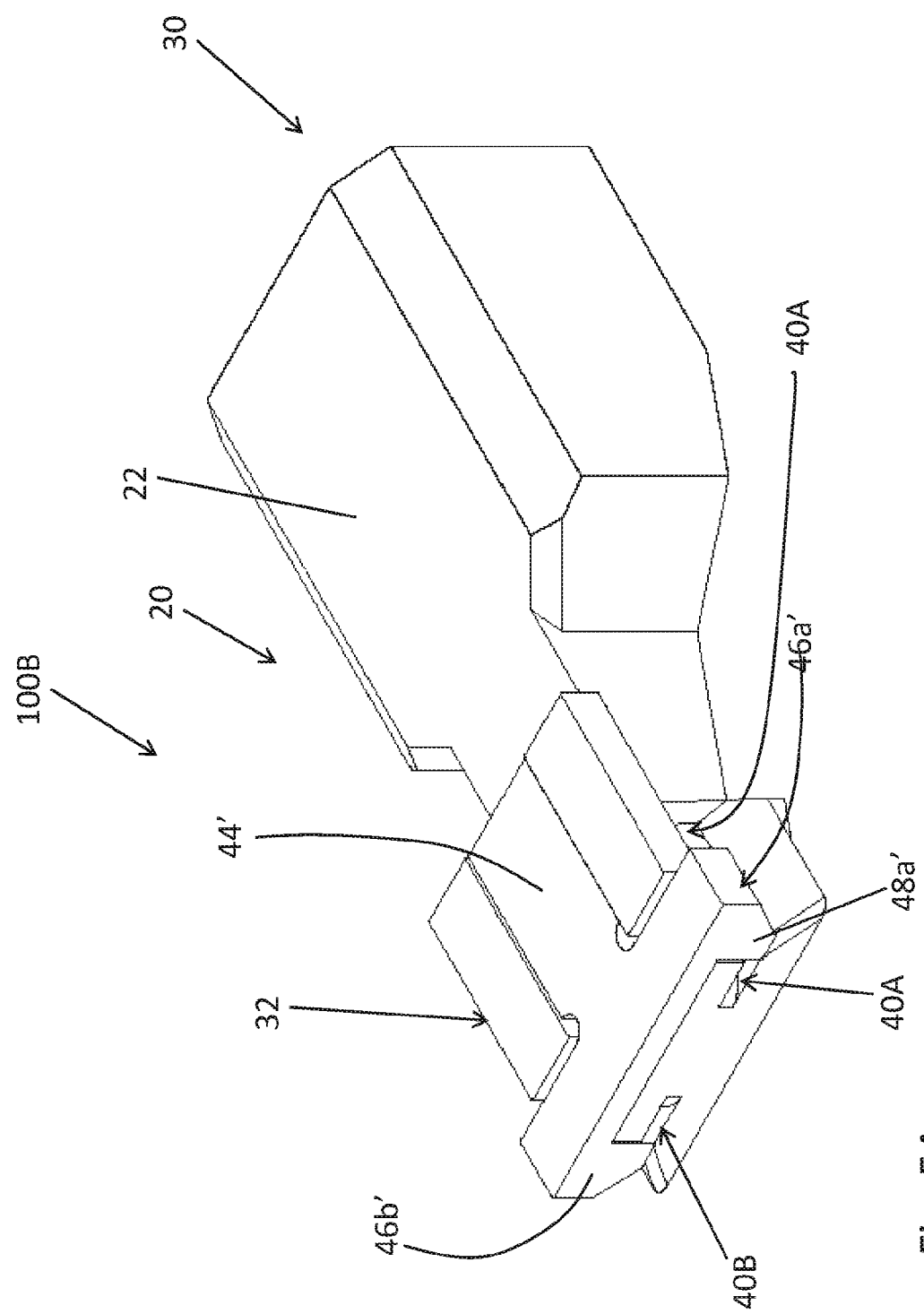

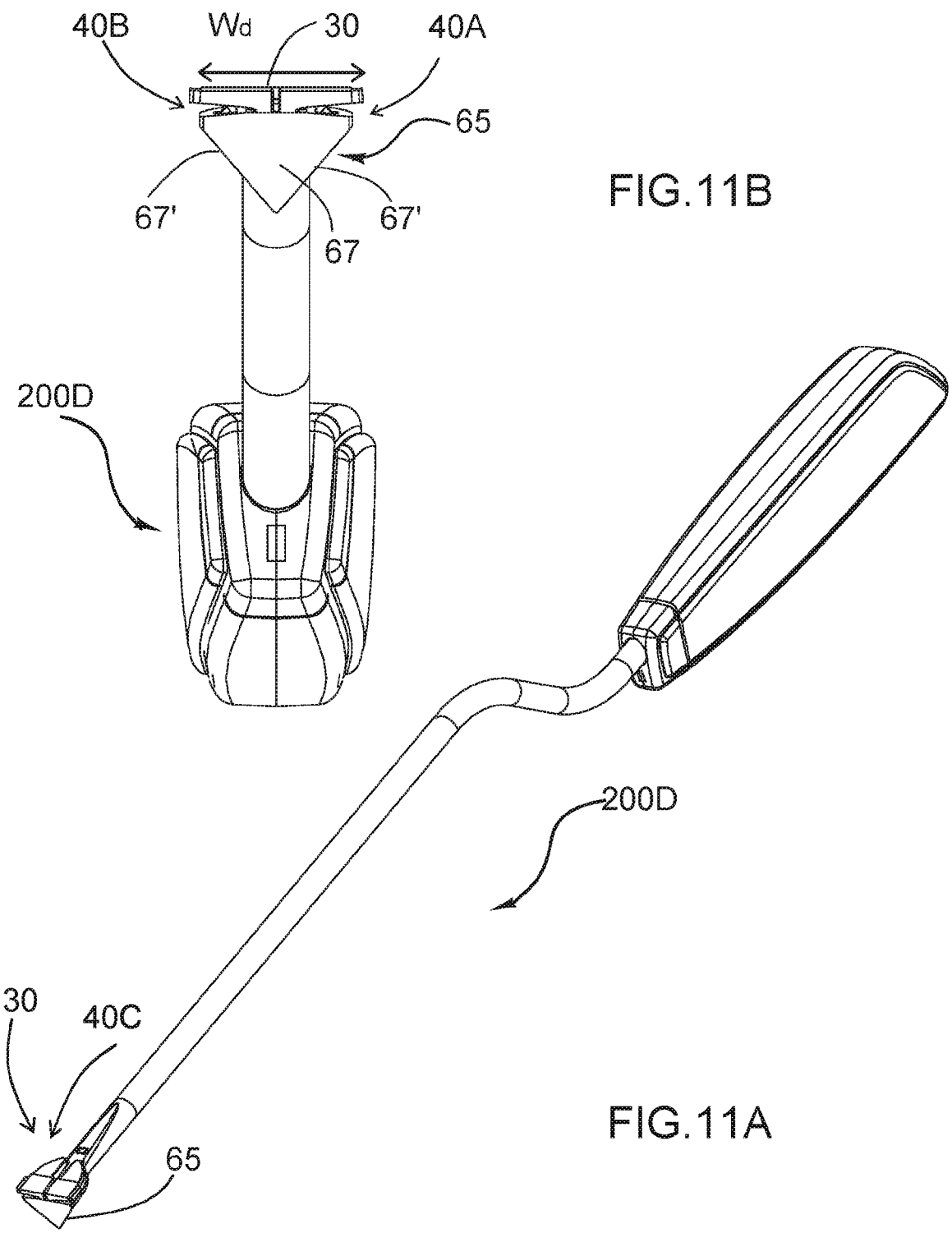

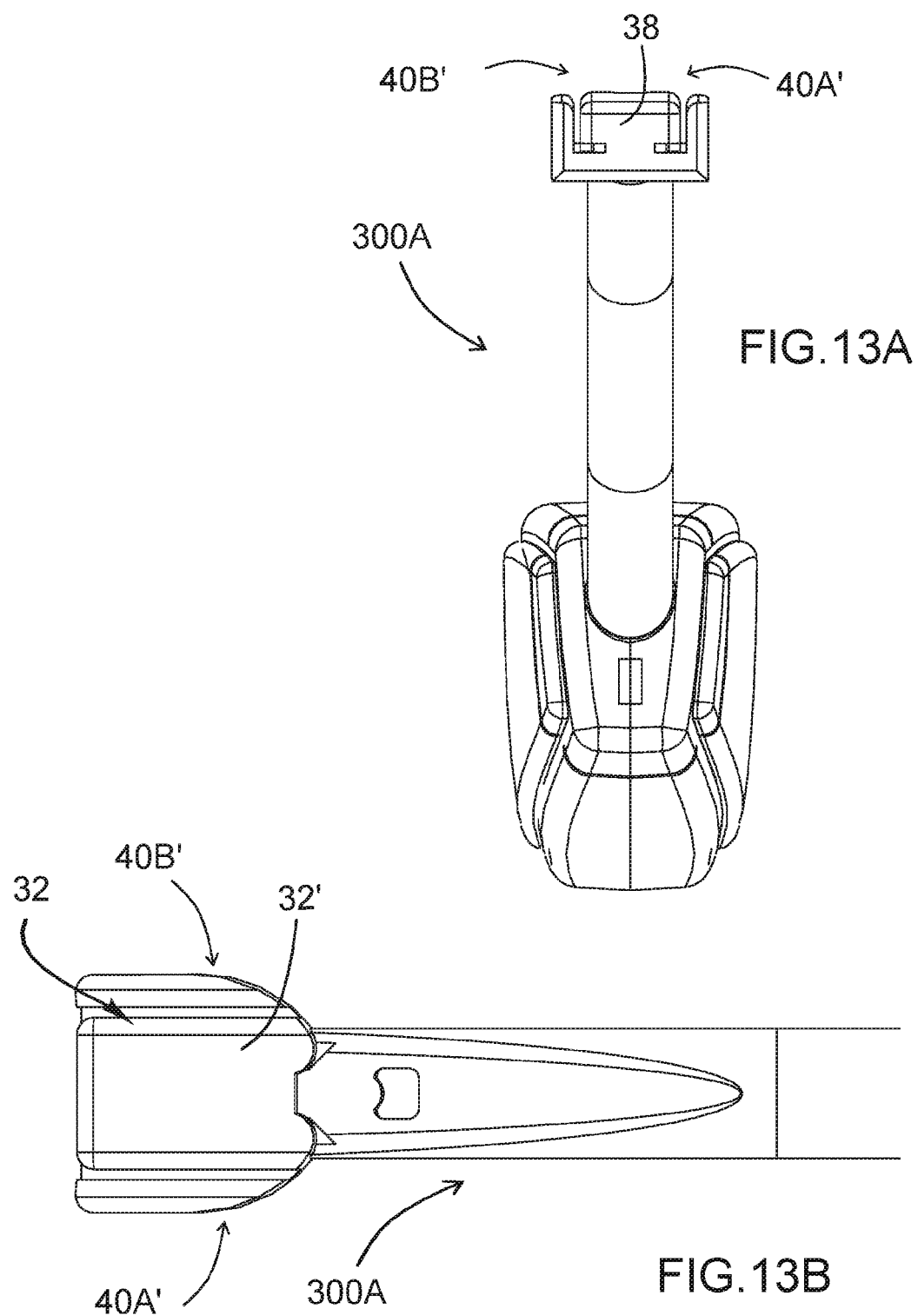

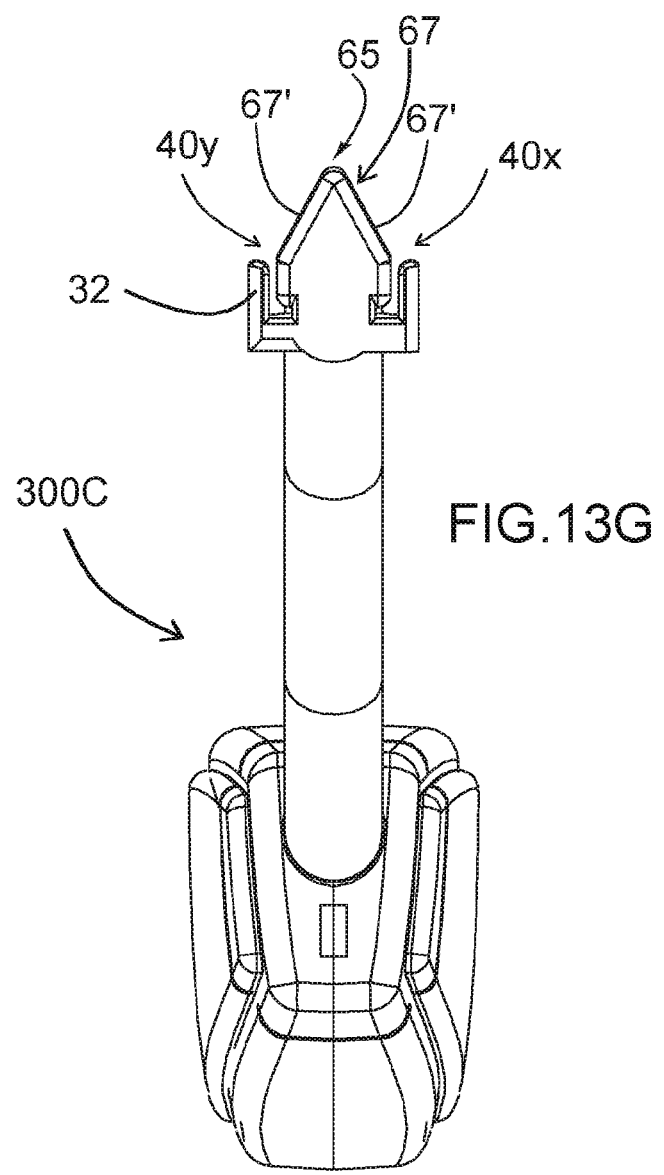

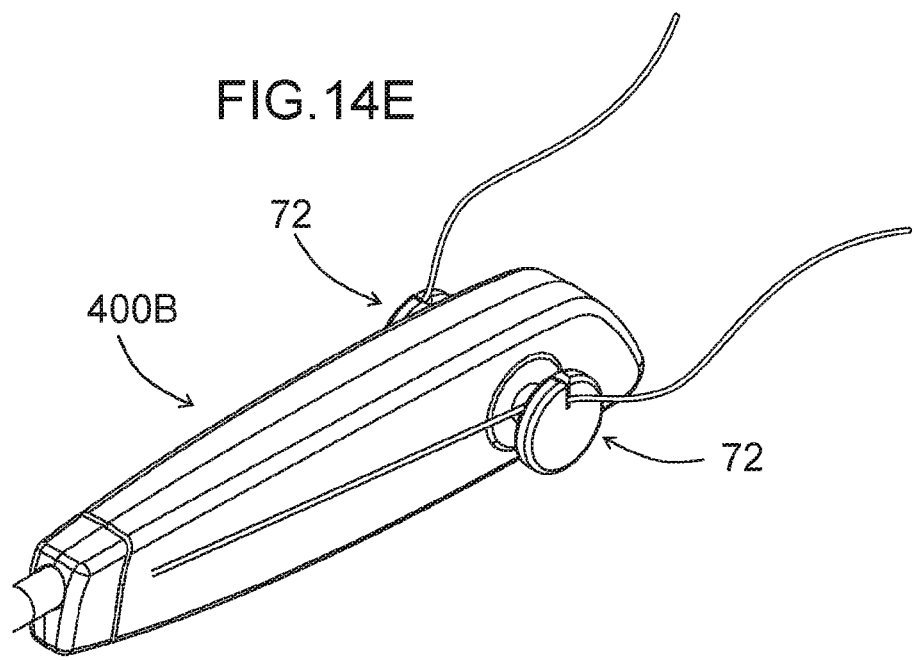
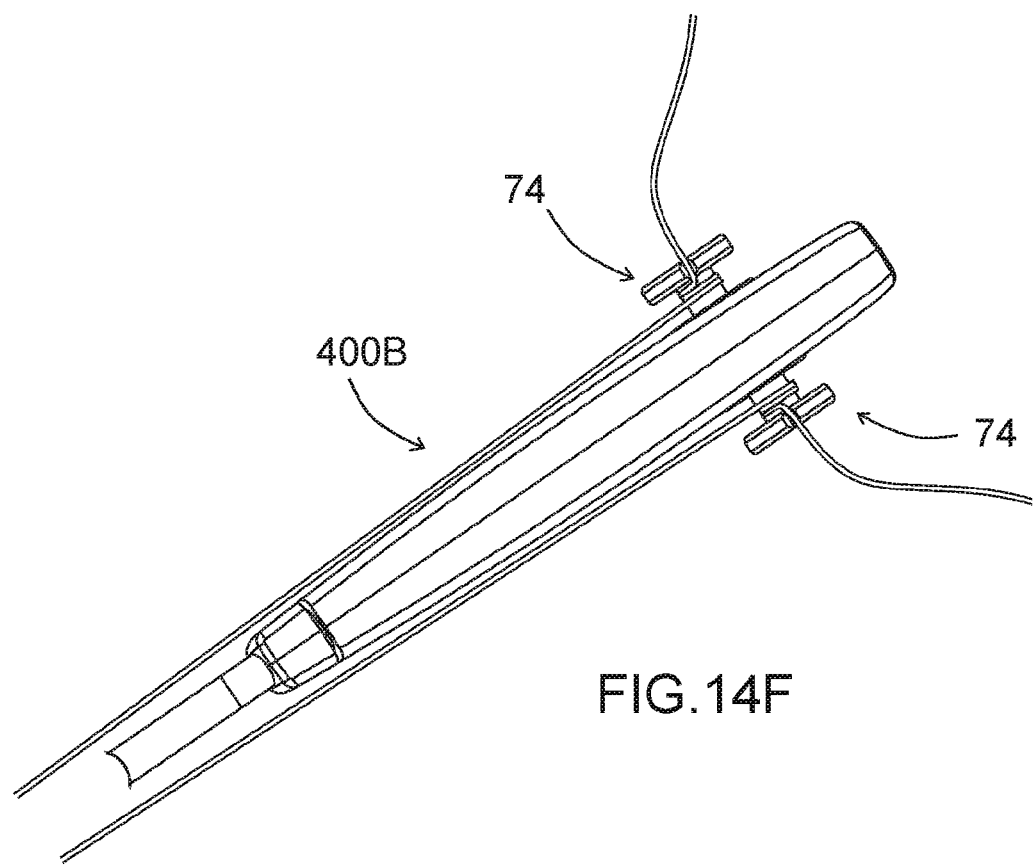

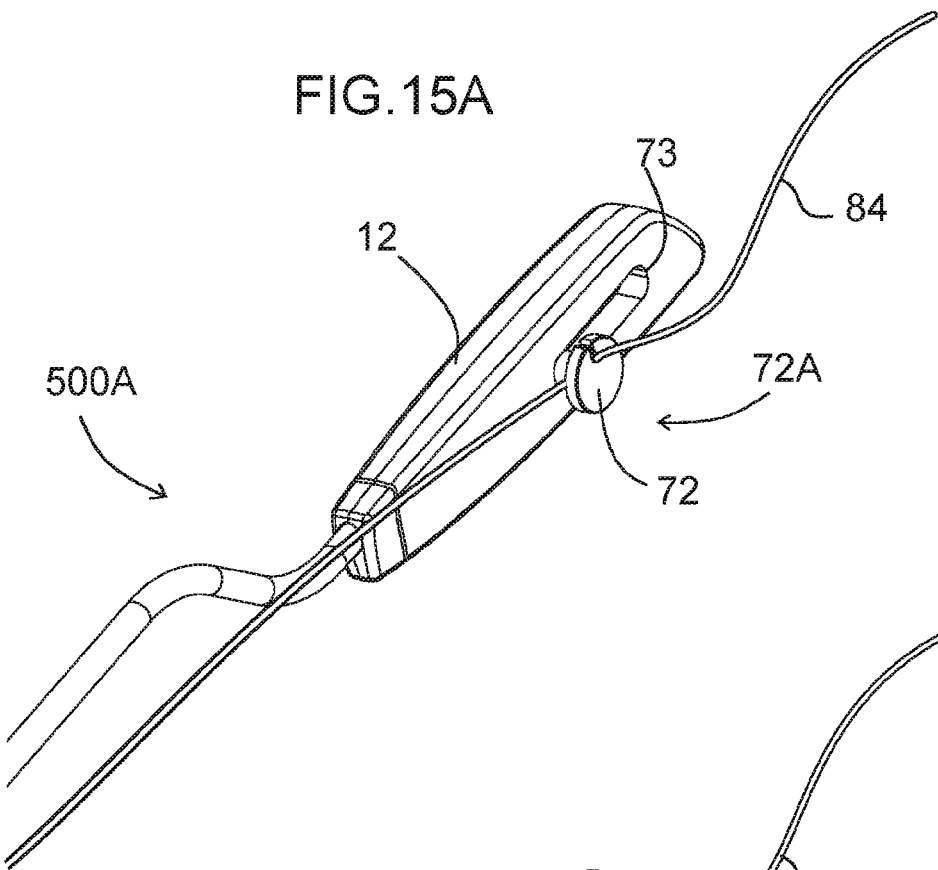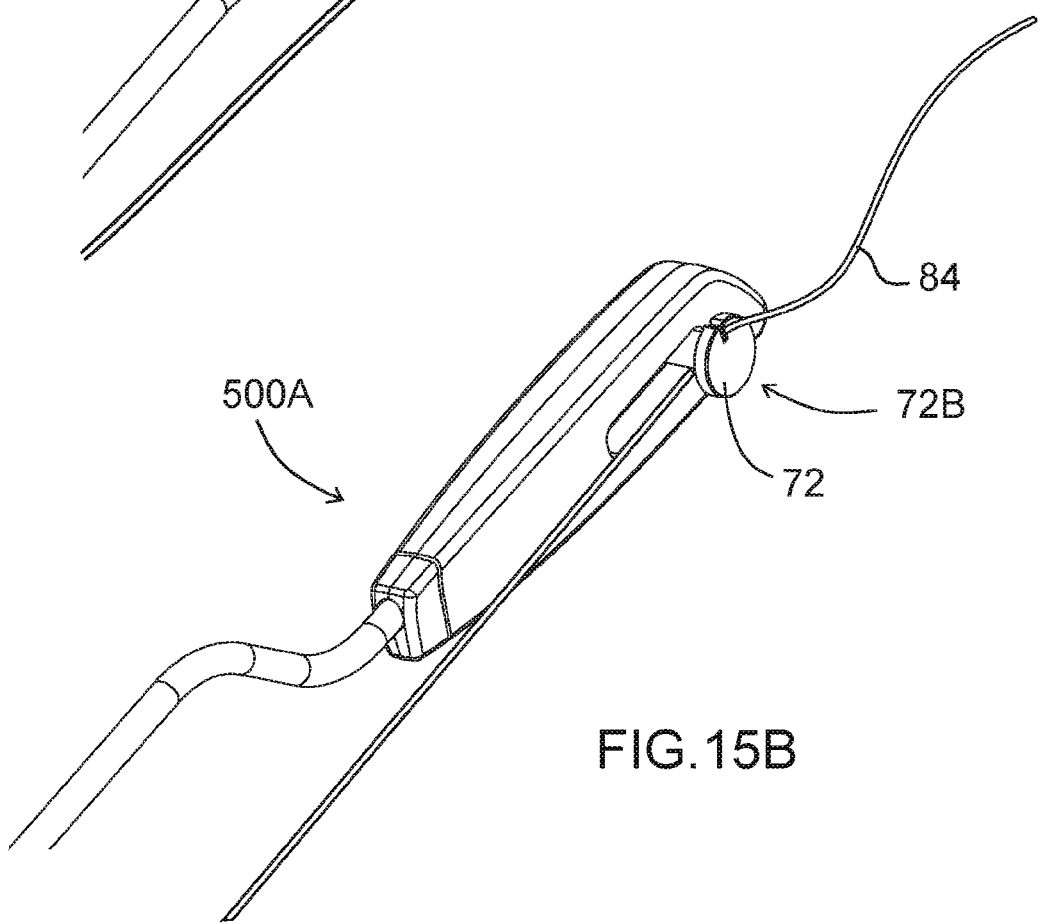

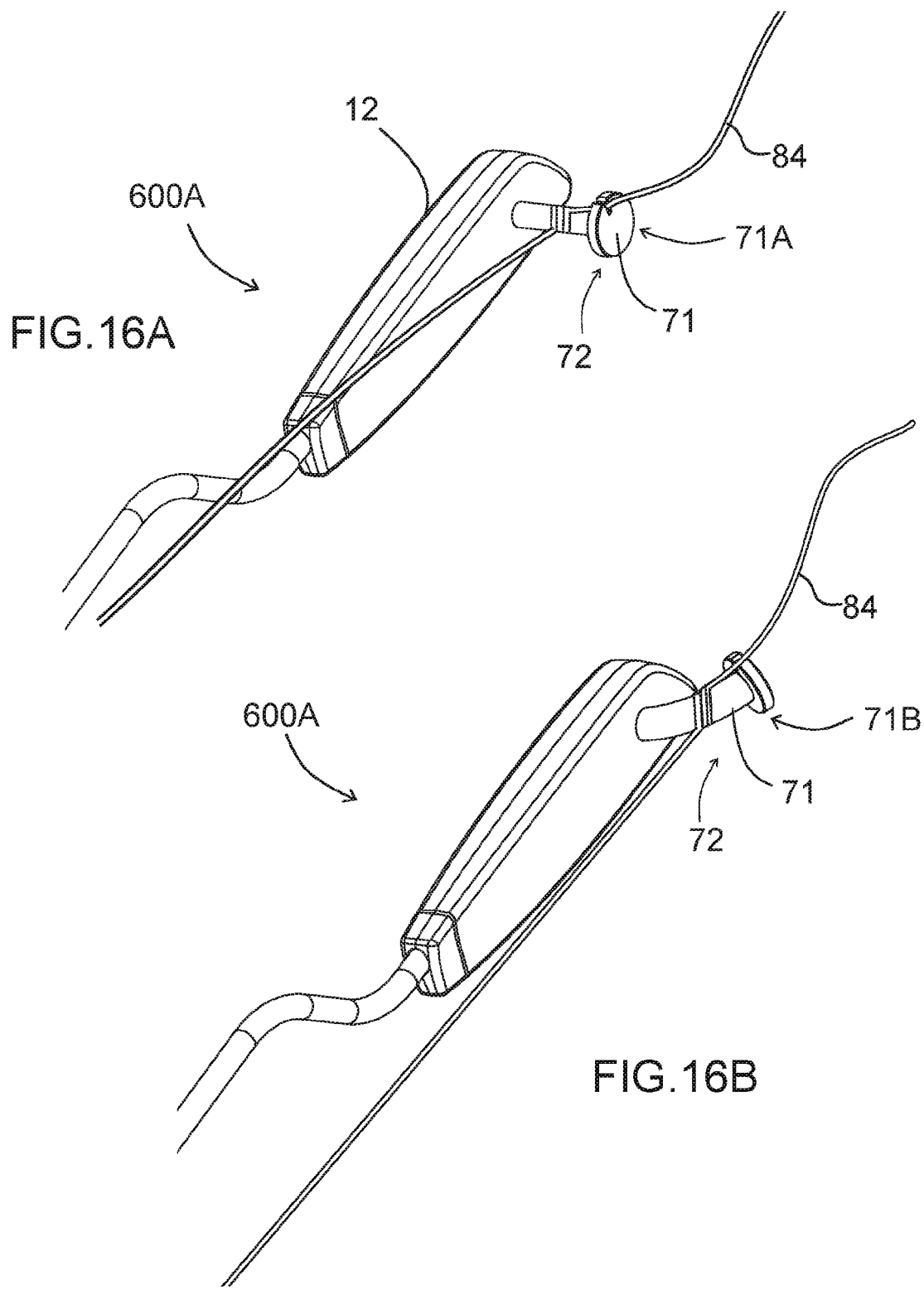

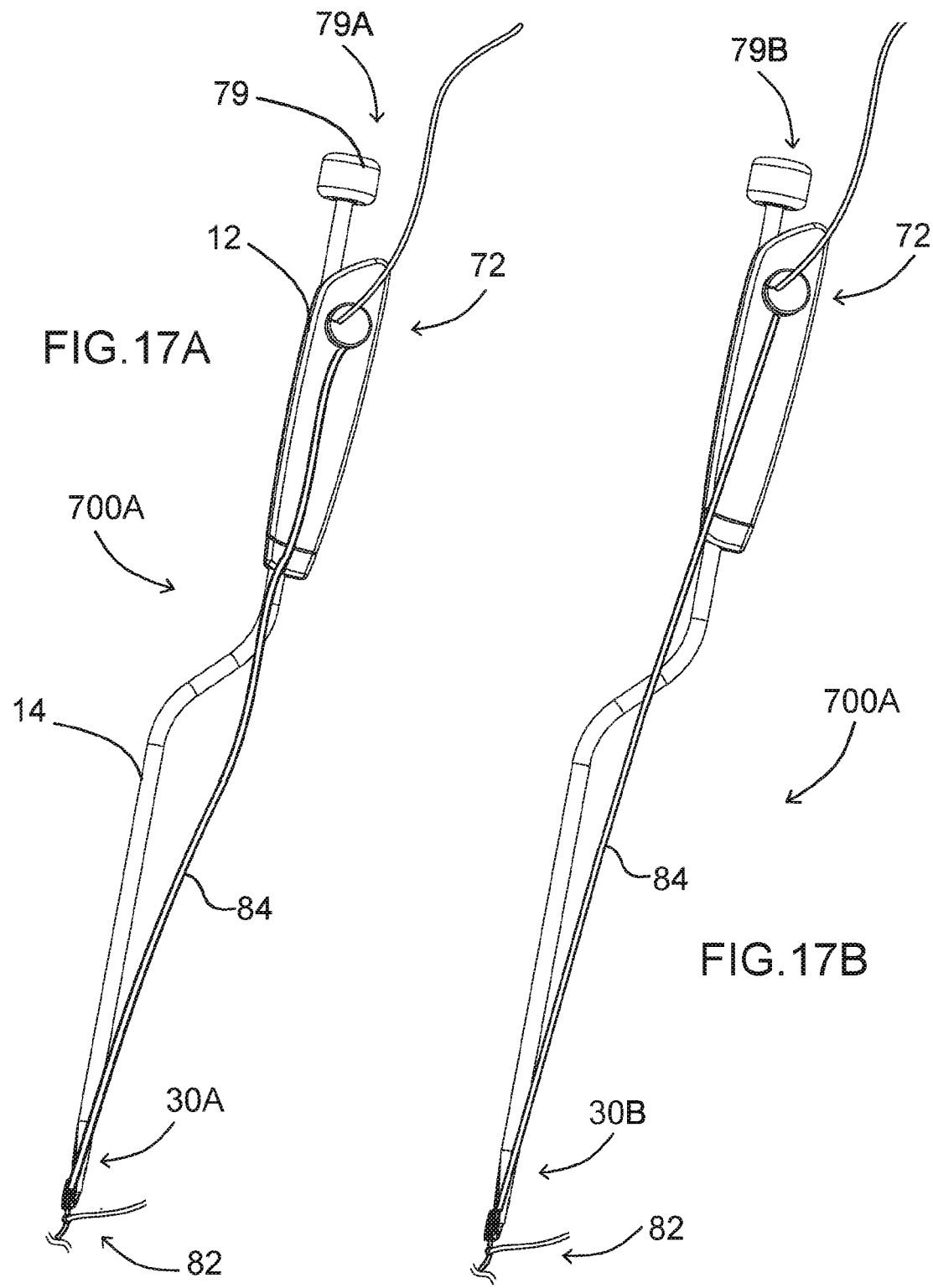

DEVICES AND METHODS FOR ADVANCING KNOTS

TECHNICAL FIELD

The disclosure relates to a medical device, more specifically to a knot pusher.

SUMMARY

In one broad aspect, embodiments of the present invention comprise a knot pusher usable for pushing a knot formed from a suture, two limbs of the suture extending from the knot, the knot pusher comprising: a distal head defining top and bottom walls terminating in a distal knot pushing surface; at least two side grooves defined between said top and bottom walls and extending proximally from said knot pushing surface, each of said side grooves operable to receive one of the limbs of suture; and at least one suture guide coupled to said top and bottom walls for guiding the one of the limbs of suture into one of the side grooves.

In a further broad aspect, embodiments of the present invention comprise a knot pusher usable for pushing various types of knots including overhand knots formed from a suture, two limbs of the suture extending from the knots, the knot pusher comprising: a distal head defining top and bottom walls terminating in a distal knot pushing surface; at least two side grooves defined between said top and bottom walls and extending proximally from said knot pushing surface, each of said side grooves operable to receive one of the limbs of suture; at least one side groove suture retaining element for retaining said one of the limbs of suture within one of said side grooves; and a suture containment element defined by one of said top and bottom walls; wherein the suture containment element defines a barrier for co-operating with the at least one side groove suture retaining element to retain said one of the limbs of suture within said one of the side grooves.

In another broad aspect, embodiments of the present invention comprise A knot pusher usable for pushing various types of knots including sliding knots and overhand knots formed from a suture, two limbs of the suture extending from the knots, the knot pusher comprising: distal head defining top and bottom walls terminating in a distal knot pushing surface; at least two side grooves defined between said top and bottom walls and extending proximally from said knot pushing surface, each of said side grooves operable to receive one of the two limbs of suture, at least one of said side grooves comprising an annulus forming an enclosed side groove defining a lumen there-through, said annulus defining a suture guide for guiding and retaining one of the two limbs of suture therein; and a top wall suture receiving element associated with said top wall for receiving one of the two limbs of the suture during advancement of said distal head to facilitate advancement of said sliding knot.

In still another broad aspect, embodiments of the present invention comprise a knot pusher usable for pushing various types of knots including overhand knots formed from a suture, two limbs of the suture extending from the knots, the knot pusher comprising: a distal head defining top and bottom walls terminating in a distal knot pushing surface, said distal head defining a longitudinal axis; at least two side grooves defined between said top and bottom walls and extending proximally from said knot pushing surface, each of said side grooves operable to receive one of the limbs of suture; and a guiding edge that extends from said distal head along a plane perpendicular to said distal head to maintain a separation between the two limbs of suture to enable loading of said two limbs of suture into the side grooves wherein said two limbs of suture are held substantially parallel to one another during use.

In one such embodiment, the knot pusher is usable to perform a method of sequentially advancing multiple preformed overhand knots, wherein the method comprises, for each of said multiple overhand knots: using the guiding edge to tease the two limbs of suture apart and guiding each of the two limbs of suture into the respective side grooves.

In still another broad aspect, embodiments of the present invention comprise a knot pusher usable for pushing various types of knots formed from a suture, two limbs of the suture extending from each knot, the knot pusher comprising: a distal head defining top and bottom walls terminating in a distal knot pushing surface, said distal head defining a longitudinal axis; at least two side grooves defined between said top and bottom walls and extending proximally from said knot pushing surface, each of said side grooves operable to receive one of the limbs of suture; and a knot tracking component associated with said knot pusher to enable tracking of a number of knots facilitated with said knot pusher during use.

In another broad aspect embodiments of the present invention comprise a knot pusher usable for pushing various types of knots including sliding knots and overhand knots formed from a suture, two limbs of the suture extending from the knots, the knot pusher comprising: a distal head defining top and bottom walls terminating in a distal knot pushing surface, said distal head defining a longitudinal axis; at least two side grooves defined between said top and bottom walls and extending proximally from said knot pushing surface, each of said side grooves operable to receive one of the limbs of suture; a top wall suture receiving element associated with said top wall for receiving one of the limbs of the suture during advancement of said distal head to facilitate advancement of said sliding knot; and a tension maintaining element associated with said knot pusher for frictionally engaging one of the limbs of suture along a portion of said knot pusher to enable said one of said two limbs of suture to be held in tension during use.

A knot pusher usable for pushing various types of knots including sliding knots and overhand knots formed from a suture, two limbs of the suture extending from the knots, the knot pusher comprising: a distal head defining top and bottom walls terminating in a distal knot pushing surface, said distal head defining a longitudinal axis; and at least two side grooves extending proximally from said knot pushing surface along said distal head, at least partially along a top face of said top wall forming top facing side grooves, each of said top facing side grooves being operable to receive one of the two limbs of suture during advancement of said distal head.

In one such embodiment, the knot pusher is usable to perform a method, comprising the step of: individually advancing one or more overhand knots using both of said top-facing side grooves, each one of said two limbs of suture being held in a respective one of said side grooves during advancement of the one or more overhand knots. In an example of this embodiment, the method further comprises advancing a sliding knot using one of said top facing side grooves prior to advancing said one or more overhand knots, said one of the two limbs of suture being held within one of said side grooves during said advancement of the sliding knot.

BRIEF DESCRIPTION OF THE DRAWINGS

In order that the invention may be readily understood, embodiments of the invention are illustrated by way of examples in the accompanying drawings, in which:

FIGS. 5A-5B illustrate an alternate embodiment of a knot pusher in accordance with the present invention;

FIGS. 11A-11E, illustrate an alternate embodiment of a knot pusher, with a suture guide comprising a guiding edge, in accordance with an embodiment of the present invention;

FIGS. 13A-13D, illustrate an alternative embodiment of a knot pusher with top facing side grooves, in accordance with an embodiment of the present invention;

FIG. 13G, illustrate a further alternative embodiment of a knot pusher, with oblique top facing side grooves, in accordance with an embodiment of the present invention;

FIG. 14D-14F, illustrate a further alternative embodiment of a knot pusher, dual tension maintaining elements, in accordance with an embodiment of the present invention;

FIG. 15A-15B, illustrate a further alternative embodiment of a knot pusher, with a moveable tension maintaining element, in accordance with an embodiment of the present invention;

FIG. 16A-16B, illustrate a further alternative embodiment of a knot pusher, with a moveable tension maintaining element, in accordance with an embodiment of the present invention; and FIG. 17A-17B, illustrate a further alternative embodiment of a knot pusher, with a tension maintaining means, in accordance with an embodiment of the present invention.

DETAILED DESCRIPTION

Figure 1A:
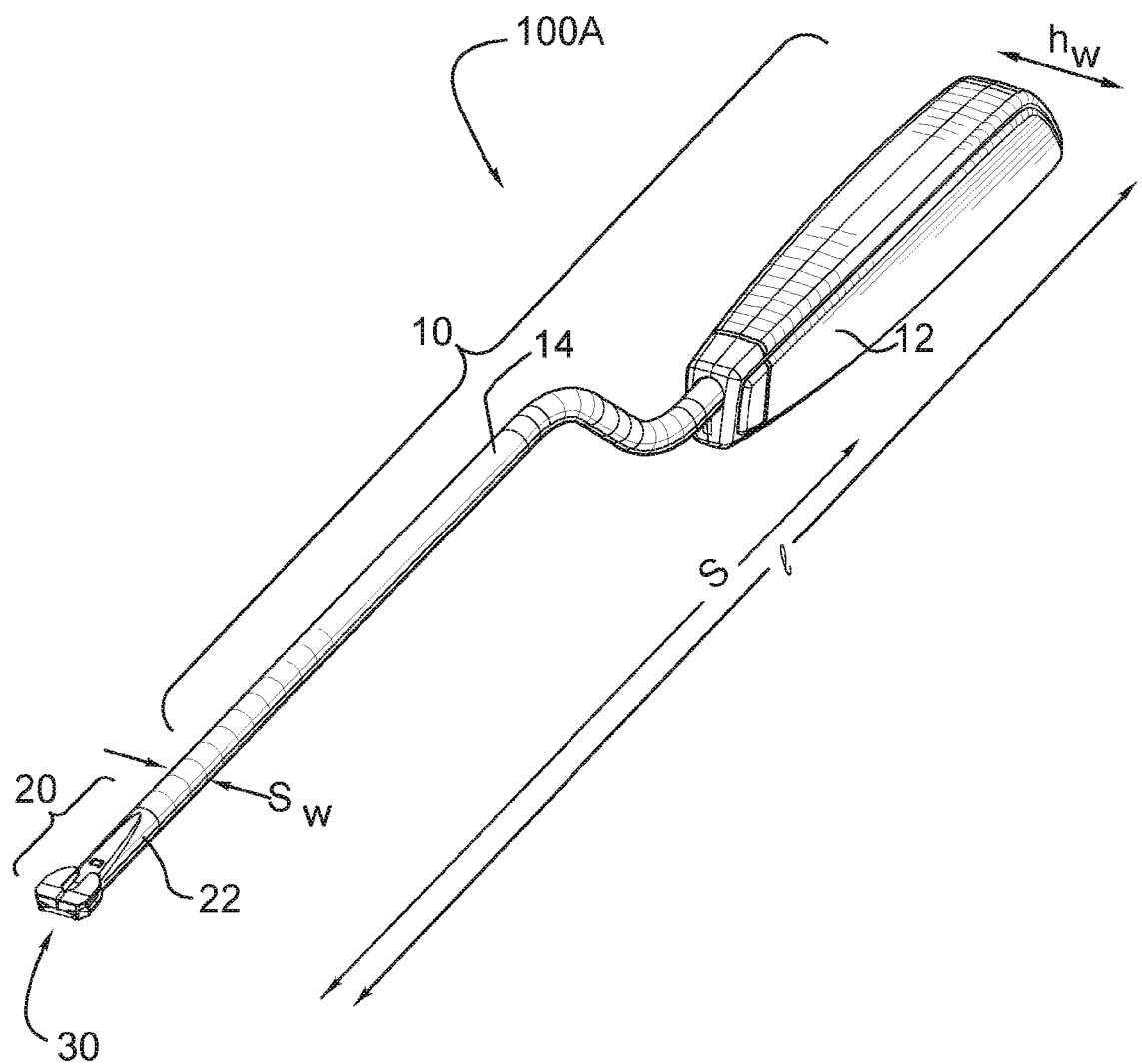
FIG. 1A illustrates a top, front perspective view of a knot pusher in accordance with an embodiment of the present invention.

In one broad aspect, embodiments of the present invention provide a means for advancing and tightening a knot formed in a suture at a site within a region of tissue of a patient's body. In some applications, this may be taken to include a site that is on a surface of a patient's body. In alternate applications, the site may be remote or within a region of tissue to which access is limited or restricted. Such applications particularly warrant the use of a knot pusher to advance and tighten the knot.

In some applications it may be desirable to apply a sliding knot in order to secure the suture. In a particular example, a sliding knot may be deployed after delivery of suture through a region of tissue at the site of a defect, for example at an annulus fibrosis of an intervertebral disc. In some such examples, access to the intervertebral disc may be provided through a portal, inserted for example through a lamina of a vertebra, to allow the suture to be passed through to the affected disc. A sliding knot may then be deployed to secure the suture.

In such situations, since access to the intervertebral disc is restricted, a knot pusher may be utilized to advance the sliding knot through the portal towards the site of the defect. The knot pusher may allow for advancement of the sliding knot and may further enable initial approximation of the tissue at the defect. The knot pusher may additionally be used to tighten and lock the sliding knot. Oftentimes, in order to further reinforce the sliding knot, the physician desires to apply one or more additional half-hitches or overhand knots over the sliding knot. These may help ensure that the sliding knot does not open or unravel after the procedure. The mechanism/procedure for pushing and tightening the knot is different for both sliding knots and overhand knots and advancing these different types of knots typically requires use of a plurality of knot pushers, each designed for a particular type of knot.

The present inventors have discovered and reduced to practice several embodiments of a knot pusher for pushing both sliding knots and overhand knots. Pushing both a sliding knot and an overhand knot in a medical procedure using the same device is achieved, for example, by providing a knot pusher having a suture receiving element, such as an intermediate groove, for holding one of the two limbs of the suture forming the sliding knot to allow the knot pusher to push the sliding knot. The knot pusher additionally has opposed side grooves for receiving, holding or guiding one or both limbs of the suture forming an overhand knot to allow the knot pusher to push the overhand knot.

In some embodiments, the knot pusher comprises features to facilitate suture engagement with the knot pusher and to reduce the operating time. In one specific example, the knot pusher has at least one suture retaining element to retain a limb of the suture within one of the side grooves to prevent disengagement of the suture limb from the knot pusher during advancement of the distal head to push the overhand knot.

Such embodiments are particularly useful and advantageous, for example, when there is limited access to the tissue site where the knots are being deployed. Embodiments of the present invention avoid the use of multiple devices to deploy different types of knots, and as such reduces the number of devices that need to be utilized to complete the procedure. Furthermore, embodiments of the present invention provide a device that enables both effective and efficient delivery of different types of knots to the desired tissue location without disengagement of the suture from the device.

In additional embodiments of the present invention a knot pusher is provided that comprises a means to facilitate loading of suture. Such embodiments are particularly useful and advantageous in situations, where there may be limited room to maneuver the knot pusher in terms of positioning the knot pusher device to capture limbs of suture. For example, in some situations the knot pusher may be needed to advance a suture knot deep into the patient's body, the knot pusher may be inserted through a narrow portal in order to allow a knot to be advanced to the target site within the patient's body. In such situations it may be difficult to reposition or adjust the knot pusher to allow the suture limbs to be captured separately within each of the side grooves. In other words, there may not be sufficient room to allow individual insertion of each of the limbs of suture into the respective side grooves. In some such embodiments, the knot pusher is equipped with one or more features to facilitate insertion of one or more of limbs of suture into the side grooves. In some such embodiments of the present invention a suture guide is provided to guide at least one of the two limbs of the suture into at least one of the side grooves to assist in positioning the at least one of the two limbs of suture therein during use of said knot pusher for advancing an overhand knot.

In one such broad aspect, embodiments of the present invention comprise a knot pusher usable for pushing a knot formed from a suture, two limbs of the suture extending from the knot, the knot pusher comprising: a distal head defining top and bottom walls terminating in a distal knot pushing surface; at least two side grooves defined between said top and bottom walls and extending proximally from said knot pushing surface, each of said side grooves operable to receive one of the limbs of suture; and at least one suture guide coupled to said top and bottom walls for guiding the one of the limbs of suture into one of the side grooves.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In accordance with an embodiment of the present invention, and as shown in FIG. 1A, a knot pusher 100A is disclosed for advancing a knot formed in a suture to a site within a patient's body and for additionally tightening the knot. In some embodiments, the knot pusher 100 allows a knot to be advanced to a site that may be remote or within a region of tissue to which access is limited or restricted, the knot terminating in two strands of suture.

As used herein, the phrases "two strands of suture", "two ends of suture", "two limbs of suture" and variations thereof, are interchangeable and refer to the portions of suture exiting/deriving from/outside a suture knot, i.e. the portions of suture that are not constrained by the knot. Typically, these portions are parts of a single strand or thread of suture. Although the term '"end" of suture' is used, in this context it should be understood to refer to that portion of the suture exiting the knot, rather than to the actual physical end of the suture strand.

In addition, it should be understood that the term strand as used herein refers to a portion of suture regardless of the number of filaments included therein (i.e. both monofilament and multifilament sutures or portions thereof are referred to as a strand of suture).

In some portions of the description below, and as would be understood by one of skill in the art based on the context, a 'strand' of suture may refer to either the working part, standing part or both the working and standing part of the knot construct. In some such embodiments the two strands or limbs exiting the knot are understood to be the standing part of the suture and the part of the suture forming the knot that is used to retain the suture is understood to be the working part of the suture.

Figure 1B:
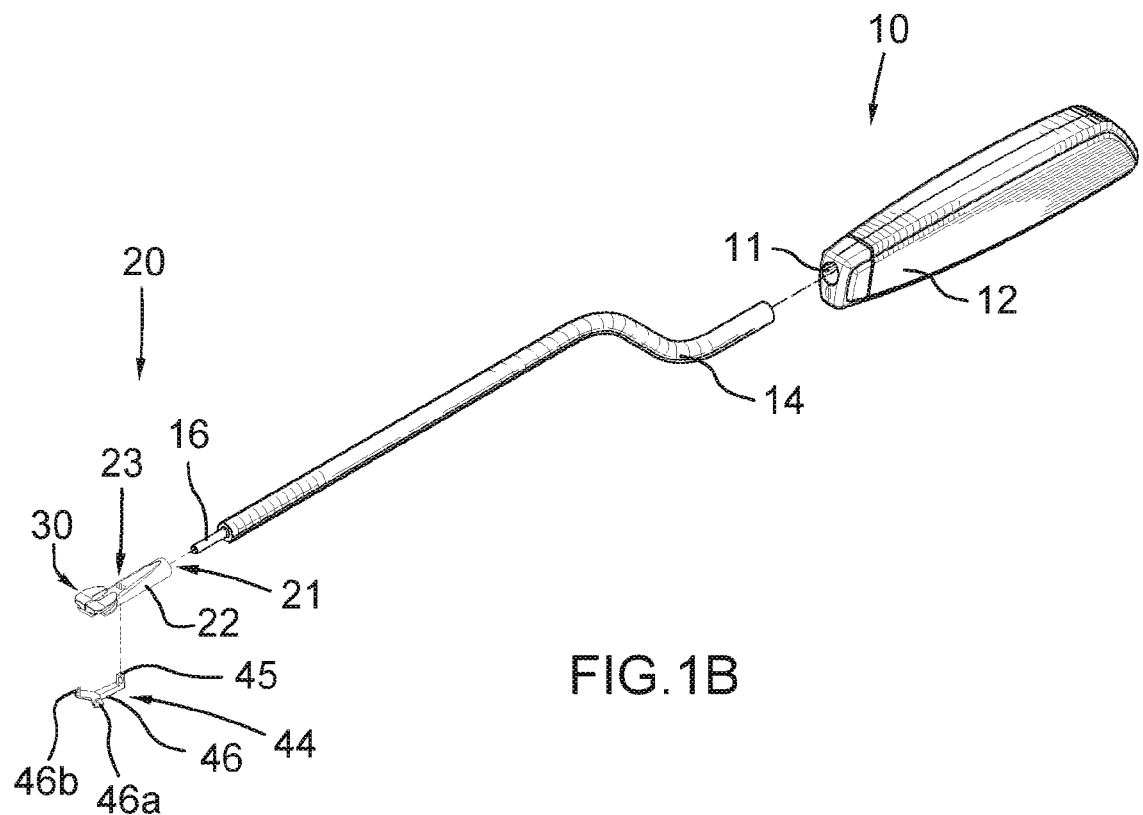
FIG. 1B illustrates an exploded view of a knot pusher in accordance with an embodiment of the present invention.
Figure 1C:
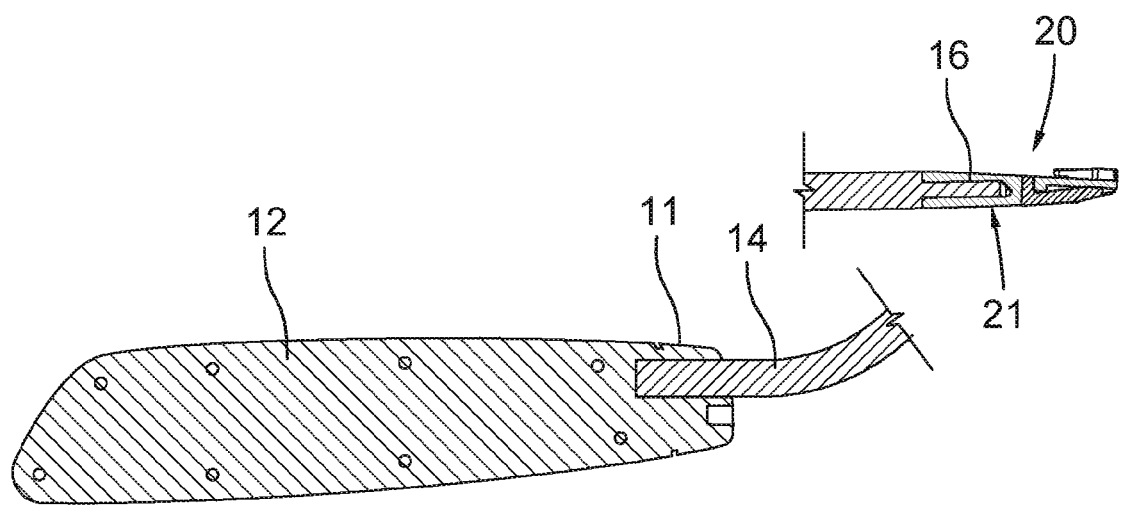
FIG. 1C illustrates a right side cross-sectional view of proximal and distal portions of a knot pusher in accordance with an embodiment of the present invention.

As shown in FIG. 1A, the knot pusher 100A comprises a proximal portion 10 that is coupled to a distal portion 20. The proximal portion 10 comprises a handle 12 that is coupled to the distal portion 20 via an elongated shaft 14 (of the proximal portion 10). The handle 12 is operable to exert a force along the elongated shaft 14 that is transmitted to the distal portion 20 for pushing the knot. In one specific example, as shown in FIGS. 1B and 1C, the shaft 14 co-operatively engages with the handle 12. For example, the shaft 14 is received within and fits within a recess 11 within the handle 12. Additionally, the shaft 14 may be secured within the recess 11 using an adhesive, such as a Loctite® 4011 adhesive.

The distal portion 20 further comprises a distal head 30 that is coupled to the elongated shaft 14 via a neck portion (or simply "neck") 22 formed within the distal portion 20. In one specific example, as shown in FIGS. 1B and 1C, the shaft 14 comprises a peg or protrusion 16 that is received within a recess 21 within the distal portion 20 and co-operatively engages therewith. In one specific example, the peg 16 may be secured within the recess 21 using an adhesive, such as Loctite® 4011 adhesive. The distal head 30 interacts with the knot, as well as one or more strands of suture coupled to the knot during advancement of the distal portion 20, to advance and tighten the knot at the desired tissue site. In other embodiments the distal head 30 may be coupled directly to the shaft 14 without the use of an intermediate neck portion 22. In some examples, the neck portion 22 may be a part of the shaft 14. In other embodiments, the distal head 30 may be detachably coupled to the shaft 14 or the neck portion 22. This may permit the distal head 30 to be formed as a single-use component whereas the shaft 14 and the handle 12 may be reusable and may be sterilizable to permit multiple uses. In still further examples, the distal head 30 may be provided in various sizes and may be customizable for use in different areas in the body or to accommodate various sizes of sutures or different types of knots.

Figure 1D:
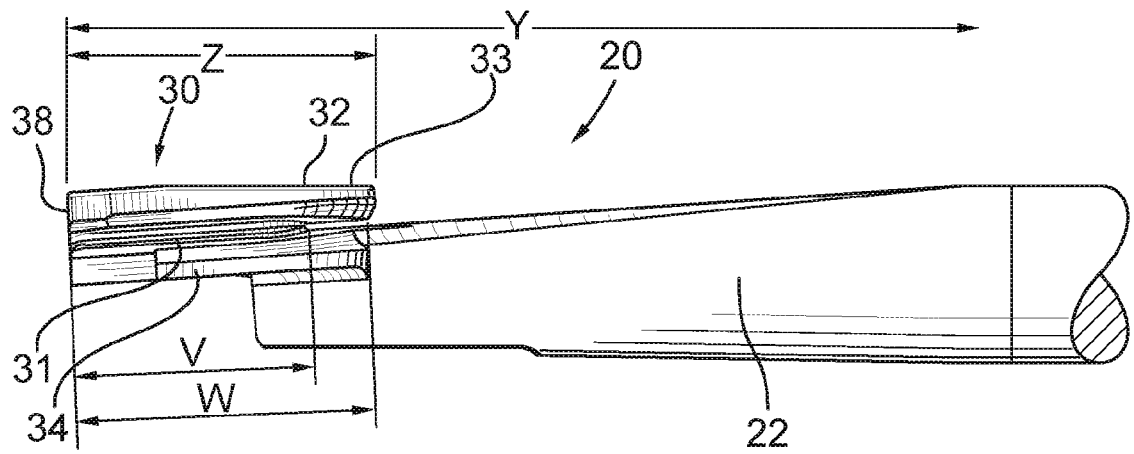
FIG. 1D illustrates a left side view of a distal portion of a knot pusher in accordance with an embodiment of the present invention.
Figure 1E:
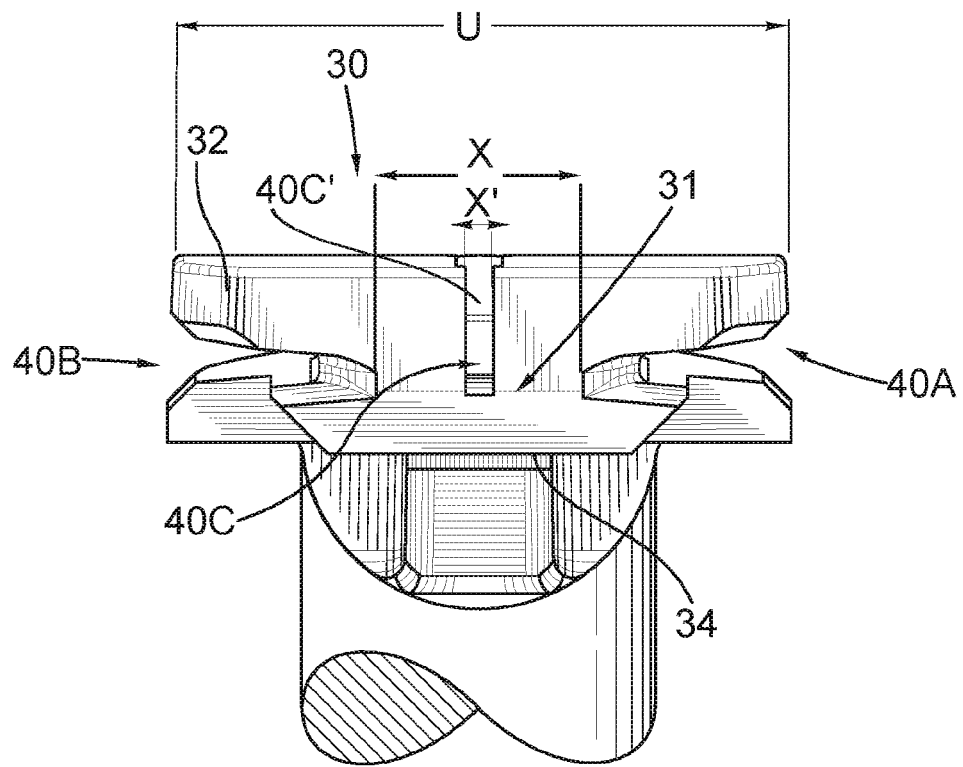
FIG. 1E illustrates a front end view of a distal portion of a knot pusher in accordance with an embodiment of the present invention.
Figure 2:
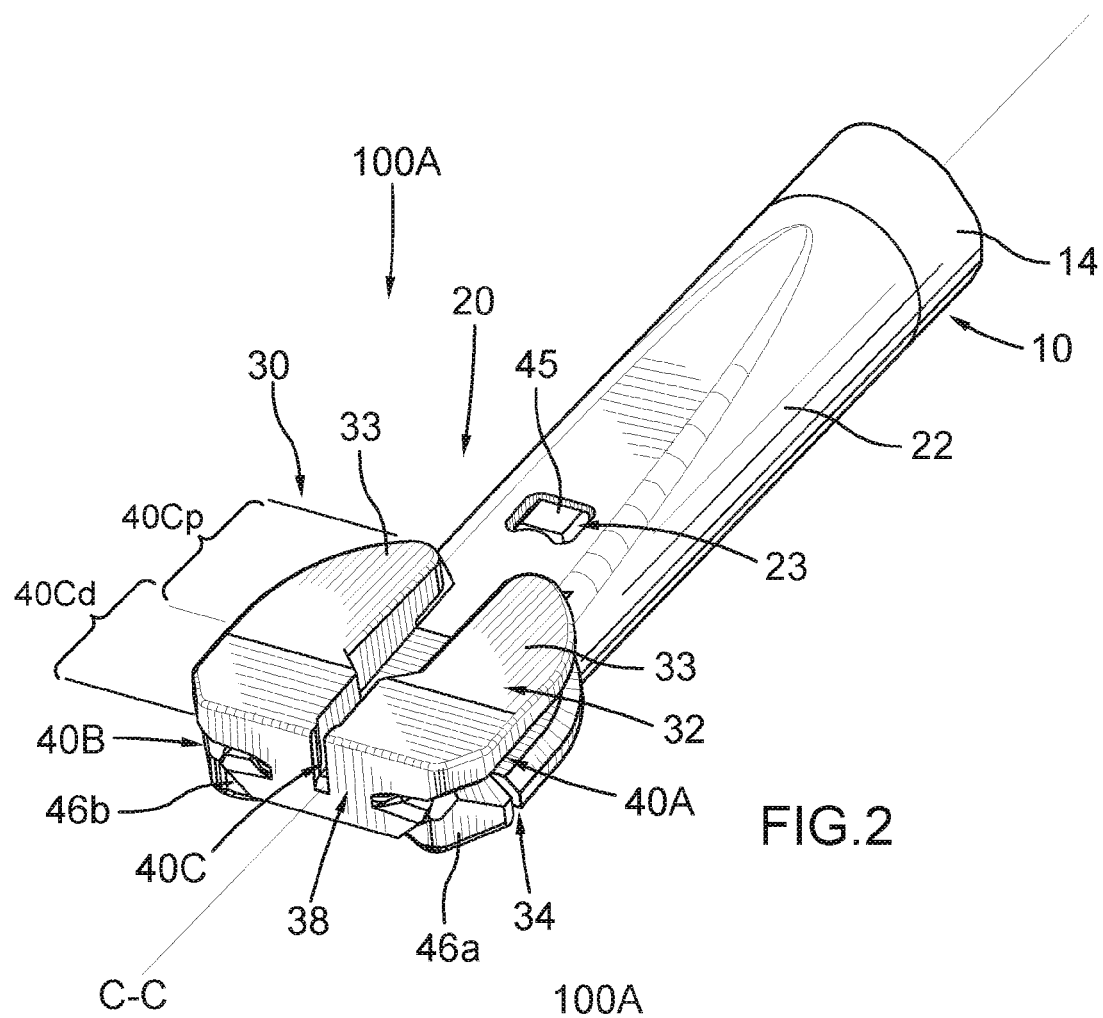
FIG. 2 illustrates a top front perspective view of a distal portion of knot pusher in accordance with an embodiment of the present invention.
Figure 3:
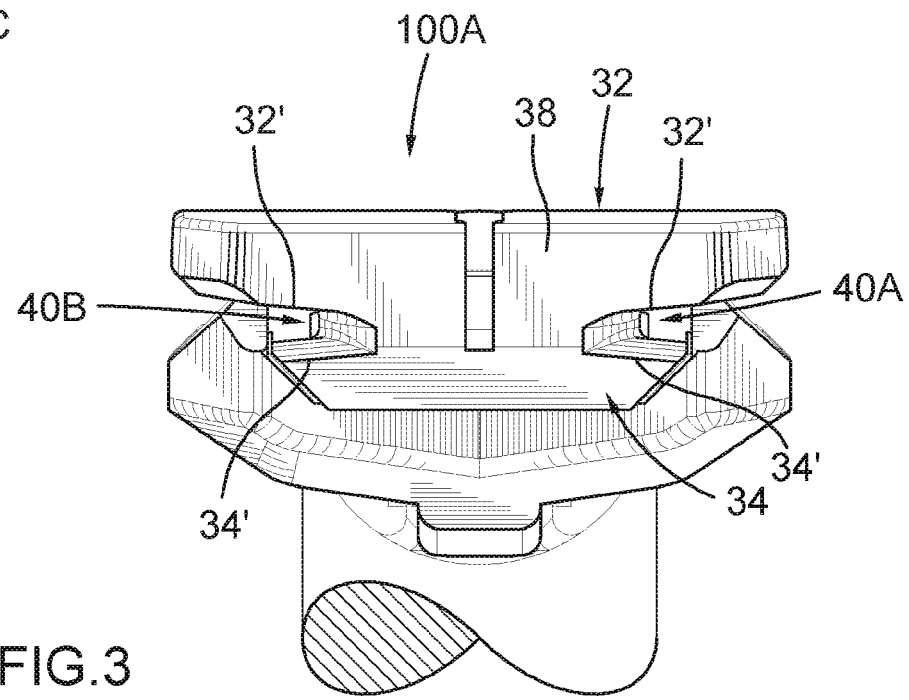
FIG. 3 shows a front view of a distal portion of knot pusher in accordance with an embodiment of the present invention.

With reference now to FIG. 1D, the distal head 30 comprises top and bottom walls (or faces) 32, 34 (which may alternatively be referred to as upper and lower walls or faces 32,34) respectively that terminate in a distal knot pushing surface 38 that interacts directly with the knot to push the knot distally. The distal knot pushing surface 38 is visible in FIG. 1E that shows a front view of the distal head 30. In some embodiments, the distal knot pushing surface 38 is a substantially flat planar surface. In some embodiments, the bottom wall 34 is formed integrally with the neck 22 and is planarly offset from the top wall 32, as seen in FIGS. 1D-1E and 2. In other words, the top and bottom walls 32, 34 are along separate planes that are offset, but possibly parallel, relative to one another. Additionally, as shown in FIG. 3, the top and bottom walls 32, 34, define two laterally opposed side grooves 40A and 40B, extending between the respective inner surfaces 32' and 34' of each of the top and bottom walls 32, 34. Each of the side grooves 40A and 40B are designed to receive, hold, contain or retain at least one of the two strands of suture extending or deriving from a knot. In one example, the top and bottom walls 32, 34 are chamfered to facilitate the loading of the suture within the side grooves 40A, 40B. In some embodiments, the side grooves are continuous, i.e. a single continuous groove extends along both sides as well as along the knot pushing surface 38.

Furthermore, as shown in FIGS. 1D and 1E, a portion of each of the top and bottom walls 32 and 34 may be joined along a longitudinal axis of the distal head 30, defining a support 31' that extends along the longitudinal axis and is positioned transversally between the longitudinally extending side grooves 40A and 40B. The support 31' is defined as a region or component of the distal head 30 that connects the top and bottom walls 32, 34 so that they are connected to or integral with one another along the longitudinal axis of the distal head 30. In one particular example, as shown, the distal head 30 comprises a central support 31 that connects the top and bottom walls 32, 34 such that are connected along the central axis of the distal head 30. The side grooves 40A and 40B do not extend transversally along the central support 31. Therefore, the side grooves 40A and 40B are spaced apart laterally from one another by a fixed distance that may be equal to the width of the central support 31. This forces the two suture strands of an overhand knot, each positioned in one of the side grooves 40A and 40B, to spread apart as the knot is being pushed and/or advanced. The grooves 40A and 40B are distanced from one another to enable the two suture strands to be oriented at an angle of about 180° with respect to the overhand knot along the knot pushing surface 38 and with respect to one another, to permit effective tightening and locking of the overhand knot. The further the side grooves 40A and 40B are spaced apart from one another, the closer the respective angle between the two suture strands is to 180 degrees. In some embodiments, the distance between the side grooves 40A and 40B is related to the width of the side grooves 40A, 40B and in some embodiments this distance may also relate to the width of the suture to be used with the knot pusher. In one particular embodiment, the side grooves 40A and 40B are spaced apart by a distance that is equal to about 10 times the diameter of the suture being used which may be, for example, substantially equivalent to the width of each of the two side grooves 40A, 40B. In one specific example, the distance between the side slots for a 2-0 suture may be about 0.110".

As shown in FIG. 1E and FIG. 2, the knot pusher 100A additionally comprises a suture receiving element, for example associated with the top wall of the distal head, i.e. a top wall suture receiving element. The top wall suture receiving element may be, for example, a component able to receive a limb of a suture such as a 'gun sight'-type structure which has two side walls protruding from the top wall and defining a gap or groove into which a suture may be received. Alternatively, as illustrated in FIG. 1E and FIG. 2, the suture receiving element comprises an intermediate groove 40C formed within the top wall or face 32 that extends proximally from the knot pushing surface 38 and extends longitudinally along the top wall 32. The intermediate groove 40C opens into the top face 32. More specifically, in some embodiments, the intermediate groove 40C may be formed within the support 31' such as the central support 31 as described above. In some embodiments, the intermediate groove 40C may be formed within the top wall 32 but may extend (in depth) into a portion of the bottom wall 34. The intermediate groove 40C is thereby in communication with the knot pushing surface 38 and terminates at the knot pushing surface 38. The intermediate groove 40C allows one of the two strands of suture exiting a sliding knot to be held therein as the knot pusher 100A is advanced to push the sliding knot using the knot pushing surface 38.

In some embodiments, at least a portion of the intermediate groove 40C, for example at least along a distal portion thereof, such as portion 40Cd, has a width smaller than that of the knot to prevent the knot from sliding into the groove as the knot pusher 100 is advanced distally to push the knot. More specifically, the intermediate groove 40C allows a post (as discussed with reference to FIG. 7) of the sliding knot to be positioned or received within the intermediate groove 40C while the knot pusher 100A is advanced to push the sliding knot against the tissue.

Figure 1F:
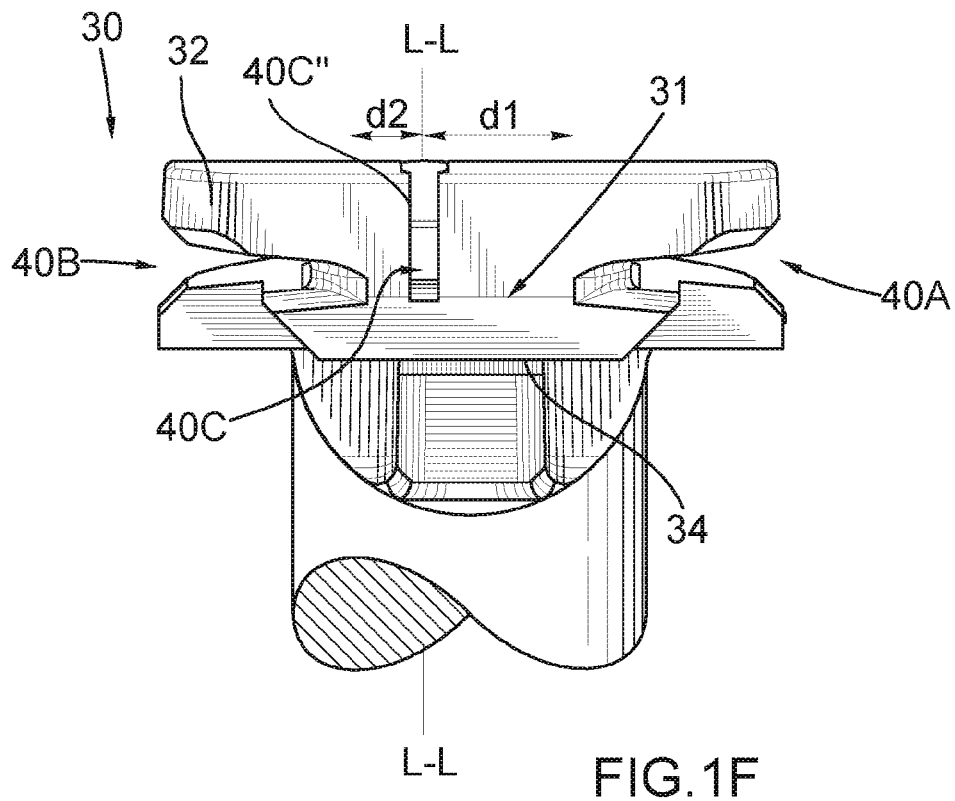
FIGS. 1F-1I, each illustrate a front end view of a distal portion of a knot pusher in accordance with an alternate embodiment of the present invention.

In some embodiments, the intermediate groove 40C may extend along the central support 31 and may be positioned equidistant from the side grooves 40A, 40B forming a central groove 40C' along a central axis C-C of the knot pusher 100A, as shown in FIGS. 1E and 2. The configuration of the intermediate groove 40C facilitates advancement of a sliding knot. In alternate embodiments, the intermediate groove 40C may be transposed laterally along the central support 31 and may be positioned relatively closer to one of the side grooves as compared to the other side groove, as shown in FIG. 1F. In other words, the intermediate groove 40C may extend along a longitudinal axis L-L of the distal head that is parallel to and offset from the central axis C-C, forming an offset groove 40C". For example, as shown in FIG. 1F, the offset groove 40C" is positioned closer to the side groove 40A, when compared to side groove 40B. More specifically, the offset groove 40C" is positioned at a distance d1 from side groove 40A, and at a distance d2 from side groove 40B, where d1 is less than d2. The present configuration of an offset groove 40C" also facilitates advancement of a sliding knot 82.

In one specific example, the central groove or channel 40C, in addition to facilitating advancement or pushing of the sliding knot, functions as a viewing channel to facilitate advancement and tightening of the overhand knot. In other words, the intermediate groove 40C permits viewing of the overhand knot as it is being tightened in order to maintain equal tension on both strands of suture. If unequal tension is applied to the knot it may not remain centered at the tip of the knot pusher and may no longer be visible to the user through the intermediate groove 40C. Thus, the intermediate groove 40C allows the user to maintain visualization of the overhand knot as it is being pushed to ensure that the overhand knot is correctly positioned and is tightened adequately and effectively at the desired target tissue surface. In some embodiments, the intermediate groove 40C allows visualization of the overhand knot to help ensure that it is positioned adjacent and over top of the sliding knot at the desired tissue surface. In some embodiments, at least a proximal portion of the intermediate groove 40C, such as portion 40Cp shown in FIG. 2, has a width that is greater than the width of the suture or suture knot to further enhance visualization of the overhand knot. As shown in FIG. 2, in some such embodiments, the width of the intermediate groove 40C may vary along its length. In further embodiments, in order to facilitate visualization of the sliding and/or overhand knots as well as the placement of the strands of suture into any of the grooves 40A, 40B and 40C, the distal head 30 may be translucent and may comprise a material that is clear or transparent. As such the transparent distal head 30 may enhance the ease of use of the knot pusher 100A and may facilitate advancement and placement of sliding and overhand knots within a desired tissue location within a patient's body. Additionally, the distal head 30 may comprise marking thereon indicating where the strands may be placed and in which order to facilitate advancement of sliding and overhand knots.

Figure 1G:
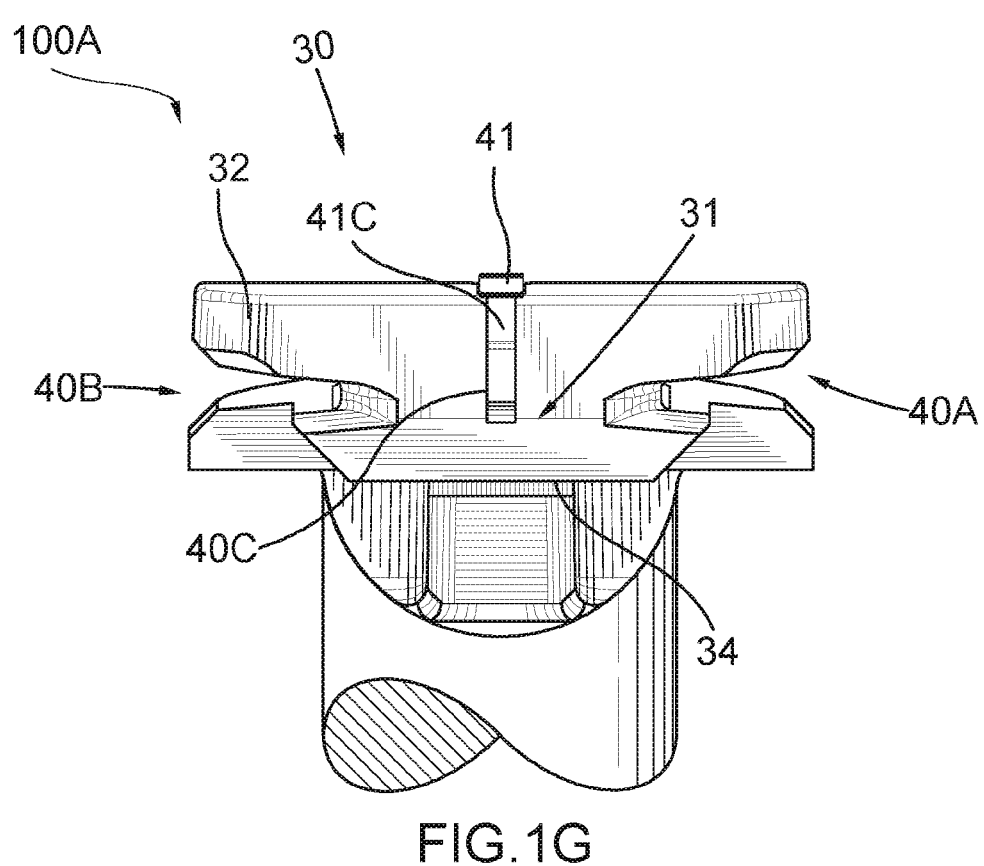

In still another embodiment, as shown in FIG. 1G, the groove 40C may be a covered with a cover or cap 41 that encloses the groove 40C at least partially along its length, forming a tunnel or enclosed groove 41C. In some embodiments, the cap 41 may be formed integrally with the groove 40C. Thus, enclosed groove 41C comprises the intermediate groove 40C and the cap 41 that encloses the intermediate groove 40C. The enclosed groove 41C may allow suture to be threaded there-through to be held therein to prevent detachment of the suture during use as the knot pusher 100A is being advanced to position the sliding knot at the desired target location within tissue within a patient's body. As such the enclosed groove 41C may prevent the suture from sliding out, for example when force is applied against a sliding knot by the distal head 30 when the knot pusher 100A is advanced.

Figure 1H:
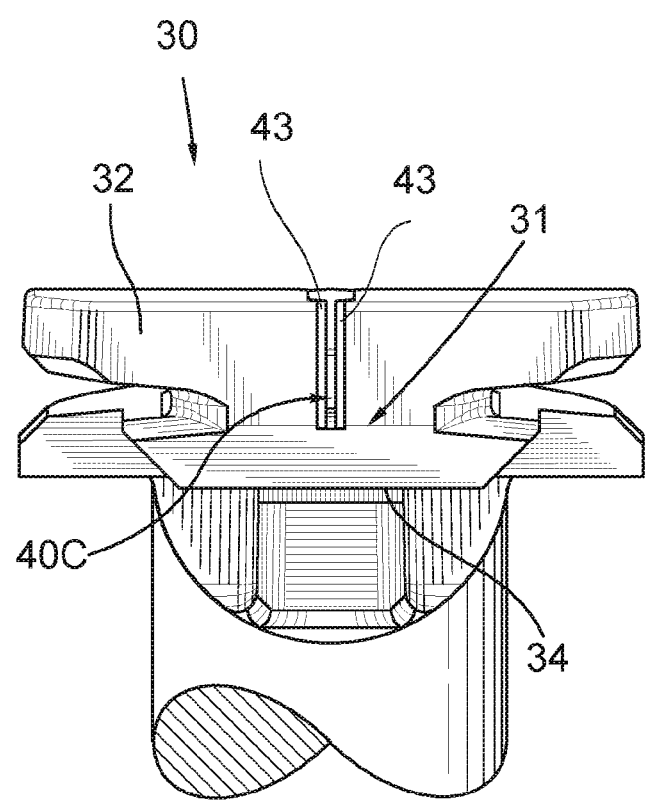

In further embodiments, as illustrated in FIG. 1H, the distal head 30 of the knot pusher 100A may additionally comprise a suture retention feature for retaining the suture within the intermediate groove 40C. For example the intermediate groove 40C may comprise a suture retention feature comprising a suture retaining element that extends at least partially along its length. In one particular example, a resilient material 43 may be positioned within the intermediate groove 40C, for example, on the inside of the intermediate groove 40C, along one or more inner walls of the intermediate groove 40C. In a particular example as shown, the resilient material 43 is positioned on the inside of the intermediate groove 40C along both of the inner walls of the intermediate groove 40C, and effectively narrows a channel formed within the intermediate groove 40C. The resilient material 43 in its nominal position or closed position functions to partially block the opening or passage of the intermediate groove 40C thereby narrowing its width. As the suture is inserted within the intermediate groove 40C, the resilient material flexes from its nominal or closed position to an open position thereby widening the channel within the intermediate groove 40C, to allow a strand of suture to be received within the intermediate groove 40C. Thereafter, the resilient material returns to its nominal or closed position to retain the suture within the intermediate groove 40C.

In alternative embodiments, the intermediate groove 40C may comprise one or more resilient snap arms to retain the suture which may function similarly to snap arms described herein below with respect to the side grooves 40A, 40B. The snap arms may extend inwardly into the intermediate groove 40C. The snap arm may initially block entry of the suture into the intermediate groove 40C but have the ability to flex to allow the suture to be passed into the intermediate groove 40C. After the suture is placed into the intermediate groove 40C, the snaps arms may then return their original position trapping the suture within the channel of the intermediate groove 40C preventing it from slipping out during use.

In still a further embodiment, the intermediate groove 40C could comprise a suture retaining element or component in the form of a moveable cap. For example, cap 41, as discussed previously, could be moveable and operatively coupled in a sliding arrangement with the intermediate groove 40C thereby allowing suture to be inserted in its open configuration and retaining or trapping the suture in a closed configuration. The cap may be closed, for example, by sliding it over the groove 40C. In other embodiments, the suture retaining element may be in the form of a sliding pin that functions to retain the suture in its closed configuration while allowing free passage of the suture into the groove in its open configuration. Still furthermore, in an alternative example, the suture retaining element comprises a latch.

Figure 1I:
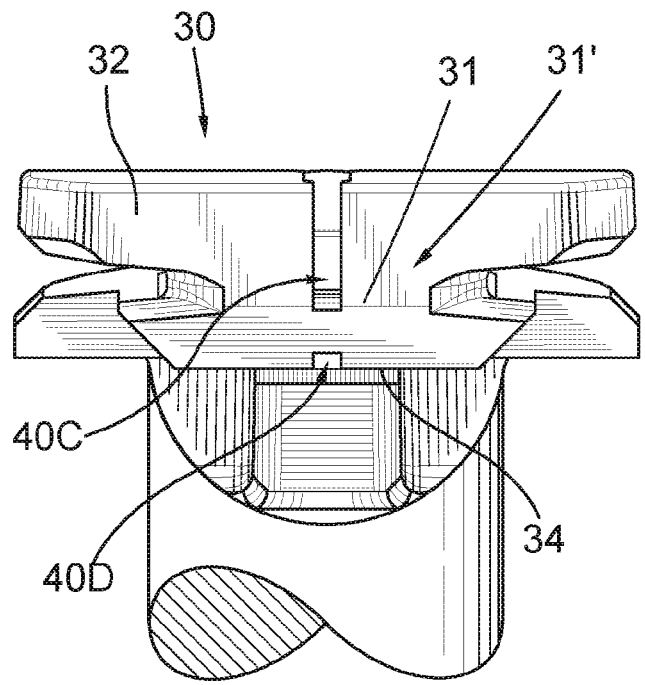
Figure 1J:
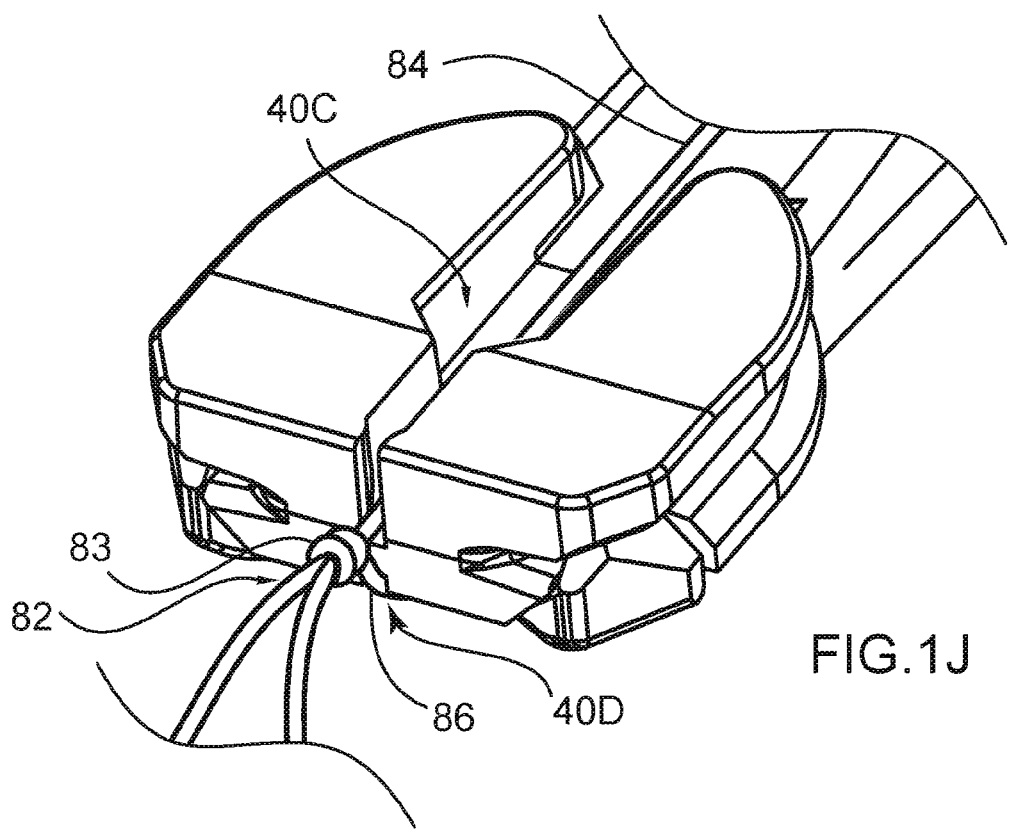
FIG. 1J illustrates a top front perspective view of a distal portion of a knot pusher in accordance with an alternate embodiment of the present invention.

In an additional embodiment of the present invention, the distal head 30 may comprise an additional suture receiving element associated with the bottom wall, i.e. a bottom wall suture receiving element. The bottom wall suture receiving element may be a groove, specifically an opposing groove 40D that is or is not aligned with the intermediate groove 40 but is formed within the bottom wall 34. The opposing groove 40D, as shown in FIG. 1I and FIG. 1J, extends proximally from the knot pushing surface 38 and extends longitudinally along the bottom wall 34 opening into exterior surface of the bottom wall 34. In some embodiments, the opposing groove 40D may be formed within the support 31' such as the central support 31 described above along the bottom wall or face 32. The opposing groove 40D facilitates locking of a sliding knot such as a Dines knot during use by allowing the sliding knot to be held in position against the distal knot pushing surface 38. In other words, the distal head comprises an opposing groove that in one embodiment is aligned with the intermediate groove and formed within the bottom wall, to facilitate tightening of the sliding knot prior to locking of the sliding knot in its tightened configuration. The method of use of a knot pusher 100A with a distal head 30 having an additional opposing groove 40D, is described further herein below with respect to FIGS. 7A-7B and FIG. 1I and FIG. 1J.

Figure 1K:
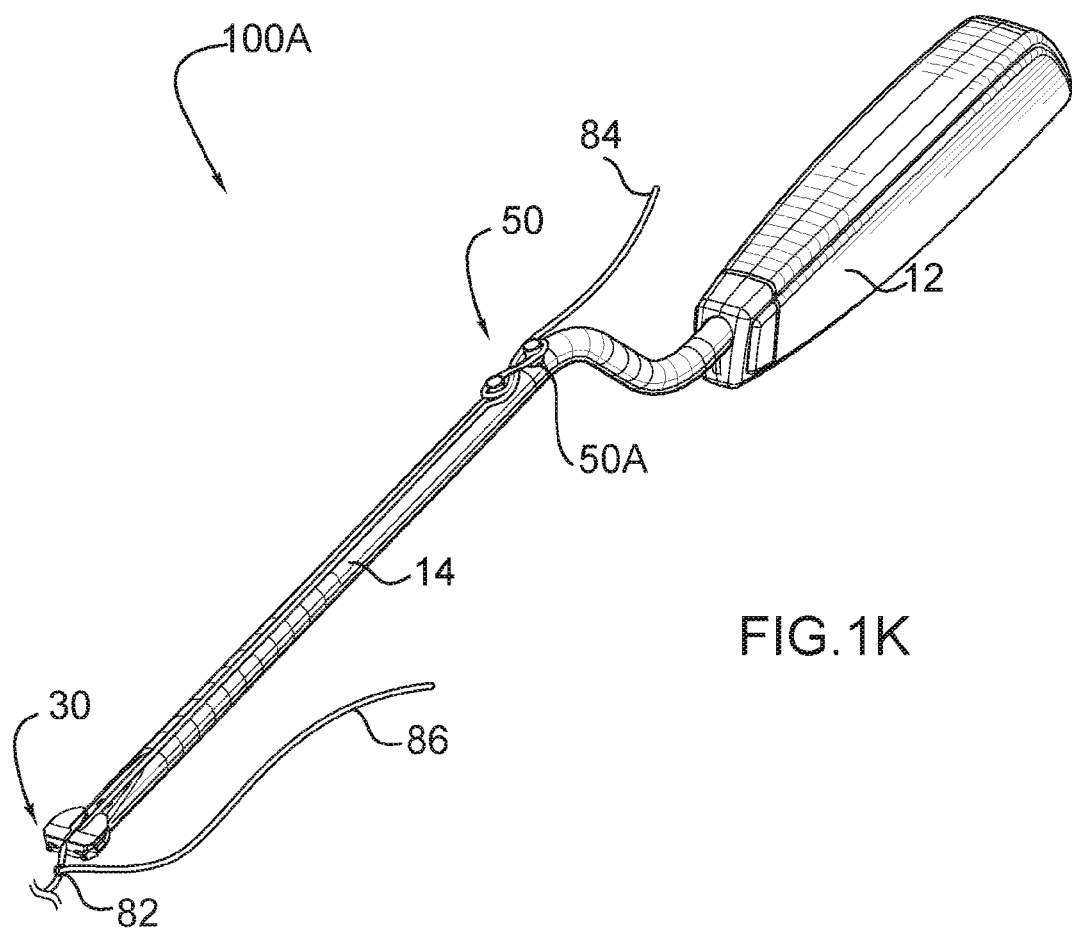
FIG. 1K illustrates a top front perspective view of a knot pusher comprising a tensioning aid in accordance with an embodiment of the present invention.
Figure 1L:
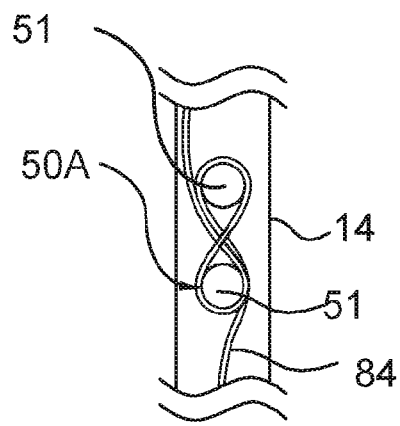
FIGS. 1L-1N, each illustrate top views of a tensioning aid of a knot pusher in accordance with alternate embodiments of the present invention.

In an additional embodiment, as shown in FIG. 1K, the knot pusher 100A additionally comprises a tensioning aid or tension maintaining element 50 that is positioned, for example, along a front or top face of the shaft 14 of the knot pusher 100A. The tensioning aid 50 functions to keep tension on the strand of suture that is held within the intermediate groove 40C (such as within the central groove 40C'). In one specific example, as shown in FIG. 1L, the tensioning aid 50 defines a double-peg configuration 50A, that comprises two pegs 51 that are mounted on the front or top face of the shaft 14. The two pegs 51 allow the strand of suture (which may comprise a post 84, as described later herein), to be wrapped around them. More specifically the strand of suture is routed through the two pegs 51 in a figure eight configuration thereby securing the suture to the shaft 14 of the knot pusher 100A. In other embodiments, the tensioning aid 50 may comprise a configuration having one or more pegs. The method of use of the tensioning aid 50 is described further herein below with reference FIGS. 7A-7E that illustrate the steps of a method of using the knot pusher 100A.

Figure 1M:
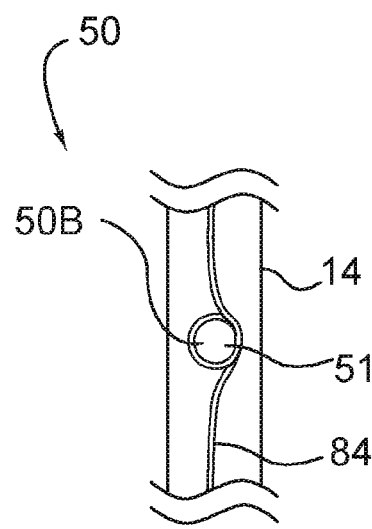
Figure 1N:
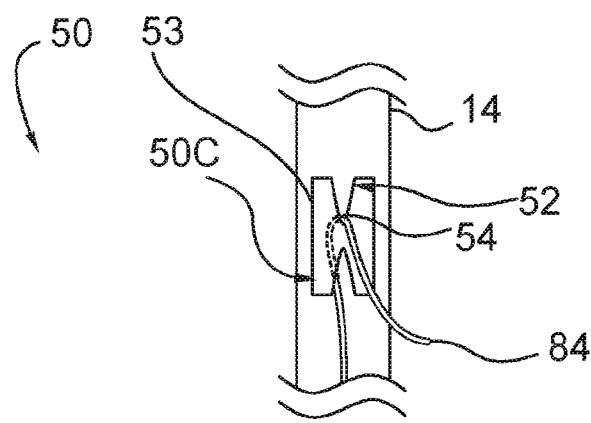

In an alternate configuration as shown in FIG. 1M, the tensioning aid 50 comprises a single-peg configuration 50B. The post 84 may be wound around the peg 51 to be secured to the shaft 14. In a still further alternative, as shown in FIG. 1N, the tensioning aid 50 comprises a catch or clip 50c that comprises a main body 53 that is mounted on the shaft 14. For example, the main body 53 may be coupled to the shaft 14 via a protrusion. The main body 53 is spaced apart from the shaft 14 such that a gap is present between the main body and the shaft 14, to allow the post 84 to be routed through the gap. The main body further comprises at least one slit or opening 52 formed therein that defines two arms 53a and 53b for retaining the one of the two strands of suture there-between to secure said one of the two strands of suture to the shaft. In some examples, the opening 52 narrows at its base in the proximal direction forming an apex 54 which functions to pinch the strand of suture after it is passed behind the main body 53 and then through the opening 52 such that it passes in front of the main body 53 thereafter allowing the post 84 to be pinched at the apex 54.

Figure 4A:
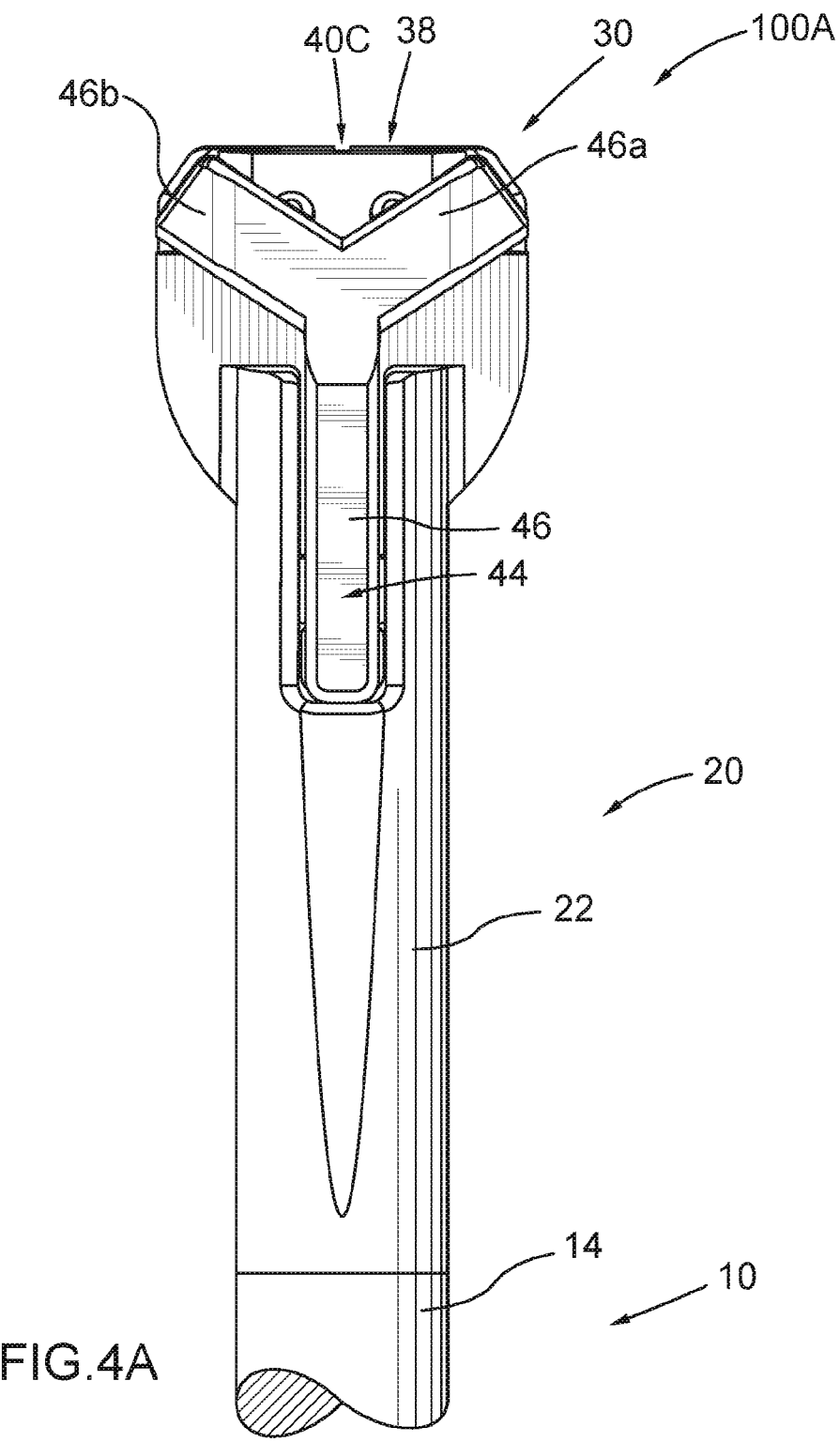
FIG. 4A illustrates a bottom view of a distal portion of a knot pusher in accordance with an embodiment of the present invention.
Figure 4B:
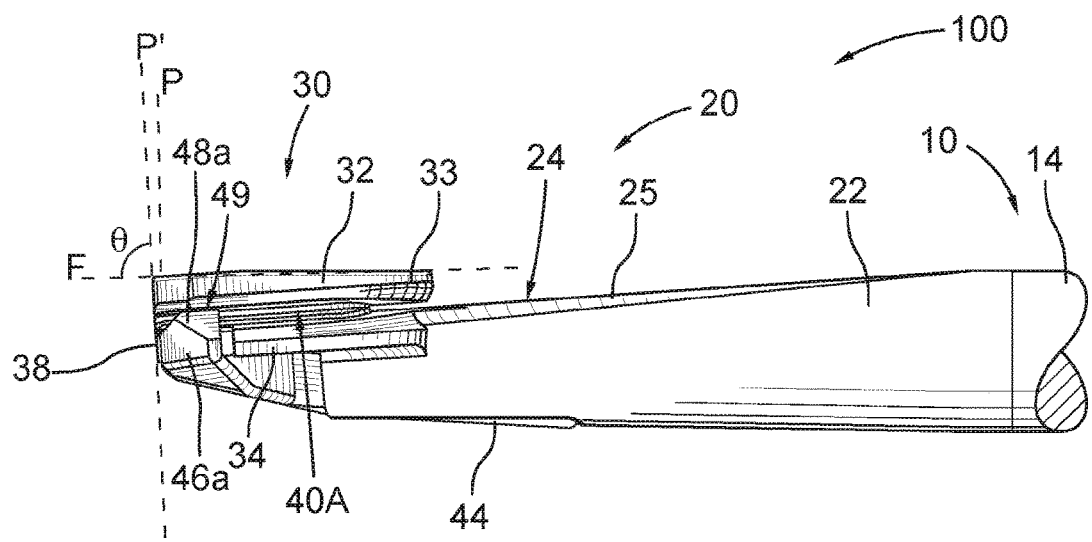
FIG. 4B illustrates a right side view of a distal portion of a knot pusher in accordance with an embodiment of the present invention.
Figure 4C:
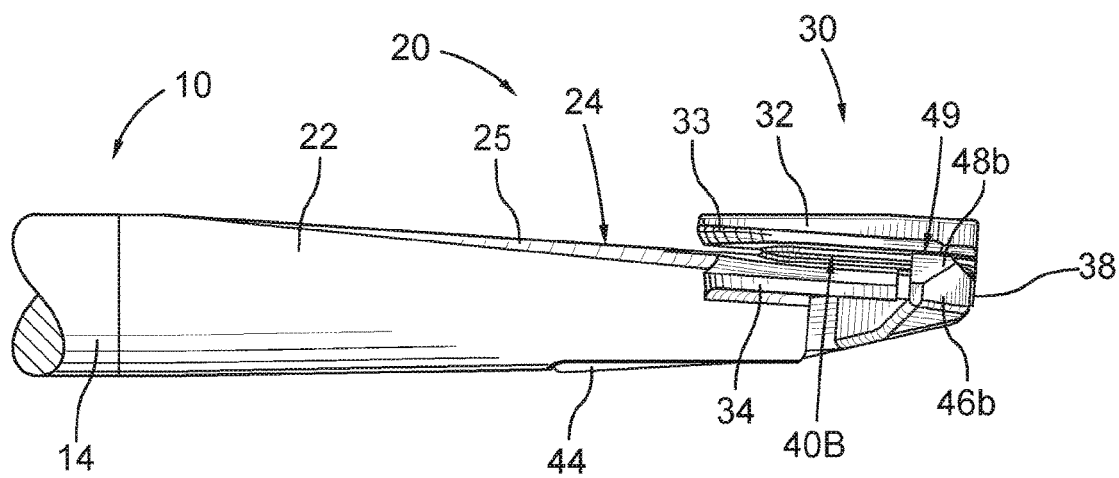
FIG. 4C illustrates a left side view of a distal portion of a knot pusher in accordance with an embodiment of the present invention.
Figure 4D:
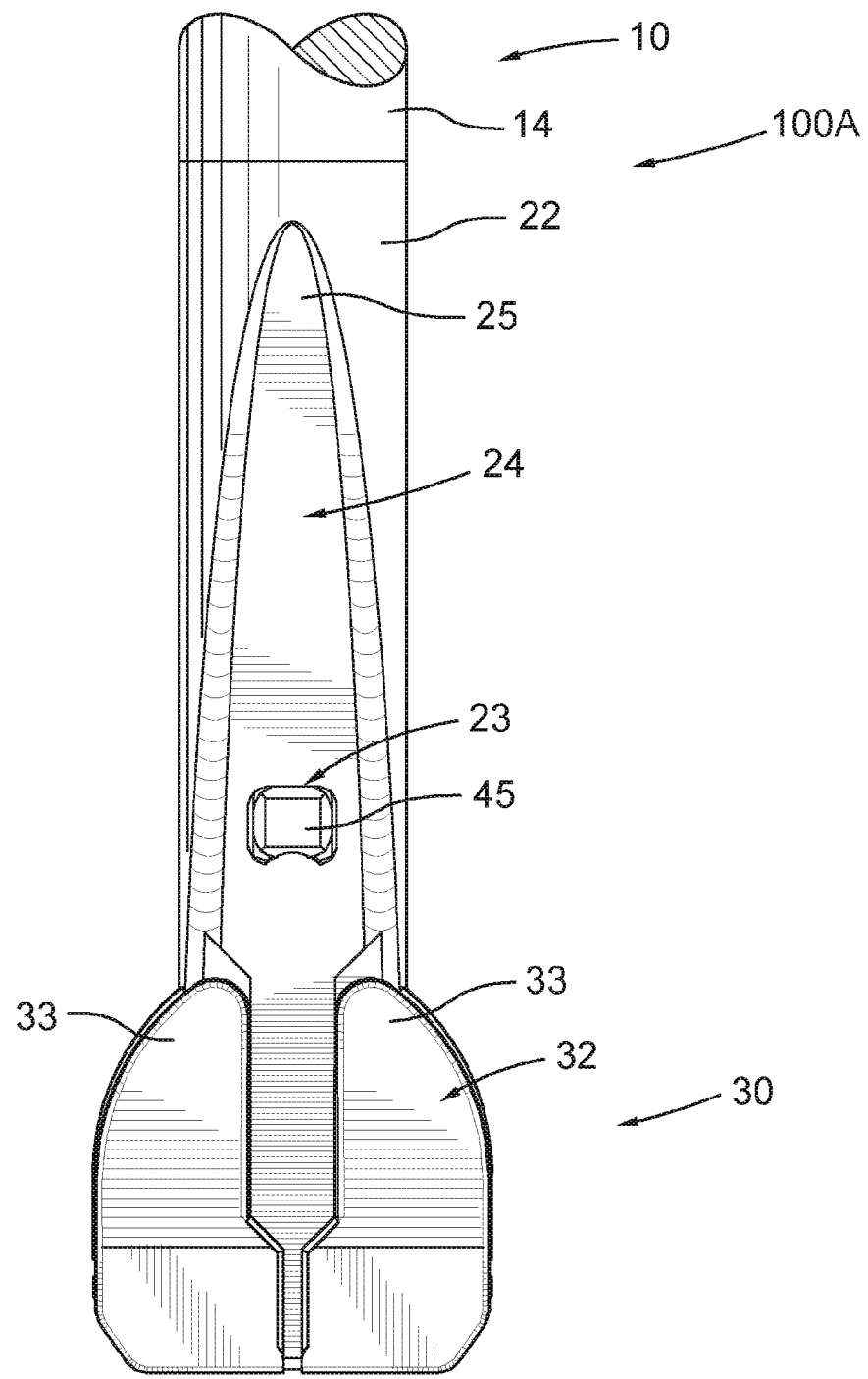
FIG. 4D illustrates a top view of a distal portion of a knot pusher in accordance with an embodiment of the present invention.

In some embodiments, as shown in FIGS. 4A, 4B, and 4C, the distal head 30 may additionally comprise a side groove suture retention feature such as a side groove suture retaining element that is associated with one or more of the side grooves 40A, 40B. In some embodiments, the suture retention feature for the side grooves 40A, 40B may be similar to the suture retention feature described herein previously with respect to the intermediate groove 40C. In one particular example, the side groove suture retaining element comprises a snap arm 44 that is coupled to the neck 22, for example via a force fit or snap fit arrangement. The snap arm 44 comprises snaps 46a and 46b that extend radially from a longitudinally extending stem 46. In one specific example, further shown in FIG. 1B and FIG. 2, a tab 45 of the snap arm is received within an opening 23 within the neck 22 and engages therewith. In the illustrated embodiment, the snaps 46a and 46b each form a portion of bottom wall 34. In some embodiments, the snap arm 44 is resilient allowing the snaps 46a and 46b to flex from their nominal or closed position to an open position to allow the two ends of the suture to be received within the opposed side grooves 40A and 40B. Thereafter the snaps 46a and 46b return to their nominal or closed position to retain the two suture ends in each of said side grooves 40A and 40B.

In one specific example, as shown in FIGS. 4B and 4C, each of the snaps 46a and 46b comprise a projection 48a, 48b respectively that projects away from the bottom wall 34 towards the top wall 32, such that there is a minimal clearance or gap 49 between the walls, substantially preventing the suture from exiting the side grooves 40A, 40B. In some embodiments, when the snaps 46a, 46b are in the closed position, the clearance or gap 49 is smaller than the outer diameter or width of the suture to retain/constrain the suture within the side grooves 40A, 40B and prevent the suture from passing through the gap 49 during the process of pushing the knot. Additionally, the snaps reduce the risk of the suture strands falling out of position from within the side grooves 40A and 40B when tension is not maintained on the suture strands. This helps to minimize the risk of suture strands exiting the side grooves 40A, 40B during the procedure and thus helps to minimize the need to reinsert the suture strands within the side grooves 40A and 40B as the knot pusher is being advanced distally to push the knot. In some embodiments, the pair of snaps 46a and 46b comprise hinged snaps that act to constrain or lock the strands of suture within the side grooves 40A, 40B. The side grooves 40A, 40B are of a sufficient depth to retain the suture. In some embodiments, the snaps 46a and 46b are chamfered to facilitate the loading of the suture within the side grooves 40A, 40B.

In some embodiments, the neck 22 comprises a tapered portion 24 along a top face thereof that leads into the opposed side grooves 40A and 40B, as shown in FIGS. 4B and 4C. The neck 22 tapers into the opposed side grooves 40A and 40B such that the top face of the neck 22 is flush with the inner surface of the bottom wall 34. As each of the opposed side grooves 40A and 40B are formed contiguously with the tapered portion 24, it allows the two strands of suture to be guided/lead into the side grooves 40A, 40B. In other words, the tapered portion 24 is continuous with the side grooves 40A and 40B. This may allow for easier loading of the suture strands within the knot pusher 100A to facilitate the knot pushing procedure. In some embodiments, the tapered portion 24 comprises a flat planar surface 25.

In some embodiments, each of the side grooves 40A and 40B defines a curve, or alternatively, extends radially away from a central axis of the distal head 30. The curved side grooves 40A and 40B extend proximally from the distal knot pushing surface 38 towards the neck 22. In some embodiments, a part of the top wall 32 that extends proximally from the central support 31, forms overhangs 33, as shown in FIG. 4B. A portion of each of the side grooves 40A, 40B is formed between an overhang 33 and the neck 22. The overhangs 33 function as hooks to facilitate capturing of the suture by the distal head 30. Using the hooks, the two strands of suture may easily be guided into the side grooves 40A, 40B to allow for easier loading of the suture into the knot pusher 100A.

With reference now to FIG. 4B, in some embodiments the knot pusher 100A may comprise additional features to facilitate loading of the suture and/or pushing of the knot. In some such embodiments (not illustrated), the knot pushing surface 38 may be defined (or may extend) along a plane P that is perpendicular to the longitudinal axis (along plane F) of the knot pusher. In other embodiments (as illustrated), the knot pushing surface 38 defines a taper such that the knot pushing surface 38 is at an incline relative to plane P. In some embodiments, a plane P' of the knot pushing surface 38 is at an angle θ (with respect to the top face 32 defined by plane F) which is less than about 90 degrees (or, put differently, the plane P' is oriented at an angle [180-θ] that is greater than about 90 degrees from the longitudinal axis of the knot pusher 100). In a specific example, the angle θ between the knot pushing surface 38 and the top face 32 is about 89 degrees. The incline of the knot pushing surface 38 helps to retain the knot away from the opening of the intermediate groove 40C (see FIG. 2). The distal knot pushing surface 38 of the knot pusher is angled away from the perpendicular such that as the knot is pushed and tightened, a component of the longitudinally directed force acts to direct the knot (down and) away from the opening of the intermediate groove 40C. The inclined knot pushing surface 38 may help prevent a knot such as a sliding knot from disengaging from the knot pusher 100A to prevent patient injury or to avoid the requirement of re-engagement of the knot with the knot pusher 100A.

As shown in FIG. 1A, the knot pusher may have a length 1. In some embodiments, length 1 may be equal to between about 3.00" (inches) to about 20.00". In one specific example, the knot pusher 100A has a length 1 that is equal to about 11.09". As noted previously, the knot pusher 100A comprises a distal portion 20 that is coupled to the shaft 14 of the proximal portion 10. As shown in FIG. 1D, the distal portion 20 may have a length Y. In some embodiments, length Y of the distal portion 20 may be equal to greater than about 0.10". In one such example, the distal portion 20 may form a significant portion or majority of the device that extends distally beyond the handle 12. As illustrated in FIG. 1D, in one specific example, the distal portion 20 has a length Y equal to about 1.00". Furthermore, the shaft 14 and the distal portion 20 may have a combined length S of about 2.00" to about 19.00", for example about 7.35". Additionally, the shaft 14 may have a width $S_w$ of between about 0.10" to about 1.00" and more specifically, from about 0.10" to about 0.50". In one specific example, the shaft 14 has a width, $S_w$, of about 0.20".

As discussed previously, the shaft 14 is coupled to the distal portion 20; the distal portion 20 further comprising a distal head 30. As shown in FIG. 1E, the width of the distal head is defined by U. In some embodiments, the distal head 30 may have a width U of between about 0.10" to about 1.00" and more specifically, from between about 0.10" to about 0.50". In one specific example, the distal head 30 has a width U equal to about 0.33".

In some embodiments, the length of the side grooves 40A, 40B may be substantially equal to the length of the top and bottom walls 32, 34. In one specific example, as shown in FIG. 1D, the top and bottom walls 32, 34 have lengths Z, W that are equal to about 0.33" and 0.32", respectively. Furthermore, the two opposed side grooves extend from the distal knot pushing surface 38 by a length that is equal to about 0.33". In some embodiments, the length of the distal head 30 and each of the side grooves 40A and 40B may range from between about 0.10" to about 1.00", and more specifically, from between about 0.10" to about 0.50". In other embodiments, the length of the distal head 30 may be greater than about 1.00".

As noted previously, the distance between the side grooves 40A and 40B may be defined by the width of the central support 31. In some specific embodiments, the distance between the side grooves may be equal to or greater than about three times the width/diameter (these terms being used interchangeably herein) of the suture to be used. In one specific example, the spacing between the side grooves 40A, 40B, and thus the width of the central support 31 is about 0.012" where the width of the suture to be used is about 0.004". Thus, the spacing between the side grooves may correspond (i.e. be proportional) to the size of the suture being used. In some embodiments, the spacing between the side grooves may correspond to a suture of up to a size 5; that is, in these embodiments, the spacing between the side grooves may be up to about three times the width of a 'size 5' suture, depending on the suture intended to be used with the device. In other embodiments, the side grooves 40A, 40B may be spaced apart by a distance of between about 5 times the width of the suture to about 70 times the width of the suture. In one specific embodiment, the side grooves 40A and 40B are spaced apart by a distance of about 10 times the width of the suture being used. In one such device as shown in FIG. 1E, which may be used, for example, with a 2-0 suture, the width X of the central support 31 and thus the distance between the side grooves 40A, 40B, is equal to about 0.11" which is equal to about 10 times the width of a 2-0 suture.

In some embodiments, the distance between the side grooves 40A, 40B may correlate with the actual width of each of the side grooves 40A, 40B, rather than being proportional to the width of the suture to be used. With reference again to FIG. 1E, the distance between the side grooves 40A, 40B (i.e. the width X of central support 31) is approximately equivalent to the width U of the distal head 30 subtracted by the widths of the side grooves 40A, 40B. In a particular example of this, the width of the central support 31 is about 0.11" which is equal to the width of each of the two side grooves 40A and 40B. In some embodiments, the distance between the side grooves may correspond to between about 5 times to about 70 times the width of the side grooves 40A, 40B. In some such embodiments, the width of each of the side grooves is equal to the width of suture to be used.

Referring now to FIG. 1D, the central support 31 of the distal head 30 defines a length V that is less than the total length W of the distal head 30, allowing an overhang 33 to be formed as a result. More specifically, the proximal portion of each of the side grooves 40A and 40B may be defined by overhangs 33 formed by proximal portions of the top wall 32 that extend proximally from the central support 31. The overhangs may have a length that is roughly equal to the length W of the distal head 30 subtracting the length V of the support 31. In one specific example, the central support 31 has a length V of about 0.250" and the overhangs 33 each have a corresponding length of about 0.076", i.e. the proximal portion of each of the side grooves 40A and 40B has a length of about 0.076".

Referring again to FIG. 2, at least a portion of the intermediate groove 40C, such as the distal portion 40Cd, may have a width that is substantially equal to the width of the suture being used. More specifically, the distal portion 40Cd of the intermediate groove 40C is dimensioned such that it is sufficiently wide so as to allow a suture to be positioned there-through. In some embodiments the distal portion 40Cd may have a width that is between about 1 times the suture width to about 3 times the suture width. Limiting the width of the intermediate groove may aid in preventing a knot positioned at the distal knot pushing surface 38 from being pulled into the intermediate groove 40C. In some embodiments, the width of the intermediate groove distal portion 40Cd may range from about 0.012" to about 0.042". In one specific example, as shown in FIG. 1E, the distal portion of the intermediate groove 40C has a width X' of about 0.025" for use with a suture of 0.011" width. In another example, for use with a suture having a suture width of about 0.004", the intermediate groove distal portion 40Cd has a width of about 0.012".

In some embodiments, the width of proximal portion 40Cp of the intermediate groove 40C is substantially equivalent to the width of distal portion 40Cd. In alternate embodiments, the width of central groove 40C along proximal portion 40Cp is greater than the width along distal portion 40Cd. In some such embodiments, the width of proximal portion 40Cp is slightly less than the total distance between the side grooves 40A, 40B.

In some embodiments, as illustrated for example in FIG. 1A, the distal head 30 of the knot pusher may be offset from the handle 12, to enhance visualization and line of sight for the distal head 30 during the procedure. In other words, the longitudinal axis of the distal head differs from/is offset from the longitudinal axis of the handle, i.e. the distal head may be misaligned or planarly offset (although the respective planes defined by the handle and distal head may be parallel to one another, as shown) relative to the handle. This helps to prevent the physician's hand from blocking the distal head 30 from view. In some embodiments, the distal head 30 may be offset from the handle 12 by between about 1.0" to about 4.0". In a specific example of an embodiment where the distal portion 20 is transversally offset from the handle 12, the top surface of the top wall 32 is offset from a bottom surface of the handle 12 by about 1.74". In still other embodiments, the handle 12 may not be offset from the distal head 30 and may be coaxially aligned with the distal head 30.

In some embodiments, the handle 12 may have a width ranging from about 0.5" to about 1.0" and a length of about 1.0" to about 5.0". In one specific example, the handle 12 has a width $h_w$ of about 0.56" and a length of about 3.74". In another example, the handle 12 may be sized, configured and shaped to define an ergonomic pen-like grip. Thus, in accordance with some embodiments of the present invention, the handle has an ergonomic shape that allows the handle to be held comfortably and easily. In some embodiments, portions of handle 12 may be coated/covered/overlaid with a material suitable for gripping/grasping and manipulating the knot pusher. For example, handle 12 may include ergonomic side grips on one or more sides of the handle, the side grips comprising a thermoplastic elastomer such as Santoprene®. In alternative embodiments, other materials may be used. The aforementioned dimensions have been found to be particularly well-suited for a knot pusher used for the closure of defects in the annulus fibrosus of an intervertebral disc, as well as for other similar applications.

Figure 5B:
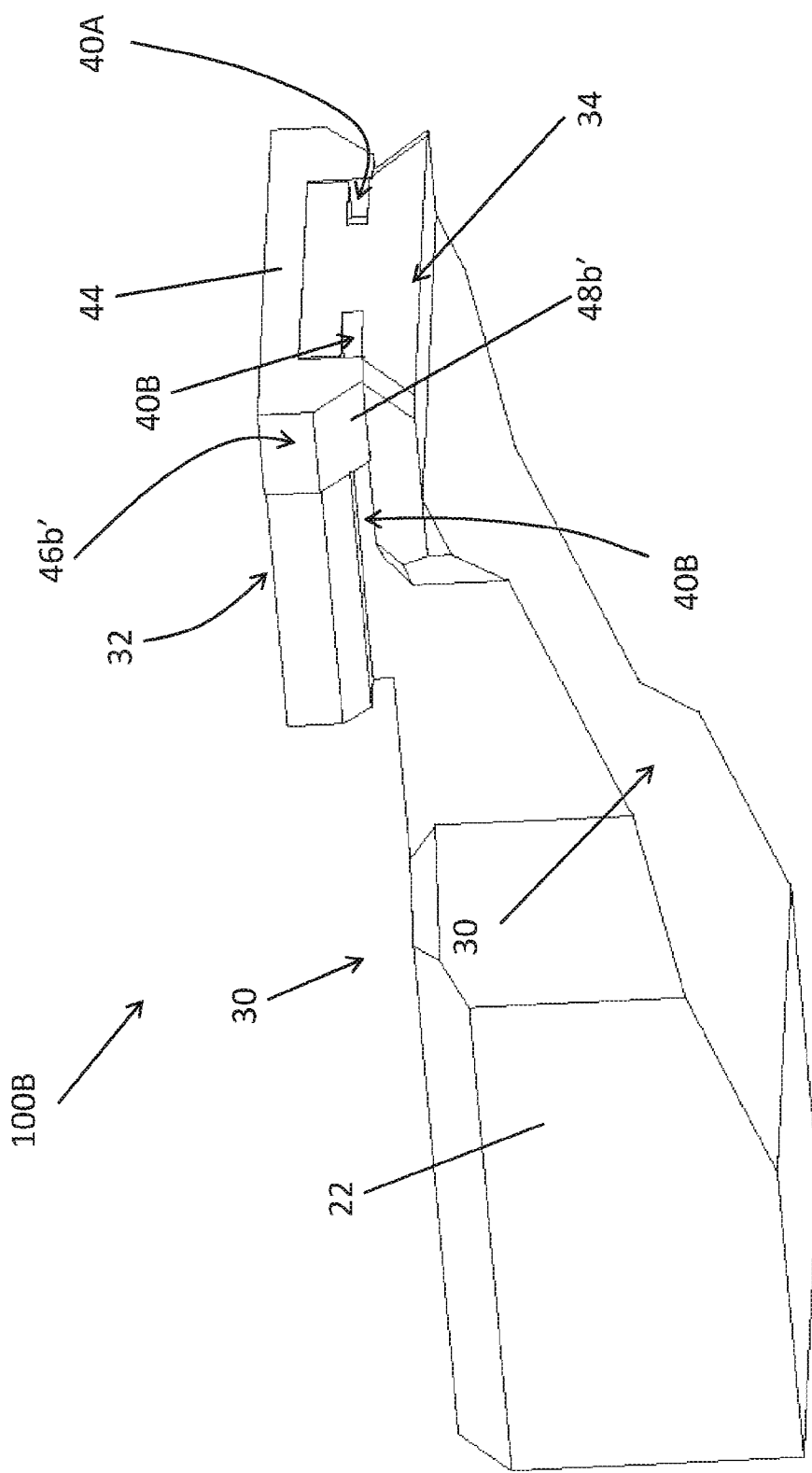

In an alternative embodiment, as shown in FIGS. 5A-5B, a knot pusher 100B comprises a snap arm 44' that may be coupled to a top surface of the shaft 14 or neck 22. The snaps 46a' and 46b' form a portion of the top face 32 of the knot pusher 100B. The snaps 46a', 46b' function in a similar manner to snaps 46a and 46b to retain the suture within side grooves 40A and 40B to prevent the suture from disengaging from the distal head 30 of the knot pusher when tension is released. The snaps 46a' and 46b' comprise downwardly extending projections 48a', 48b' that extend towards the opposing wall which in this example comprises the bottom wall 34 so that the suture is retained there-between. The embodiment shown in FIGS. 5A-5B may additionally comprise an intermediate groove 40C (not shown) for allowing advancement of a sliding knot.

Figure 6A:
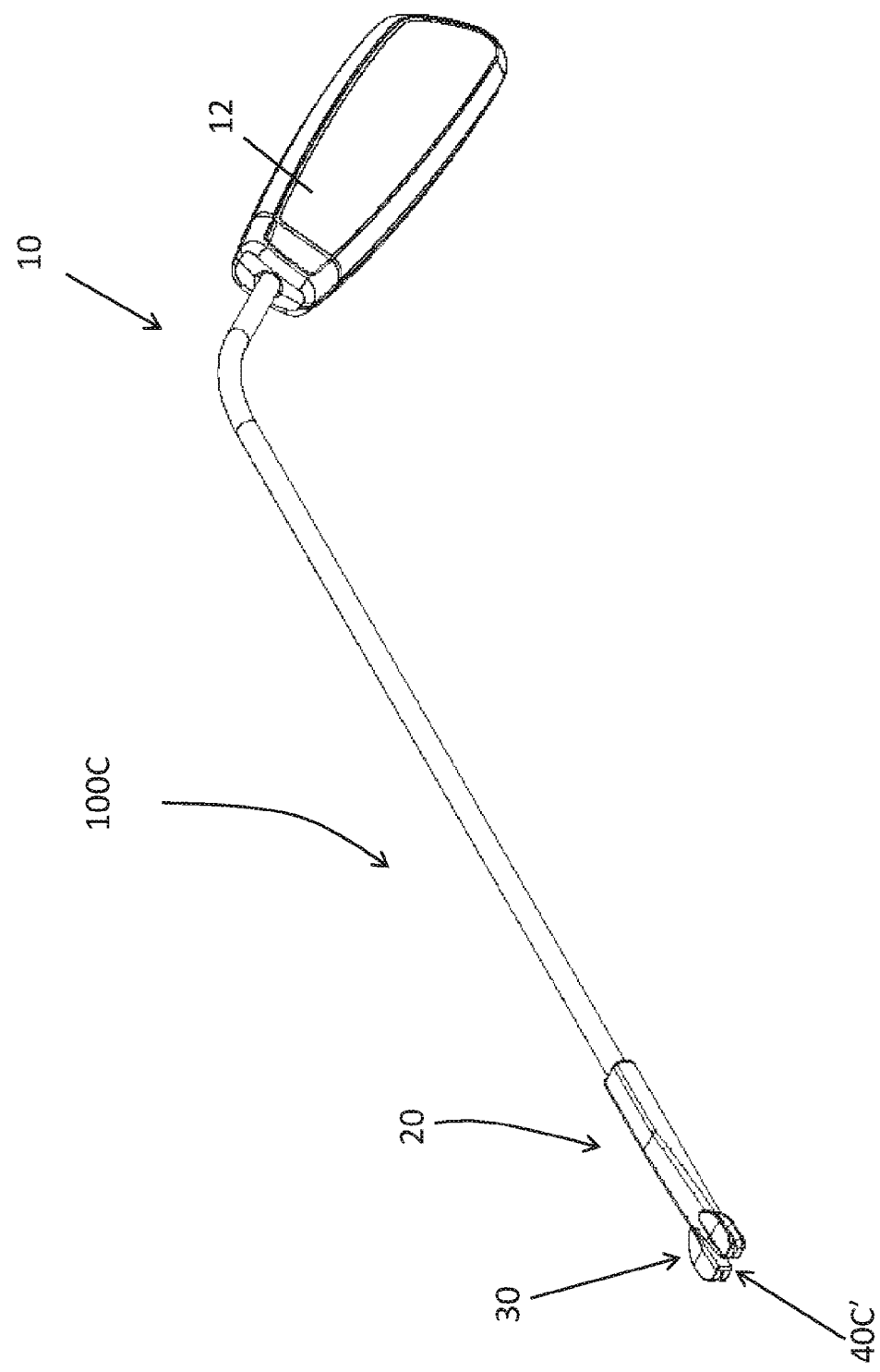
FIGS. 6A-6C illustrate a still further alternative embodiment of a knot pusher in accordance with the present invention.
Figure 6B:
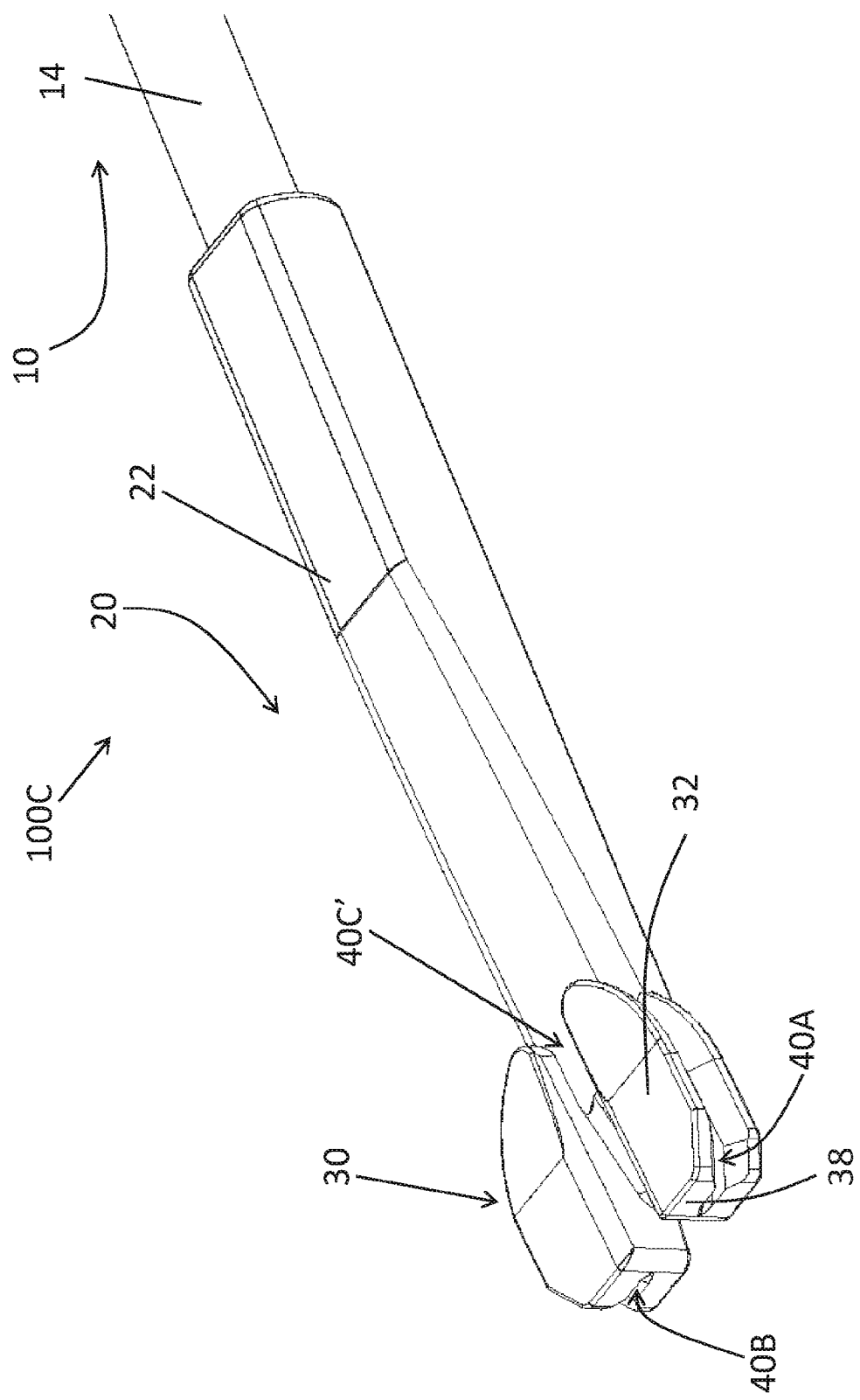
Figure 6C:
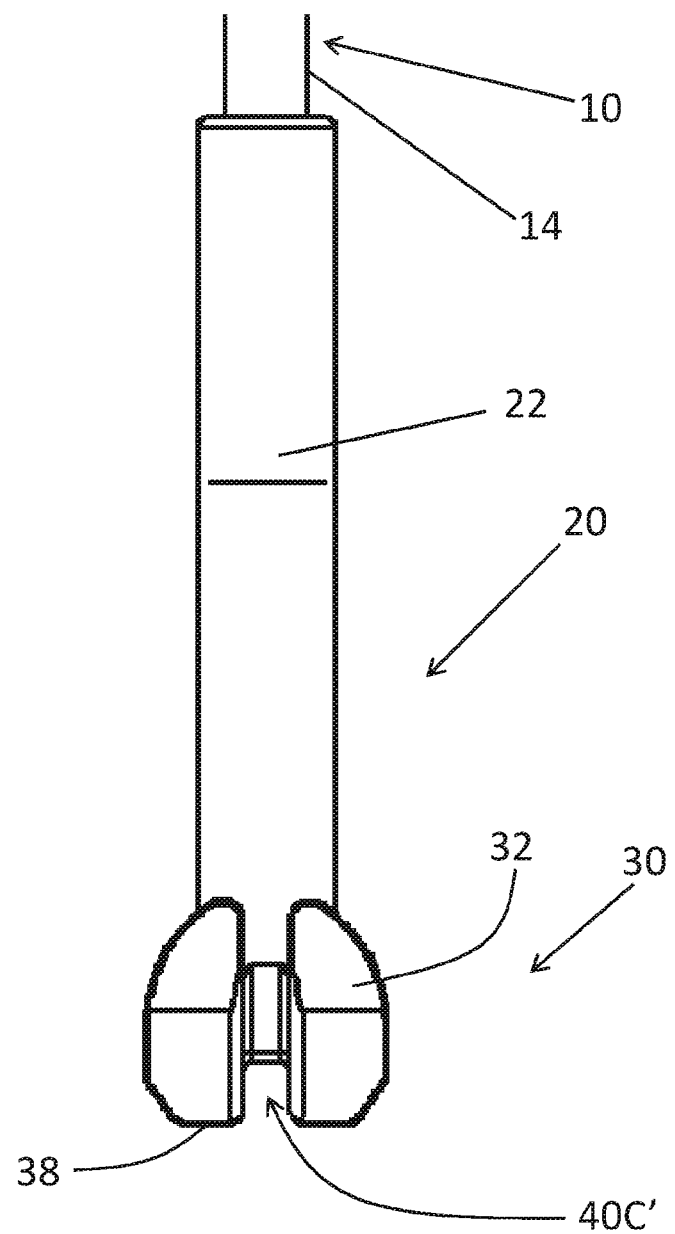

In a further alternative embodiment, as shown in FIGS. 6A-6C, a knot pusher is disclosed having a central viewing channel. The knot pusher 100C comprises a proximal portion 10 comprising a handle 12 and a shaft 14. The knot pusher 100C further comprises a distal portion 20 comprising a neck 22 and a distal head 30 with the distal head defining side grooves 40A and 40B between top and bottom walls 32, 34 (34 not shown in Figures but is on the bottom/underside surface of knot pusher 100C). The distal head defines a central channel or groove 40C' that extends longitudinally through the top face 32 of distal head 30. The intermediate groove or channel 40C' extending from the proximal part of the distal head 30 through to the knot pushing surface 38. The intermediate groove 40C' acts a viewing channel to permit viewing of the overhand knot to facilitate tightening of the overhand knot.

With reference to FIG. 6A, an alternative embodiment of an offset shaft is illustrated. In this particular embodiment, the shaft is curved so as to define a non-parallel longitudinal axis relative to the handle 12.

As discussed previously, in some medical applications it is desirable to apply one or more knots in order to approximate tissue and to secure the suture that has been passed through a region of tissue. For example, one or more knots may be applied to suture that has been passed through a region of tissue having a defect in order to: (a) aid in approximating the tissue; and (b) secure the suture around the defect. Some such applications require the use of both sliding and overhand knots, which knots have differing mechanisms for advancing to the tissue site as well as for tightening at the tissue site. In applications where the tissue site being treated is remote or where the access to the tissue site is limited for any other reason, it may be desirable to use a knot pusher to advance and/or tighten the knot(s). Thus, in such applications where access to the tissue being sutured is restricted and where both types of knots are desired/required to complete the procedure, it would be beneficial for the user to be able to utilize the same device for advancing and tightening both forms of knots.

In some such applications, a sliding knot is advanced to the tissue site in order to treat the defect within the region of tissue while one more half-hitches or other types of overhand knots may be subsequently applied in order to secure the sliding knot in place. These additional knots help to ensure that the sliding knot does not open or unravel following the procedure.

In accordance with an embodiment of such a procedure, a method of using a knot pusher such as described herein above is disclosed for advancing/pushing both a sliding knot and an overhand knot during the course of the procedure. In one particular example of this embodiment, the tissue site may comprise a region of tissue defining a defect, for example within an annulus fibrosis of an intervertebral disc. In one such example, access to the intervertebral disc may be provided through a surgical portal, inserted for example through a lamina of a vertebra, to allow the suture to be passed through the affected disc tissue.

Following passage of a suture loop around the defect, for example as disclosed in U.S. provisional patent application serial number 61/597,449, filed on Feb. 10, 2012 and incorporated herein by reference in its entirety, a sliding knot may be deployed to secure the suture. The knot pusher is used to advance the sliding knot along the suture through the portal to enable approximation of the tissue at the defect and further to tighten and lock the sliding knot. In order to secure the sliding knot at the surface of the disc, one or more additional half-hitches or other overhand knots are applied over the sliding knot.

Figure 7A:
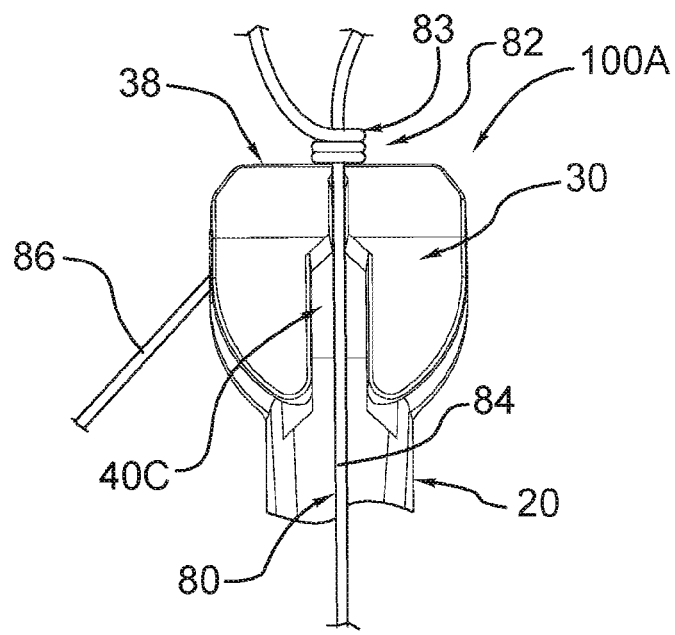
FIGS. 7A-7E illustrate a method of using a knot pusher in accordance with an embodiment of the present invention.
Figure 7B:
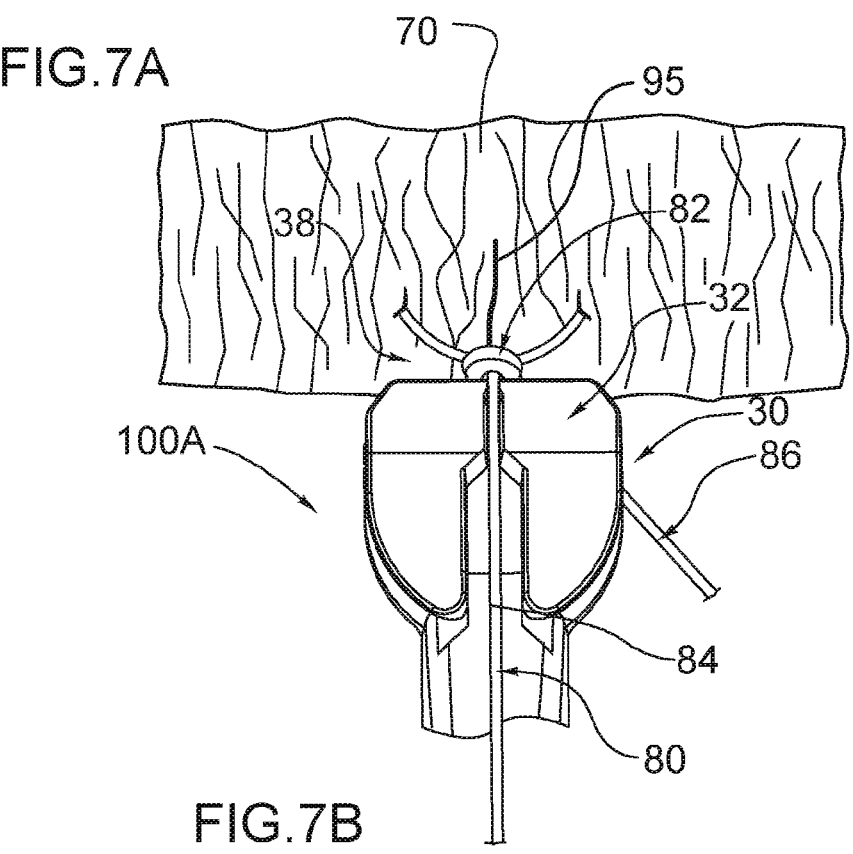

The sliding knot may be formed after the suture has been passed through the disc or may be a pre-formed or pre-tied knot that is deployed thereafter. As shown in FIGS. 7A-7B, the sliding knot 82 terminates in two strands of suture with one strand being defined as a post 84 and the second strand of suture being defined as a locker 86, which terms are known to those of skill in the art.

The following discussion references FIGS. 7A-7E. In one specific example of a method of the present invention, the sliding knot 82 comprises a Dines knot 83. As shown in FIG. 7A, the post 84 is placed within the intermediate groove 40C—specifically the central groove 40C' with the sliding knot 82 resting against the distal knot pushing surface 38. The knot pusher or device 100A is then advanced towards the tissue site, for example through a portal allowing the distal head 30 to push or advance the sliding knot 82 by pushing directly on the sliding knot 82. Tension is maintained on post 84 as the knot pusher 100A is advanced. A longitudinally directed force is applied against the sliding knot 82 by the distal knot pushing surface 38, such that it slides along the post 84 distally (for example through the portal) until it is positioned at the tissue surface 70 having a defect 95 as shown in FIG. 7B, where the tissue may be, for example, an annulus fibrosis of an intervertebral disc. A proximal 'pulling' force is applied to the post 84 to maintain it in tension as the sliding knot 82 is advanced in order to approximate the tissue.

Furthermore, in embodiments where the knot pushing surface 38 is inclined—for example, as shown in FIG. 4b—the incline allows a component of the longitudinally directed force to direct the sliding knot 82 away from the opening of the central groove 40C'. This enables the sliding knot 82 to remain engaged with the knot pushing surface 38 as the knot pusher 100A is advanced to further aid in tightening the sliding knot 82.

In one specific embodiment, where the sliding knot 82 is a Dines knot 83, continuous tension is applied using the knot pusher 100A to approximate the defect. In other embodiments, the knot pusher 100A may be pushed against the sliding knot 82 at the tissue surface and released. This may be repeated (i.e. the act of pushing and retracting) a plurality of times in order to further tighten the sliding knot 82. In such an embodiment, the knot pusher 100A may be pushed and released four times until the sliding knot is fully cinched. At this step, a determination is made as to whether tissue approximation at the defect 95 is adequate. If the tissue approximation is not deemed to be sufficient, the step of pushing and releasing the knot pusher 100A may be repeated further.

Once the tissue has been approximated to the extent desired, tension is maintained along the post 84 whilst the locker 86 is pulled to lock that position of the Dines knot, i.e. the locker 86 is pulled until the sliding knot 82—which in this particular case comprises the Dines knot 83—reconfigures. This locks the Dines knot 83. In some embodiments, the locker 86 may be pulled and released more than once in order to ensure complete locking of the Dines knot 83. In one specific example, the locker 86 may be pulled and released four times. The knot pusher 100A may then be withdrawn through the portal.

In one particular example, as shown in FIG. 1J, the distal head 30 comprises an intermediate groove 40C as well as an opposing groove 40D. In one such embodiment the intermediate groove comprises a central groove 40C'. In accordance with a method of the present invention, the post 84 of the suture is placed or received within the central groove 40C and pulled to hold the sliding knot 82 such as the Dines knot 83 in place against the distal knot pushing surface 38, similar to the discussion above with reference to FIGS. 7A and 7B. The locker is then pulled underneath the distal head 30 along the bottom wall 34 to be placed or received within the opposing groove 40 and held therein. When the post 84 and the locker 86 are held in this orientation, it allows the post 84 to be pulled with sufficient force to optimize the tension placed on the Dines knot 83. This allows the Dines knot to be tightened sufficiently to ensure effective approximation of the tissue. The post 84 is kept taut and in tension such that force is maintained against the Dines knot 83 until the locker is pulled, thus locking the Dines knot 83 in its tightened configuration. Therefore, the opposing groove 40D allows the sliding knot 82 to be held in position against the distal knot pushing surface 38 to optimize tightening and locking of a 'sliding and locking knot' such as the Dines knot 83.

In some embodiments, to facilitate tightening and locking of the sliding knot 82 such as the Dines knot 83, the knot pusher 100A may additionally comprises a tensioning aid 50 as discussed previously and shown in FIGS. 1K-1N. The tensioning aid 50 maintains tension on the post 84 during use. After the knot pusher 100A has been advanced into the tissue to position a sliding knot 82 therein. The post 84 is pulled to tighten the Dines knot 83 to ensure that the tissue has been approximated to the desired extent before the Dines knot 83 can be locked. The post 84 can then be held by the tensioning aid 50. For instance, the post 84 can be wrapped around the tensioning aid 50 or caught within a slot of the tensioning aid 50 to be held by it. For example as shown in FIG. 1K, the post 84 is wrapped around the double post configuration 50A in a figure eight. As such, the tensioning aid 50 functions to maintain tension on the post 84 after the post 84 has been pulled to tighten the sliding knot 82, and thereby allows the operator to partially or fully release the post 84. Releasing the post 84 allows the operator to hold the handle of the knot pusher 100A with one hand and the locker 86 to be pulled with the other free hand once the sliding knot 82 is at it its desired tightness. Thus the locker 86 can be pulled simultaneously as the post 84 is pulled. Furthermore, the tensioning aid 50 allows the physician for example that is using the knot pusher 100A to free up one hand to allow the physician to use other instruments during the procedure.

In summary, some embodiments of a method of the present invention provide for a method comprising the steps of: applying tension to one of the two strands of suture such as the post 84 to tighten said sliding knot 82 to a desired extent into a tightened configuration to approximate the tissue at the defect. This may be facilitated, for example, by providing an opposing groove 40D as mentioned above. Tension may then be maintained on the post 84 to maintain said sliding knot 82 in its tightened configuration. This may be facilitated, for example, by providing a tensioning aid 50 to secure the strand of suture such as the post 84 to the shaft 14 of the knot pusher 100A. Tension can then be applied simultaneously to the other of the two strands of suture to lock the sliding knot 82 in its tightened configuration.

Following locking of the sliding knot, the physician may deploy one or more additional knots to further secure the sliding knot 82 in place. In one specific embodiment, one or more half-hitches or other overhand knots 90 may be formed and or deployed. These may then be advanced, using the knot pusher 100A, towards the tissue site having the defect 95. In one particular example, a half-hitch or overhand knot 90 is formed using the post 84 and the locker 86. The knot pusher 100A is placed directly behind the overhand knot 90.

Figure 7C:
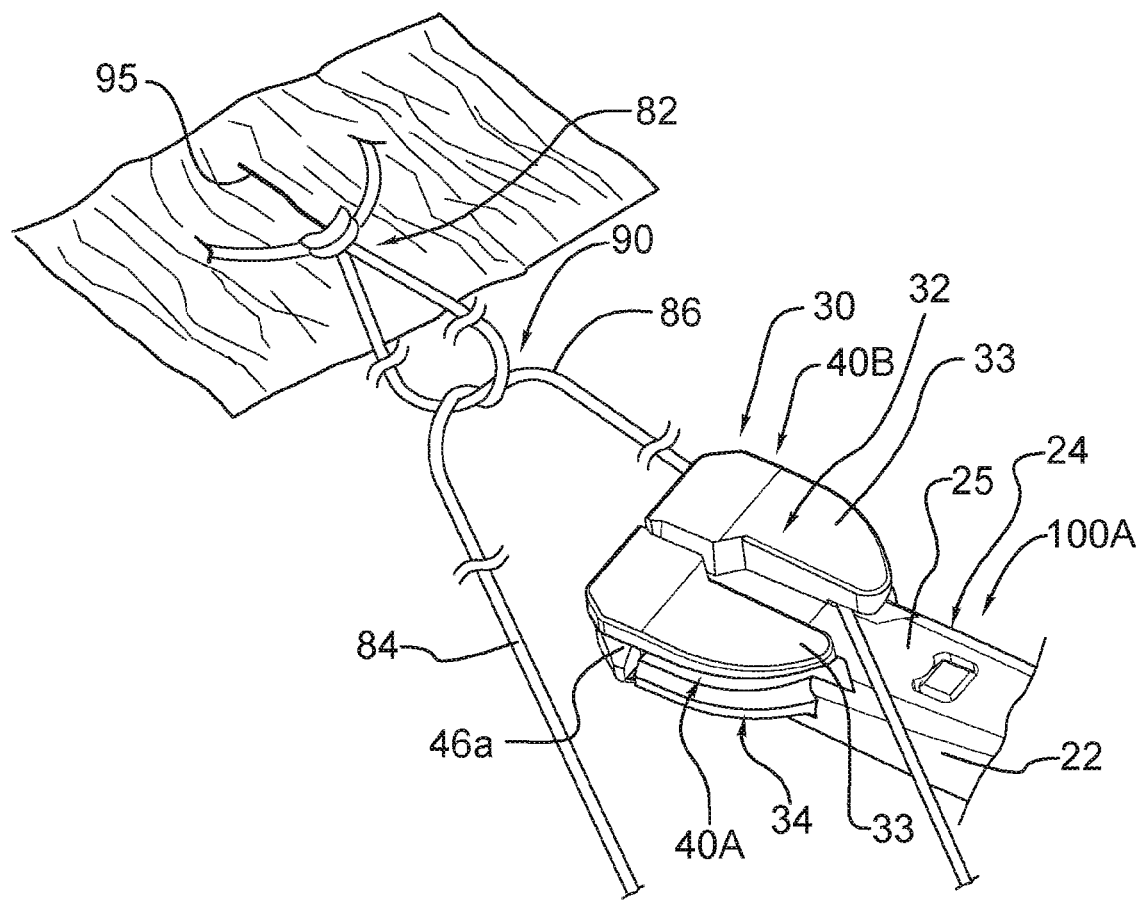

As shown in FIG. 7C, the knot pusher 100A is initially positioned such that one of the two strands of suture, such as the locker 86 is positioned against the top face of the neck 22 such that it rests against the tapered portion 24 thereof. As each of the opposed side grooves 40A and 40B are formed contiguously with the tapered portion 24, it allows each of the two strands of suture to be guided/lead into the into the side grooves 40A, 40B.

Figure 7D:
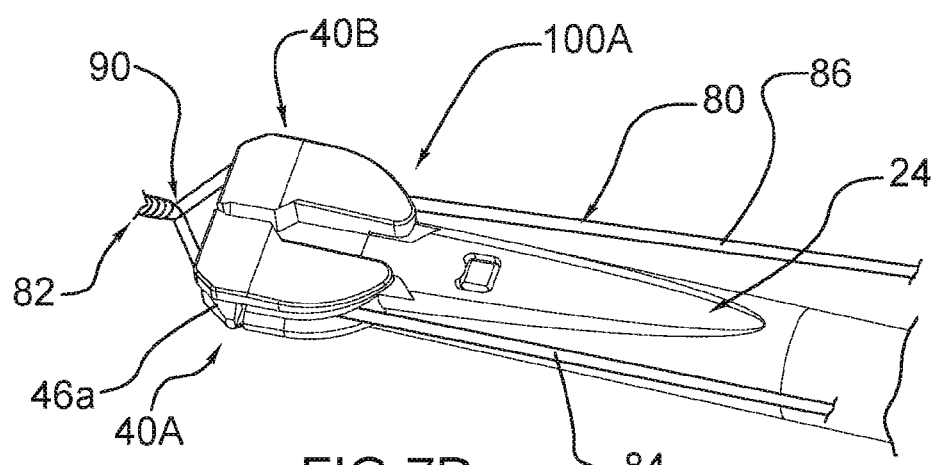

As shown in FIG. 7C, the flat planar surface 25 of the tapered portion 24 leads the locker 86 into the side groove 40B such that it rests between the top and bottom walls 32, 34. The knot pusher 100A may then be rotated, for example clockwise, to position the second strand of suture, such as the post 84, within the opposing side groove 40A, as shown in FIG. 7D. The flat planar surface 25 of the tapered portion 24 similarly aids in positioning of the post 84 within the side groove 40A. Thus, the tapered portion 24 facilitates loading of the suture strands within the knot pusher 100A to aid in the knot pushing procedure. Additionally, chamfered portions of the top and bottom walls 32, 34 also help guide the two suture strands (post 84, locker 86) within the two side grooves 40A, 40B. Additional features such as overhangs 33 of the top wall 32, allow each of the two strands of the suture 80 to be caught/secured within the side grooves 40A and 40B. The overhangs 33 allow the physician to hook the suture 80 into the side grooves 40A and 40B so that it engages with the knot pusher 100A. Thus, the overhangs 33 engage/capture the two suture strands prior to aid in guiding the two strands of suture within the side grooves 40A, 40B. This prevents the suture strands (post 84, locker 86) from falling out during transverse movement of the knot pusher 100A.

In some embodiments, the side grooves 40A, 40B have sufficient depth to retain the suture strands such as the post 84 and locker 86 when tension is maintained on the sutures. Additionally, in some embodiments a passive retention mechanism may be provided to retain the two strands of suture independently. In some such embodiments, for example where the suture strands such as the post 84 and locker 86 are passed through a pair of snaps such as snaps 46a and 46b (shown in FIGS. 2, 4B-4C) as they are guided into each of the side grooves 40A and 40B, the snaps function to retain the suture strands within these side grooves 40A, 40B. Additionally, chamfers on the snaps 46a, 46b may also aid in guiding suture 80 within the side grooves 40A, 40B.

The snaps 46a, 46b serve to constrain the sutures within the side grooves 40A and 40B even when tension is not maintained on the sutures. Therefore, the snaps 46a and 46b may help prevent the suture strands from disengaging from the knot pusher during, for example, patient movement or when tension is released from the suture strands in order to manipulate another instrument, and may thereby eliminate or reduce the need to reload the suture 80 into the knot pusher. As such, the snaps 46a, 46b may help reduce the time required for the knot pushing procedure.

Figure 7E:
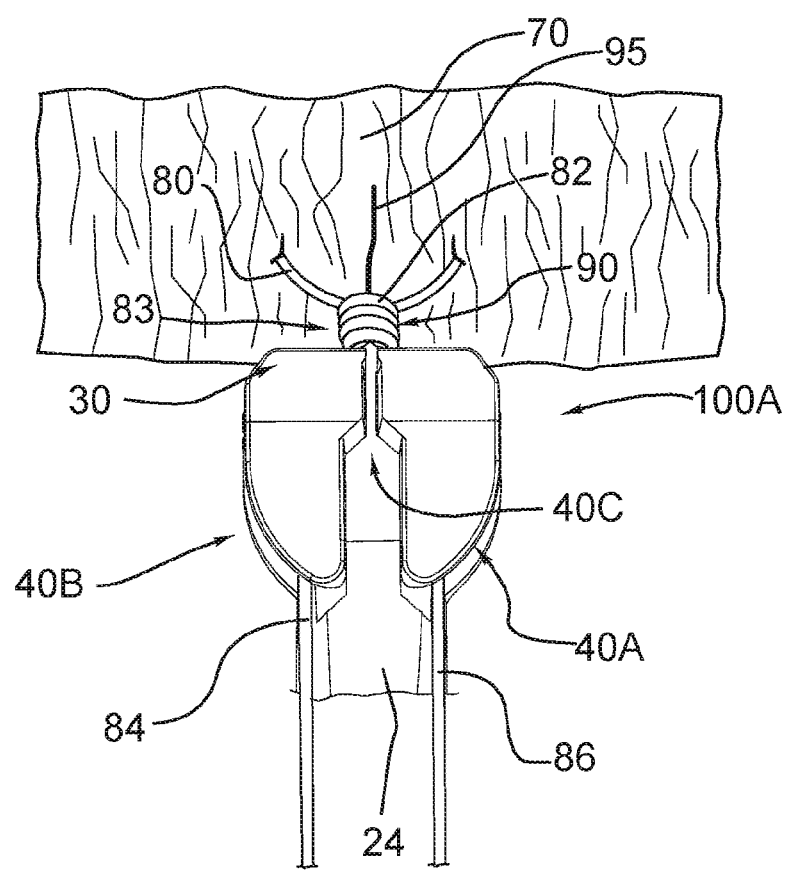

In some embodiments, the suture strands or limbs may be loaded onto the knot pusher 100A outside of the patient's body. After each strand of suture coming/deriving/extending from the overhand knot 90 has been placed within each of the respective side grooves 40A, 40B as shown in FIG. 7D, the knot pusher 100A is positioned directly behind the overhand knot 90. The knot pusher and the suture strands coupled thereto may then be advanced together into the patient's body to the target tissue surface. The knot pusher 100A is then advanced to push the overhand knot 90 towards the sliding knot 82. As the knot pusher 100A is advanced further, for example as shown in FIG. 7E, the knot pusher 100A functions to cinch the overhand knot 90 over top of the sliding knot 82 (such as the Dines knot 83).

The half-hitch or overhand knot 90 is centered between the side grooves 40A and 40B for securing the sliding knot 82. The central groove 40C' permits viewing of the overhand knot 90 as it is being advanced to ensure centering of the overhand knot so that equal tension is maintained on the two strands of sutures to guide the overhand knot on top of the sliding knot 82. Additionally, firm tension is maintained on the two suture strands, the post 84 and locker 86, as the knot pusher 100A is advanced. The knot pusher 100A may be pushed and retracted/released a plurality of times in order to tighten the half-hitch or overhand knot 90. In one specific example, the knot pusher 100A may be pushed and released four times to cinch the half-hitch or overhand knot 90. In some embodiments, four half-hitch or overhand knots 90 may be advanced towards the sliding knot 82 and tightened in order to secure the sliding knot 82 at the defect 95 within the tissue 70. Advancing and tightening four half-hitches or overhand knots provides an added advantage of preventing slipping or opening of the knot during loading conditions, as described further in the Examples below.

Figure 8:
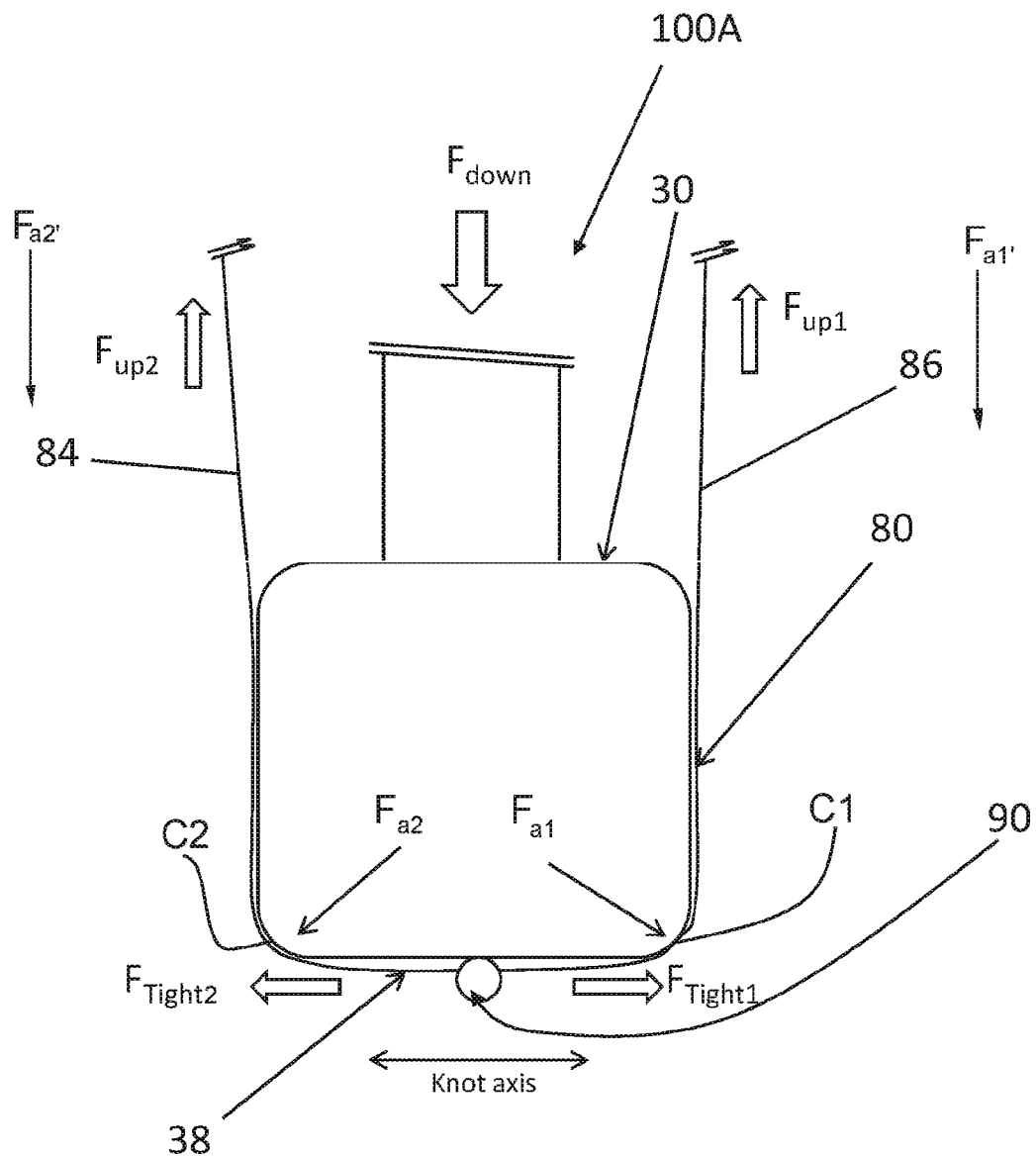
FIG. 8 schematically illustrates a distal head of a knot pusher and method of using the same, in accordance with an embodiment of the present invention.

The mechanism of pushing the overhand knot 90 is discussed further with reference to FIG. 8. A longitudinally directed force is applied by the user to the knot pusher 100A in a distal direction. This translates into a downward force ($F_{down}$) that is exerted by the distal head 30 against the suture strands (the post 84 and the locker 86). A portion of the knot pusher 100A, for example a curved or tapered portion of the side grooves (C1, C2), functions to translate a component of the applied force ($F_{down}$) which is substantially perpendicular to the suture strands at the distal face of the knot pusher into horizontal force components or tightening forces ($F_{tight1}$ and $F_{tight2}$) exerted against the portions of suture 80 that are substantially parallel to the distal face of the knot pusher.

More specifically, the downward force ($F_{down}$) results in an applied force ($F_{a1}$, $F_{a2}$) that is exerted on the suture strands by the distal head 30. The knot pusher 100A functions to translate a component of this applied force ($F_{a1}$, $F_{a2}$) into horizontal force components ($F_{tight1}$ and $F_{tight2}$) exerted against the suture 80. The knot pusher 100A also translates a component of the applied force ($F_{a1}$, $F_{a2}$) into vertical force components or downwards forces ($F_{a1}'$, $F_{a2}'$) that are exerted on the suture strands in a distal direction. Since the suture strands are held by the user, resistive forces ($F_{up1}$, $F_{up2}$) are exerted against the suture strands, which counteract the vertical force components ($F_{a1}'$, $F_{a2}'$) of the applied force ($F_{a1}$, $F_{a2}$). As such, the vertical components ($F_{a1}'$, $F_{a2}'$) of the applied force ($F_{a1}$, $F_{a2}$) are balanced by the resistive forces ($F_{up1}$, $F_{up2}$) whereas the parallel or horizontal force components ($F_{tight1}$ and $F_{tight2}$) of the applied force ($F_{a1}$, $F_{a2}$) continue to act in opposite directions on the suture strands extending from the overhand knot 90 to tighten the overhand knot 90. In other words, the counterbalancing of the horizontal force components ($F_{tight1}$ and $F_{tight2}$) allows tightening of the overhand knot 90. More specifically, the parallel force components ($F_{tight1}$ and $F_{tight2}$) function to spread the suture strands by about 180 degrees in order to tighten the overhand knot 90 against the tissue surface which it abuts.

Additionally, as the knot pusher 100A is advanced to tighten the overhand knot 90, the intermediate groove 40C is used as a central viewing channel to view the overhand knot 90 as it is being pushed towards and tightened on the target surface, for example as shown in FIG. 7E. This visual feedback enables centering of the overhand knot 90 to allow equal tension to be maintained on the two strands of suture in order to adequately position and tighten the overhand knot 90 onto the target surface as described hereinabove.

EXAMPLE 1

The following tests were performed using a segment of porcine spine. A defect was made in a cervical disc, closed with a Dines knot as described hereinabove, and backed up with various amounts of half-hitch overhand knots. The degree or extent of knot slippage was observed after 1500N of compressive loading and 4000 cycles of flexion/extension after advancement of 2 half-hitches, 3 half-hitches and 4 half-hitches. Five samples for each of the knot constructs were observed. The average knot slippage observed for 2 half-hitches was about 8.8 mm, whereas the average knot slippage observed for 3 half-hitches was about 2.8 mm. However, for 4-half-hitches the inventors were surprised to observe that there was no knot slippage. This surprising and unexpected result was replicated under increased loading conditions. Knot slippage was observed for a 4 half-hitch knot construct after 1500N of compressive loading and 85000 cycles of flexion/extension. The average slippage was equal to about 0.8 mm. In conclusion, the inventors were surprised to observe that even under increased loading conditions, the four half-hitch knot construct substantially prevents knot slippage under normal loading conditions.

EXAMPLE 2

In another example, force values were determined for slippage or breakage for a knot construct comprising a sliding knot in the form of a Dines knot that is backed up with 2, 3 or 4 half-hitches. Knot strength (defined as the force required to break the construct or to cause knot slippage) was determined to be 47 Newtons for 2 half-hitches, 75 Newtons for 3 half-hitches and 105 Newtons for 4-half-hitches. The mode of failure observed for the two half-hitch knots was slippage, whereas the mode of failure observed for the 4-half-hitches was predominantly breakage. This was a surprising and unexpected result further indicating that the four half-hitch knot construct is not prone to slippage. The breakage of the 4-half-hitches occured under force conditions that exceed the forces generally seen at the site of a suture placed within a region of tissue within the body, such as the intervertebral disc. This further confirmed that 4-half-hitch knot construct is substantially resistant to slippage.

In some situations, there is limited maneuverability of the knot pusher in terms of positioning the knot pusher device to capture limbs of suture. For example, in some situations where the knot pusher is being used to advance a suture knot deep into the patient's body there may be limited room to enable movement/repositioning or adjustment of the knot pusher to allow the suture limbs to be captured within each of the side grooves. Additionally there may not be sufficient room to allow individual insertion of each of the limbs of suture into the respective side grooves. In some such embodiments, the knot pusher is equipped with one or more features to facilitate insertion of one or more of limbs of suture into the side grooves. In one such embodiment, as shown in FIG. 9A-9F, a knot pusher 200A is provided with features to assist with loading of the suture limbs within each of the side grooves.

Figure 9A:
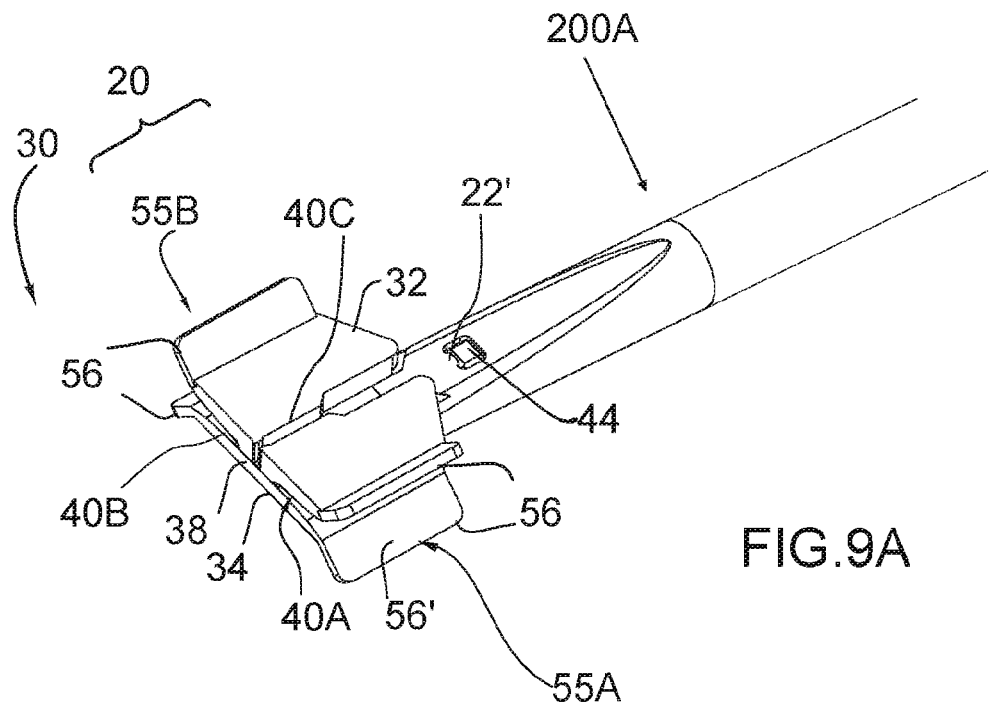
FIGS. 9A-9E illustrate a knot pusher comprising a suture guide in accordance with an alternative embodiment of the present invention.

As an overview, the general structure of the knot pusher 200A is described herein below. As shown in FIG. 9A-9E, a knot pusher 200A is disclosed comprising a distal head 30 for pushing various types of knots including one or both of sliding knots and overhand knots formed from a suture, where two limbs of suture extend from each of the knots. In some such embodiments, the knot pusher 200A as shown in FIG. 9A, may be operable to push both of a sliding knot and subsequent overhand knots in a single procedure. In other embodiments, the knot pusher 200A may be operable to push one of a sliding knot or an overhand knot.

Similar to embodiments described previously herein above, the knot pusher 200A comprises a device proximal portion comprising a handle and a shaft that is coupled to the distal portion 20. The distal portion 20 comprises the distal head 30 which defines top and bottom walls 32, 34 that terminate in a distal knot pushing surface 38, as shown in FIG. 9A. Similar to embodiments described herein above, the knot pusher 200A comprises opposed side grooves 40A, 40B, as shown, that are defined between the top and bottom walls 32, 34 of the distal head 30. These side grooves 40A, 40B extend proximally from the knot pushing surface 38 along the distal head 30, and are each operable to receive one of the two limbs of suture that are exiting from an overhand knot to aid in pushing the overhand knot during advancement of the distal head 30. In some embodiments, as discussed previously hereinabove the side grooves 40A, 40B may extend at least partially along the length of the distal head 30. In other embodiments the side grooves 40A, 40B may extend substantially along the longitudinal length of the distal head 30. In some embodiments, as shown, the distal head 30 may additionally comprises a top wall suture receiving element associated with the top wall for receiving one of the two limbs of suture exiting from a sliding knot to facilitate advancement of the sliding knot during advancement of the distal head 30. In one specific example, the top wall suture receiving element is in the form of an intermediate groove 40C, which that is formed within the front surface of the top wall 32 of the knot pusher 200A. In some embodiments, the intermediate groove 40C extends proximally from the distal knot pushing surface 38, as shown in FIG. 9A.

Furthermore, as shown in FIG. 9A, the knot pusher 200A additionally comprises one or more suture guides 55A, 55B. The suture guides 55A, 55B are defined by said top and bottom walls 32, 34 to guide and position at least one of the two limbs of the suture exiting an overhand knot into one of the side grooves 40A, 40B, Referring now to FIG. 9B, each of the suture guides 55A, 55B defines a respective guiding channel 57 that is in communication with the respective side groove 40A, 40B. The suture guides 55A, 55B provide enhanced ease in loading the suture within the side grooves 40A, 40B, by allowing a limb of suture to be guided into the respective side groove 40A, 40B. As such, the suture guides 55A, 55B allow suture limbs to be caught and loaded into the knot pusher 200A one at a time.

More particularly, as shown in FIG. 9A, each of the suture guides 55A, 55B comprises flanges 56 that extend or radiate outwards laterally or transversally at an angle from the top and bottom walls 32, 34. The flanges 56 form flange pairs that are functional to guide suture into the respective side grooves 40A, 40B. Each of the flanges 56 extend outwards and laterally away from the top and bottom walls 32, 34 and additionally in a direction above the top wall 32 and bottom wall 34. In some such embodiments, the flanges comprise a tapered configuration. In other embodiments, one or more of the flanges 56 forming the suture guides may comprise a curved configuration. In other embodiments, the flanges 56 are generally shaped to guide the suture limbs into the respective side grooves 40A, 40B. As the suture limb is being loaded into one of the side grooves 40A, 40B the suture limb contacts the curved or tapered interior surface 56' of the flange 56, and is guided in sliding contact with the surface 56' into one of the side grooves 40A, 40B. The suture guides 55A, 55B permit suture to be loaded from the top or the bottom into the knot pusher 200A. In other words, the two limbs of suture can be held either above or below the knot pusher 200A to enable the suture limbs to be engage with the suture guides 55A, 55B to be guided into the side grooves 40A, 40B. The flanges 56 of the suture guides 55A, 55B provide a wider opening defining the guiding channel 57 which effectively increases the target area within which the two limbs of suture are to be inserted to be guided into the respective side grooves 40A, 40B. This enhances the ease of use of the knot pusher 200A by allowing the suture limbs to be loaded within the side grooves 40A, 40B with relative ease.

Figure 9B:
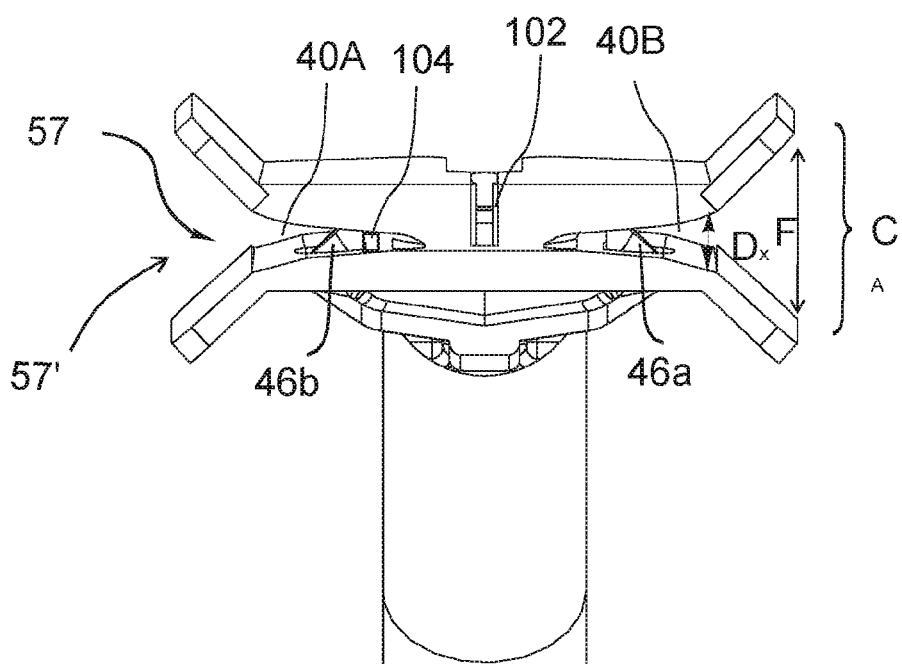
Figure 9C:
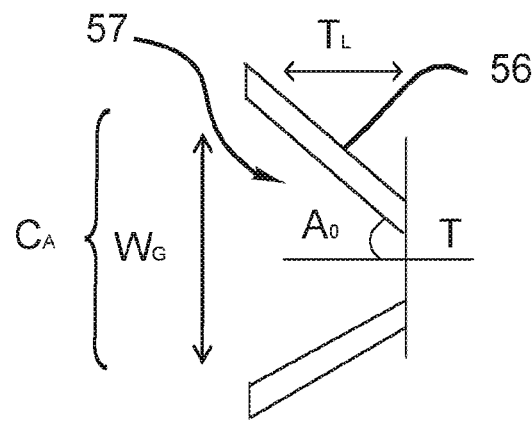
Figure 9D:
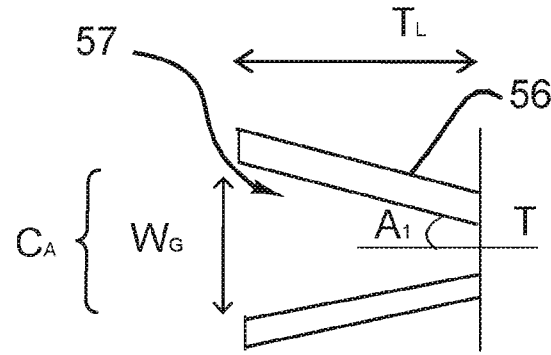
Figure 9E:
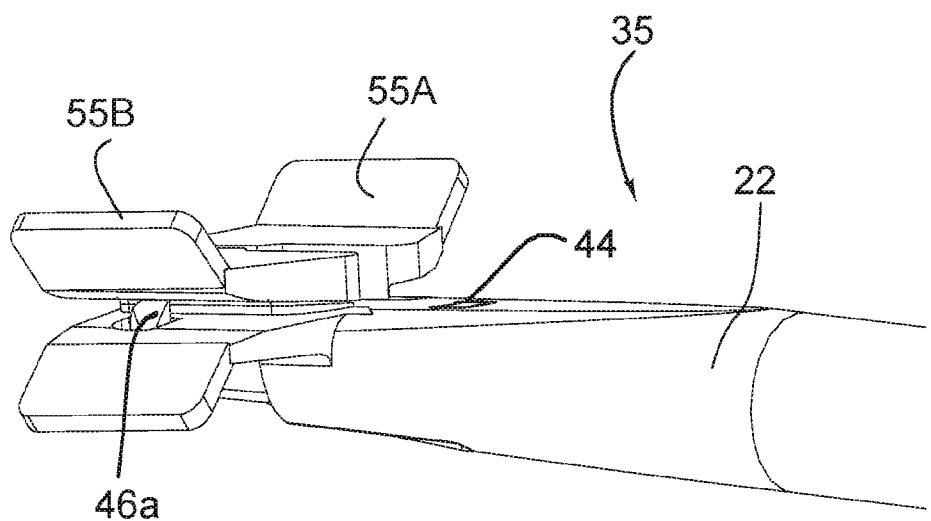

In one particular example, with reference now to FIG. 9B, the guiding channel 57 comprises a funnel shaped opening 57' where the flanges have a width that is denoted by reference letter F, that is wider than the distance $D_X$ between the interior surfaces of the top and bottom walls 32, 34, as shown in FIG. 9B, which increases the capture area $C_A$, within which suture limbs can be caught and loaded. In other words, the knot pusher 200A provides a guiding channel 57 that has a width greater than a width of said side grooves. In some such examples, as shown in a FIGS. 9C and 9D, which illustrate a diagrammatic representation of a guiding channel 57, the flanges 56 are at an acute angle with respect to the transverse axis T of the distal head 30. In one particular example, as shown in FIG. 9C, the flanges 56 are at an acute angle $A_0$ such that the width $W_G$ of said guiding channel 57 is greater than a transverse length $T_L$ of said guiding channel 57 to provide a substantially large capture area $C_A$ to facilitate capture of said one of the two limbs of suture within the at one of the two side grooves 40A, 40B, while limiting a size of said distal head 30 by limiting the transverse length of the distal head 30. In another example, as shown in FIG. 9D, the flanges are at an acute angle $A_1$ that is substantially smaller than angle $A_0$, such that the width $W_G$ of said guiding channel is smaller than a transverse length $T_L$ of said guiding channel 57 to facilitate retaining said at least one of the two limbs of suture within said at least one side groove while providing a capture area $C_A$ for facilitating capture of said at least one of the two limbs of suture. In some such embodiments, the knot pusher 200A may additionally have side grooves 40A, 40B that have a width that narrows inwardly, i.e. towards a longitudinal axis of said knot pusher 200A, to aid in retaining said two limbs of suture within the said side grooves 40A, 40B. For example, the angles or widths of the side grooves 40A, 40B provide retention means such that the suture remains enclosed or retained within the side grooves 40A, 40B. In some embodiments, as shown in FIGS. 9B and 9E, snaps 46a, 46b may additionally be provided within the side grooves 40A, 40B that work in conjunction with suture guides 55A, 55B to facilitate routing and retaining of the suture limbs within the side grooves 40A, 40B, similar to embodiments described previously hereinabove. The snaps 46a and 46b may form a part of, or be integral with, a snap arm 44 coupled to the neck 22 of the distal portion 20 via a snap fit arrangement, as described herein above. As shown in FIG. 9A, the neck may comprise a raised projection 22' to facilitate the snap fit with snap arm 44. The knot pusher 200A enables two limbs of suture to be captured sequentially within the respective side grooves 40A, 40B to facilitate advancement of an overhand knot.

Figure 9F:
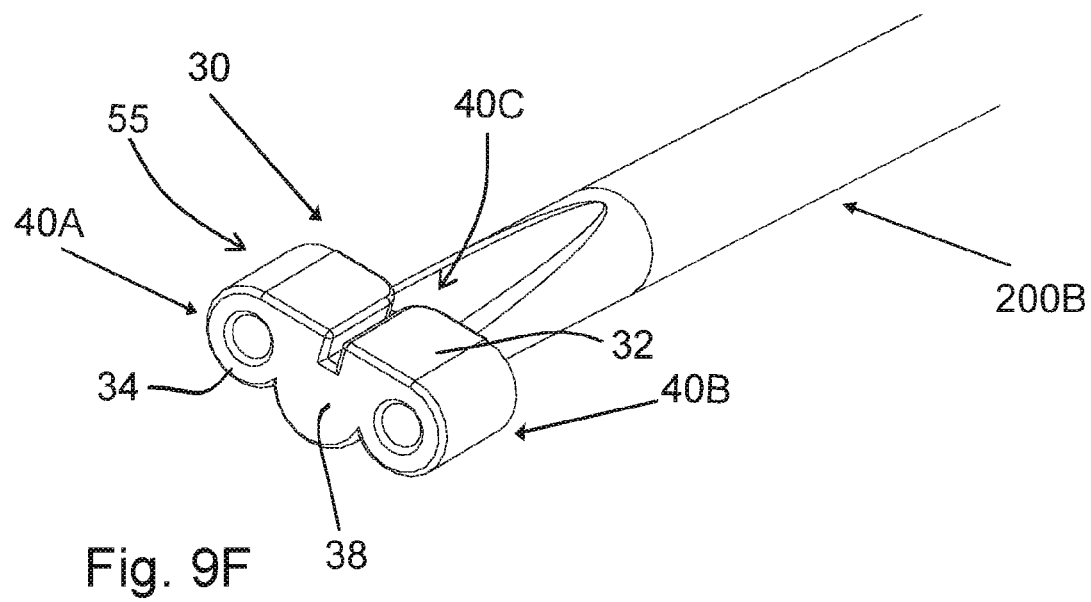
FIGS. 9F-9G illustrate an alternative embodiment of knot pusher with enclosed side grooves, in accordance with an embodiment of the present invention.
Figure 9G:
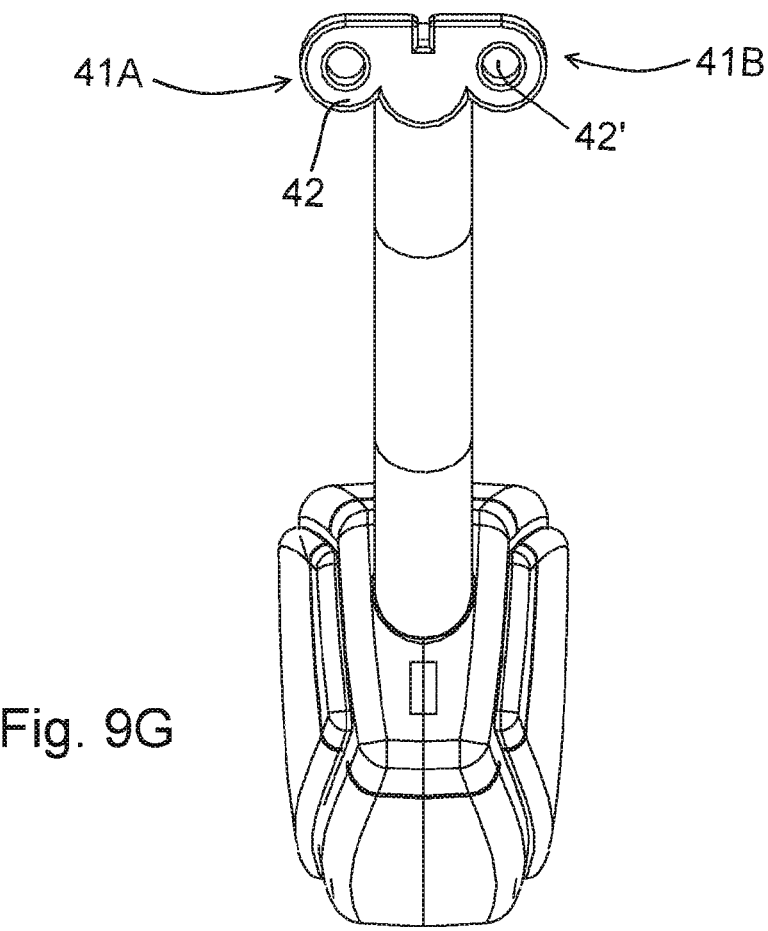

In additional embodiments, as shown in FIG. 9F, a knot pusher 200B is provided that similar to embodiments discussed herein above is usable for pushing various types of knots including sliding knots and overhand knots formed from a suture, two limbs of the suture extending from the knots. The knot pusher 200B comprises: a distal head 30 defining top and bottom walls 32, 34 terminating in a distal knot pushing surface 38. As shown in FIGS. 9F and 9G, the knot pusher 200B additionally comprises side grooves 40A, 40B defined between said top and bottom walls, that extend proximally from the knot pushing surface 38 along the distal head 30 and each is functional or operable to receive one of the two limbs of suture during advancement of the distal head to aid in pushing an overhand knot. In the particular embodiment shown, at least one of the two side grooves 40A, 40B comprises an annulus 42 forming an enclosed side groove 41A or 41B that defines a lumen 42' there-through. As such the annulus 42 defines a suture guide 55 for guiding and retaining one of the two limbs of suture therein. In some such embodiments, annulus 42 defines a tubular or circular opening or a cylinder as shown in FIG. 9F. In some such embodiments, tubular or circular opening or cylinder extends substantially along the length of the at least one the side grooves 40A, 40B or in other words the length of the distal head 30. In other embodiments the tubular or circular opening or cylinder extends partially along the length of the at least one the side grooves 40A, 40B or distal head 30. Furthermore, as shown, the knot pusher 200B additionally comprises a top wall suture receiving element such as an intermediate groove 40C associated with said top wall 32 for receiving one of the two limbs of the suture during advancement of the distal head 30 to facilitate advancement of a sliding knot.

During use the knot pusher 200B as shown in FIGS. 9F-9G, the two limbs of suture may be threaded through the enclosed side grooves 41A and 41B after the overhand knot is formed to enable the knot pusher 200B to push the overhand knot to a desired location within the patient's body. For example the overhand knot may be advanced after a sliding knot has been placed at the desired tissue site using the intermediate groove 40C as described previously. In one example, the knot pusher 200B is usable with one or more snares which allows the suture limbs to be loaded into the enclosed side grooves 41A, 41B. In some such examples, the one or more snares may be pre-loaded into the enclosed side grooves 41A, 41B. In other examples the one or more snares may be inserted within the enclosed side grooves 41A, 41B at the point of use. Each of the suture limbs may be guided through a snare and the snare may be pulled through one of the enclosed side grooves 41A, 41B to allow the suture limb to be guided and passed there-through. Once the suture limbs are loaded into the enclosed side grooves 41A, 41B the knot pusher 200B may be advanced as desired to push the overhand knot to the desired tissue site. As such each of the enclosed side grooves 41A, 41B function as a suture guide to guide the suture limbs and retain them within the side groves 40A, 40B during advancement of a knot such as an overhand knot.

Figure 10A:
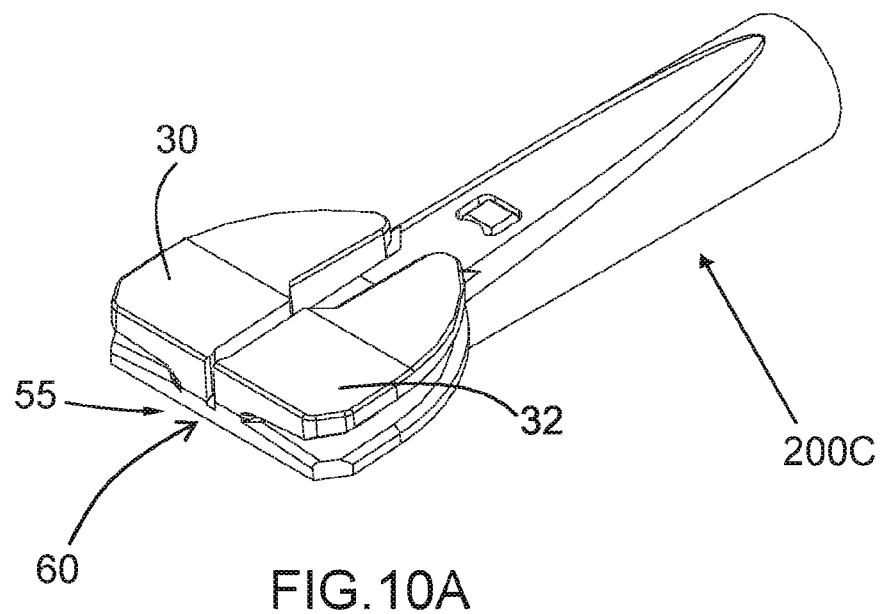
FIGS. 10A-10D illustrate a knot pusher with a suture guide comprises a suture containment element, in accordance with an embodiment of the present invention.
Figure 10B:
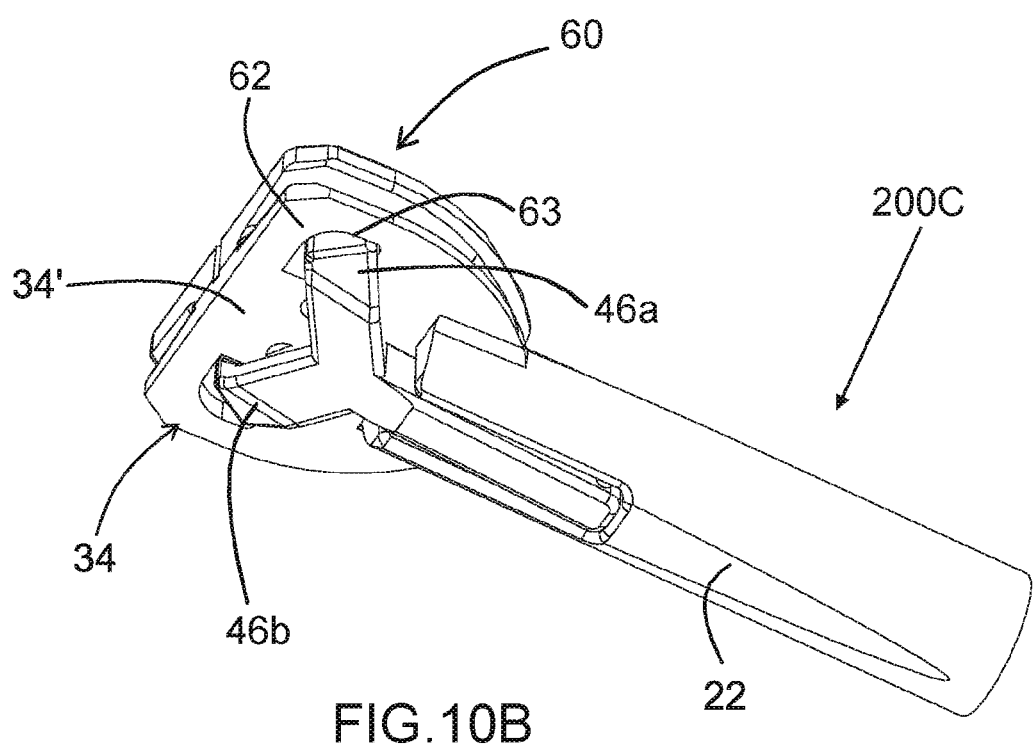
Figure 10C:
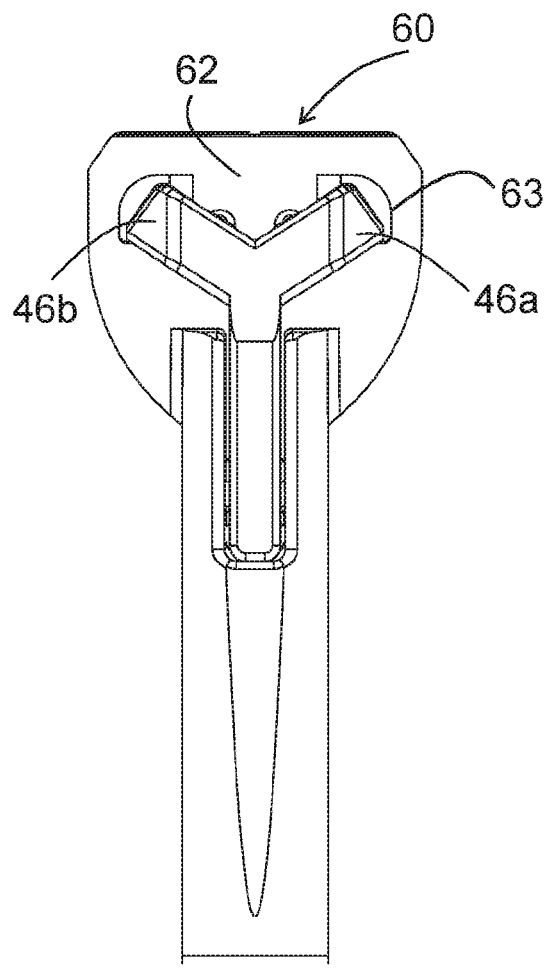
Figure 10D:
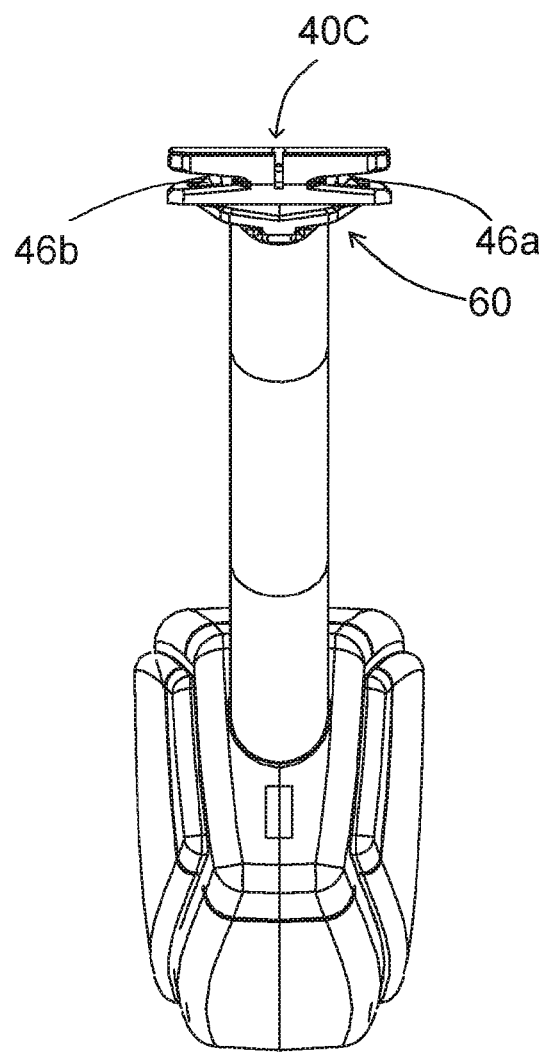

As described previously hereinabove with respect to FIGS. 1B, 4B and 4C, and as shown in FIGS. 10A and 10B, some embodiments of the present invention comprise snaps 46a, 46b to retain the limbs of suture within each of the side grooves 40A, 40B. In one particular example, the side groove suture retaining element comprises a snap arm 44 that is coupled to the neck 22, for example via a force fit or snap fit arrangement. The snap arm 44 comprises snaps 46a and 46b that extend radially from a longitudinally extending stem 46. In one specific example, further shown in FIG. 1B and FIG. 2, a tab 45 of the snap arm is received within an opening 23 within the neck 22 and engages therewith. In the illustrated embodiment, the snaps 46*a* and 46*b* each form a portion of bottom wall 34. In some embodiments, the snap arm 44 is resilient allowing the snaps 46*a* and 46*b* to flex from their nominal or closed position to an open position to allow the two ends of the suture to be received within the opposed side grooves 40A and 40B. Thereafter the snaps 46*a* and 46*b* return to their nominal or closed position to retain the two suture ends in each of said side grooves 40A and 40B. The snaps 46*a*, 46*b* reduce the risk of the suture strands falling out of position from within the side grooves 40A and 40B when tension is not maintained on the suture strands. This helps to minimize the risk of suture strands exiting the side grooves 40A, 40B during the procedure and thus helps to minimize the need to reinsert the suture strands within the side grooves 40A and 40B as the knot pusher is being advanced distally to push the knot.

In some such embodiments as shown in FIGS. 10A-10F, a knot pusher 200C is shown that prevents suture from getting trapped in between the snaps 46*a* or 46*b* and the exterior surface 34' of the rear wall 34. By preventing the suture strand from getting beneath the snaps 46*a*, 46*b* the knot pusher 200C minimizes the risk of the user not being able to advance the knot in the desired manner due to the suture strand getting trapped beneath the rear wall 34. Thus, in some embodiments a feature is provided on the knot pusher 200C in order to prevent the risk of suture limbs or strand from getting stuck within the distal head 30 of the knot pusher during advancement of a knot.

In one such embodiments of the present invention a knot pusher 200C is provided, as shown in FIGS. 10A-10B, that is usable for pushing various types of knots including overhand knots formed from a suture. Similar to embodiments discussed previously the knot pusher 200C comprises at least one side groove suture retaining element to retain the two limbs of the suture within the side grooves. In some such embodiments, the side groove suture retaining element comprises a resilient snap arm 46 with snaps 46*a*, 46*b* that form a portion of one of the top and bottom walls 32, 34. The knot pusher 200C additionally defines a suture guide 55 that comprises a suture containment means or element 60, as shown in FIGS. 10A and 10B to contain the limbs of the suture within side grooves to maintain the position of the suture limbs to retain them therein during use. The suture containment means or element 60 defines a barrier for co-operating with the side groove suture retaining element such as the snap arms 46*a*, 46*b* to retain the two limbs of the suture within the side grooves 40A, 40B. In some embodiments, the suture containment means or element 60 that is defined by one of said top and bottom walls 32, 34 and comprises an extending portion 62 of one of said top and bottom walls 32, 34 that extends about the side groove retaining element such as the snaps 46*a*, 46*b* forming a barrier to encompass the snaps 46*a*, 46*b* therein. More specifically, in the embodiment shown, the suture guide 55 comprising the suture containment element defines a cavity 63 within a portion of the bottom wall 34, wherein the snaps 46*a*, 46*b* are receivable within the cavity 63. A barrier is created by the extending portion 62 of the bottom wall 34 which encompasses the snaps 46*a*, 46*b* which is additionally shown in FIGS. 10C and 10D. This barrier prevents the limbs of suture that are received within the side grooves 40A, 40B from being removed therefrom during use. More specifically, the barrier prevents the suture limbs from getting behind the rear wall 34. As such the suture limbs are thus kept within the side grooves 40A, 40B as the knot pusher 200C is used to advance a knot such as an overhand knot, allowing the user to push the suture knot. In some such embodiments, the knot pusher 200C comprises a top wall suture receiving element associated with said top wall such as an intermediate groove 40C for receiving one of the two limbs of the suture during advancement of the distal head 30 to facilitate advancement of a sliding knot.

Figure 10E:
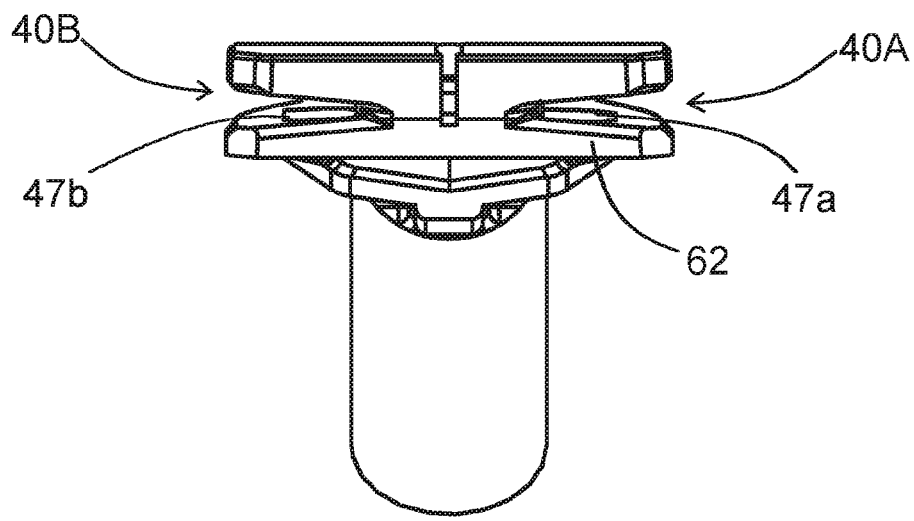
FIGS. 10E-10H illustrate alternate embodiments of a knot pusher in accordance with the present invention.
Figure 10F:
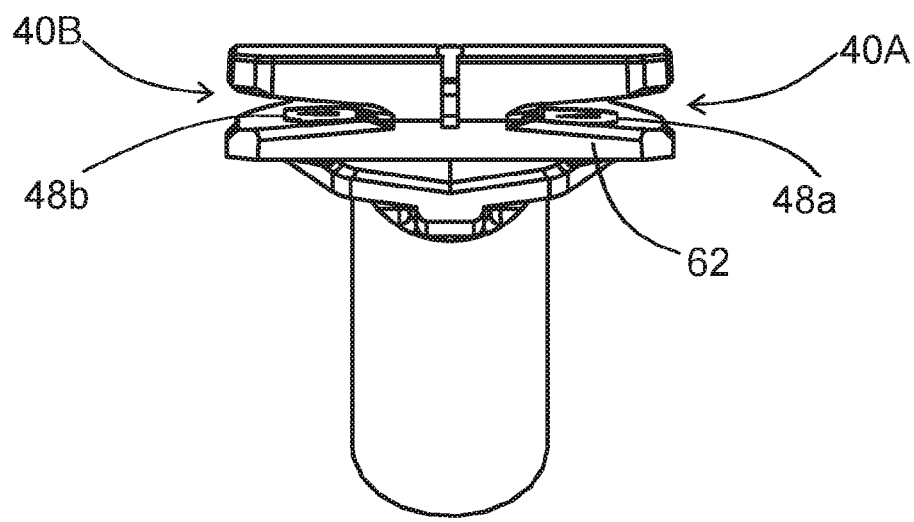
Figure 10G:
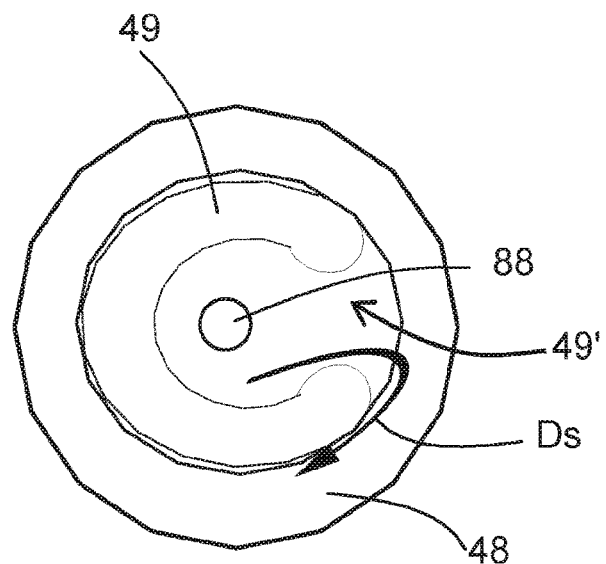
Figure 10H:
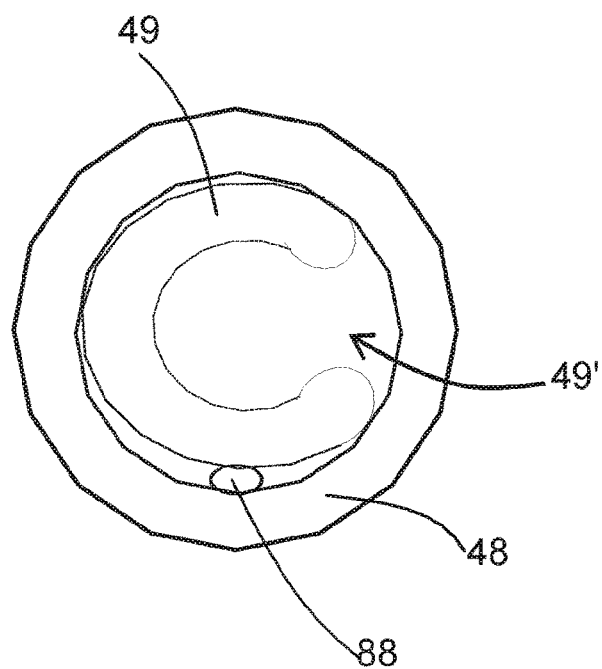

In other embodiments, the side groove suture retaining element comprises a resilient material 47*a*, 47*b* that is placed within the interior walls of one of the side grooves 40A, 40B that grips the suture in order to retain the two limbs of suture within the two side grooves. In one such example the resilient material 47*a*, 47*b* comprises a friction pad as shown in FIG. 10E. The friction pad is deformable and as the suture is inserted within the side groove 40A or 40B it compresses the friction pad, allowing the suture to be held between the friction pad and the inner walls of the side groove 40A or 40B. The resilient material 47*a*, 47*b* co-operates with the extending portion 62 of the bottom wall 34 to retain the two suture limbs within the side grooves 40A, 40B. In a particular example, the friction pad comprises a silicon pad. In some such embodiments, as shown in FIG. 10F the resilient material comprises an O-ring 48*a*, 48*b* that is mounted within at least one of the side grooves 40A, 40B that provides friction to retain the suture limb in position. In one particular embodiment, the side grooves 40A, 40B comprise a hollow projection 49 with a side opening 49' wherein said O-ring 48 is mounted onto the projection 49. The suture limb 88 can be initially passed through the side opening 49' of the projection 49, as shown in FIG. 10G. The suture limb 88 can then be guided and routed around the projection as shown by directional arrow $D_s$ so that it is seated between the projection 49 and the O-ring 48, as shown in FIG. 10H. Thus, the O-ring in conjunction with the projection 49 function as a suture retaining element to enable the limb of suture 88 to be held tight in sealing engagement with the O-ring and the projection within one of the side grooves 40A, 40B. In some such embodiments, the O-ring is usable with a knot pusher 200B that comprises enclosed side grooves 41A and 41B wherein the hollow projection 49 is provided within one or both of the enclosed side grooves 41A, 41B.

In some embodiments, there is a need to provide a knot pusher that facilitates guidance and advancement of a knot while allowing the two limbs of suture to be held parallel to one another. Thus, there is a need to enable the two limbs of suture to be teased apart and further to be guided into each of the side slots 40A, 40B. In some such embodiments, the knot pusher may be provided with a feature that enables teasing and guiding of suture limbs when held parallel to one another which may additionally facilitate pushing of more than one overhand knot in sequence, which may provide a means to keep track of the number of overhand knots deployed.

In some such examples, as shown in FIGS. 11A and 11B, a knot pusher 200D is provided with a suture guide that comprises a guiding edge 65 that extends away from said distal head 30 along a plane that is perpendicular to the distal head 30 to maintain a separation between the two limbs of suture to tease them apart in order to facilitate loading of said two limbs of suture into the side grooves 40A, 40B while the two limbs of suture are held substantially parallel to one another during use.

Figure 11C:
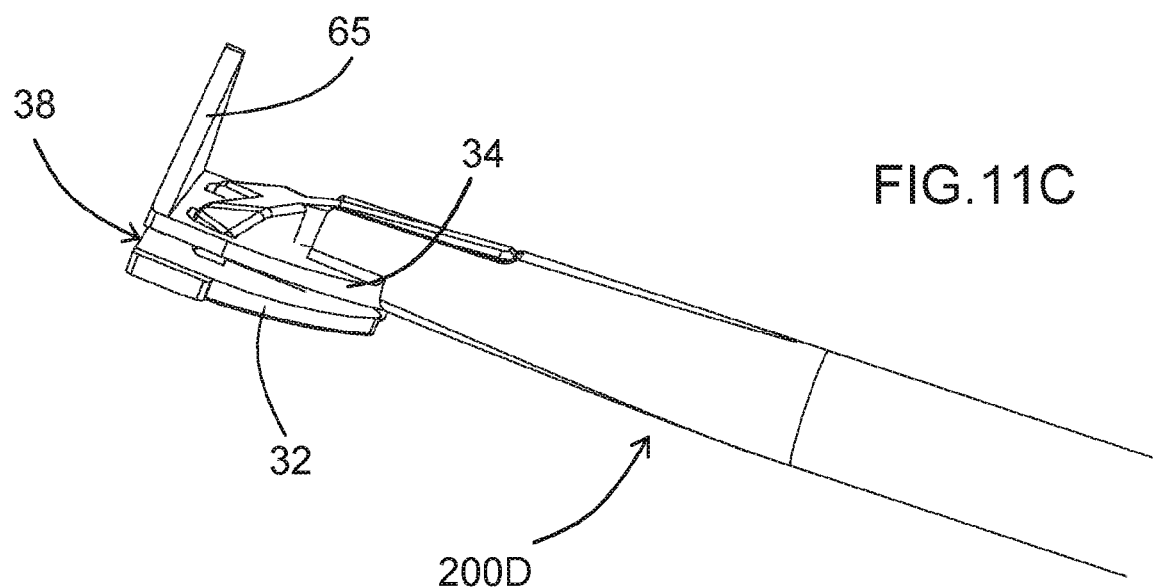
Figure 11D:
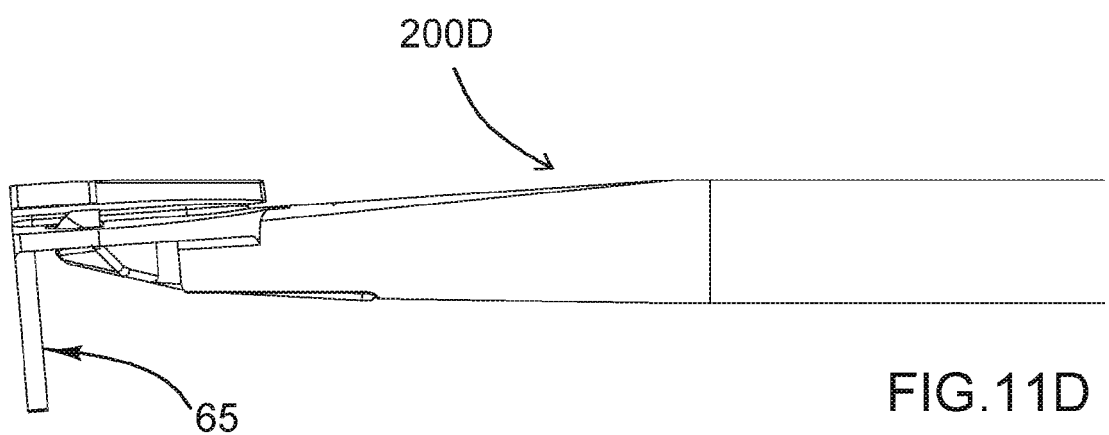
Figure 11E:
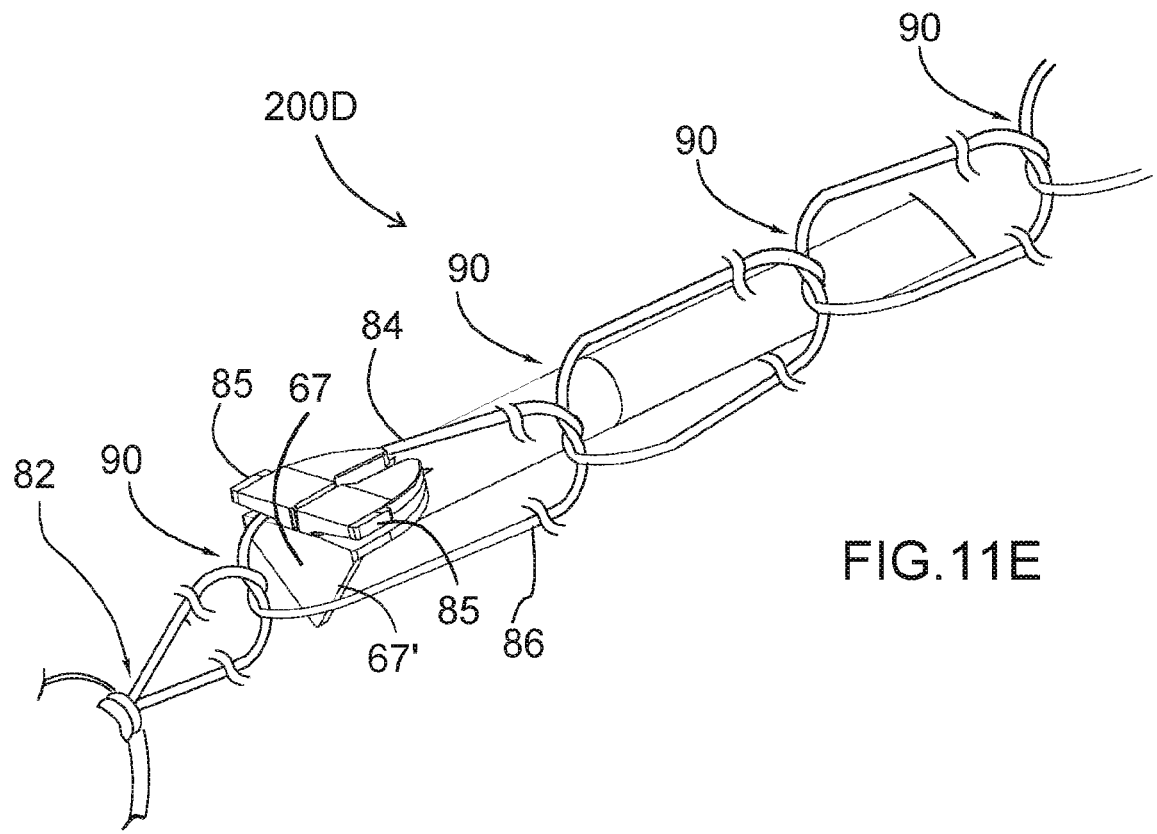

In some such embodiments, as additionally shown in FIG. 11C, the knot pusher 200D is similar to embodiments described herein above and is usable for pushing various types of knots including overhand knots formed from a suture, where two limbs of the suture extend from the knot. Similar to previous embodiments, the knot pusher 200D defines a distal head 30 defining a longitudinal axis that defines top and bottom walls 32, 34 that define the side grooves 40A, 40B to aid in pushing an overhand knot with the top and bottom walls 32, 34 terminating in a distal knot pushing surface 38. In some examples, the knot pusher 200D additionally comprises a top wall suture receiving element associated with said top wall such an intermediate groove 40C for receiving one of the two limbs of the suture during advancement of said distal head 30 to facilitate advancement of a sliding knot. As shown in FIGS. 11B and 11D, in some examples, the guiding edge 65 extends away from the distal head 30 in a top to bottom direction. More specifically, the guiding edge 65 extends downwardly away from the bottom wall 34 to permit loading of said two substantially parallel held limbs of suture to be loaded from below. In some instances, the guiding edge 65 extends substantially transversally along the width $W_d$ of the distal head to additionally guide said two limbs of suture into the respective side grooves as shown in FIG. 11B. In some cases, the guiding edge 65 extends completely along the width of the distal head from edge to edge as shown in FIG. 11E to facilitate guidance and insertion of the limbs of suture into the side grooves 40A, 40B. In some such embodiments, the guiding edge 65 comprises a substantially tapered configuration 67 with tapered edges 67' as illustrated in FIG. 11B. More specifically, the guiding edge 65 comprises a substantially triangular or inverted v-shaped configuration defining two tapered edges 67' that extends substantially between the side grooves along the distal head 30.

The method of loading the limbs of suture within the side grooves 40A, 40B using the guiding edge is shown in FIG. 11E, in order to push and advance an overhand knot 90 to a desired site within the patient's body. In some embodiments, one or more overhand knots 90 may be advanced to secure a sliding knot 82 that has been placed in the tissue. The knot pusher 200D may be approached from above to permit the substantially parallel limbs of suture to be loaded from below the knot pusher 200D. More specifically, as the knot pusher 200D is advanced the tapered edges 67' of the tapered guiding edge 67 contact the two limbs of suture exiting the overhand knot 90—the post 84 and the locker 86—and functions to tease them apart as shown in FIG. 11E. Furthermore, as the two strand of suture are teased apart they are guided respectively into the side grooves 40A and 40B allowing the use to catch the limbs of suture within the side grooves 40A, 40B. The knot pusher 200D may comprise an additional feature in the form of one or more landing pads 85 as is further illustrated in FIGS. 12B and 12C. The landing pads 85 extend laterally away from the distal head 30 beyond the edge of the side grooves 40A, 40B. Each of the landing pads 85 function to stop the suture limbs from completely sliding away from the distal tip 30 while they are being inserted within the side grooves 40A, 40B. Each of the landing pads 85 prevent the suture limbs from disengaging from the distal head 30 and ensure that the suture limbs are maintained or kept in position in front of the side grooves 40A, 40B. As such the landing pad 85 functions as a suture guide 55 to guide the suture limbs into respective side grooves 40A, 40B.

With reference again to FIG. 11E, multiple preformed overhand knots 90 may also be advanced using the knot pusher 200D. The overhand knots 90 may be created at the same time for example after a sliding knot 82 has been placed in tissue. Each overhand knot 90 may then be sequentially advanced one by one using the knot pusher 200D. In other words advancing multiple preformed overhand knots 90 involves independently loading the suture limbs for each overhand knot into the side slots 40A, 40B using the guiding edge 65 to tease the two limbs of suture apart and guide or direct each of the two limbs of suture into the respective side slots 40A, 40B. Once the suture limbs have been loaded the overhand knot 90 the knot pusher 200D is used to push the overhand knot 90 to the tissue site. The process is repeated for each overhand knot 90 with suture limbs emanating from each knot being loaded into the knot pusher 200D using the guiding edge 65, and then using the knot pusher 200D to advance the knot to the tissue site. The distal most overhand knot 90 is advanced first, with each time the next overhand knot that is in the most distal position being advanced next. As such some embodiments of the present invention provide a method of sequentially loading each of said multiple overhand knots using the guiding edge to tease the two limbs of suture apart and guiding each of the two limbs of suture into the respective side slots 40A, 40B for each of the overhand knots 90, in situations where there are multiple knots and there may not be access to the free ends of the suture.

Figure 11F:
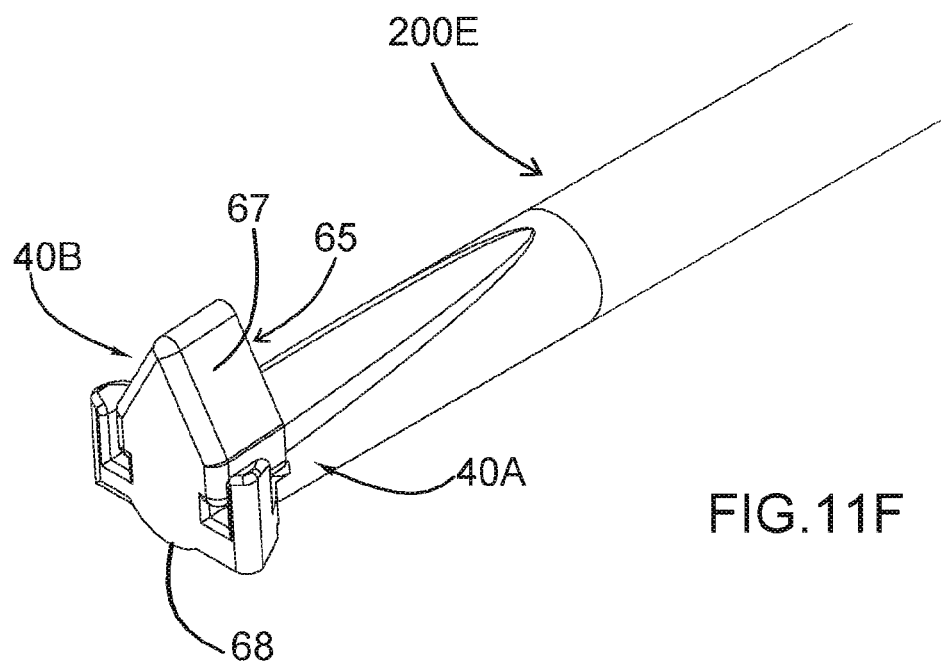
FIG. 11F, illustrates an alternate embodiment of a knot pusher, with a suture guide comprising a guiding edge, in accordance with an embodiment of the present invention.

In alternative embodiments, as shown in FIG. 11F, the guiding edge 65 may extend upwardly away from said top wall to permit loading of said two substantially parallel held limbs of suture to be loaded from above the knot pusher 200E. In the particular embodiment shown the guiding edge 65 is a tapered guiding edge 67 that extends vertically upwards away from the top wall 32 in a bottom to top direction. The method of use of the knot pusher 200E is similar to the embodiments described above, with the suture limbs being positioned above the knot pusher 200E upon loading the knot pusher 200E. The guiding edge 65 also functions in a similar manner to tease apart the two limbs of suture while they are being held parallel to one another. As shown in FIG. 11F, in some embodiments, the guiding edge 65 comprises a substantially rounded configuration defining a substantially atraumatic guiding edge to minimize damage to said two limbs of suture upon guidance into the side grooves 40A, 40B. In some such embodiment, the guiding edge 65 comprises a substantially dome shaped configuration 68 and may formed on one of the top and bottom walls 32, 34 to facilitate entry of the suture limbs into the side grooves 40A, 40B, and as such may permit loading of the suture from above or below the knot pusher 200E. The dome shaped configuration 68 may be usable with side grooves 40A, 40B that are of a configuration as shown in FIGS. 11A-11E.

Figure 12A:
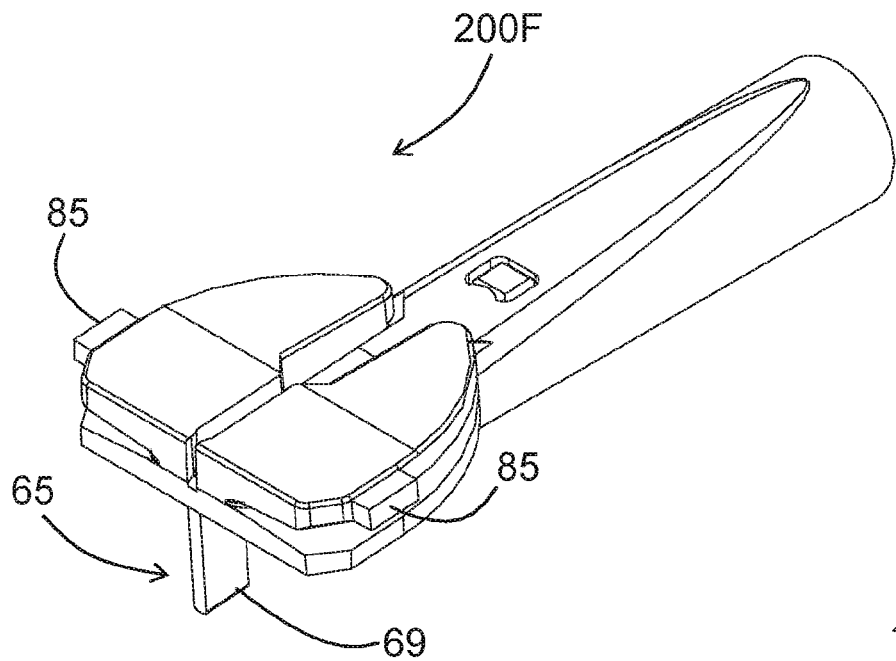
FIGS. 12A-12D, illustrate further alternate embodiments of a knot pusher comprising a suture guide in accordance with various embodiments of the present invention.
Figure 12B:
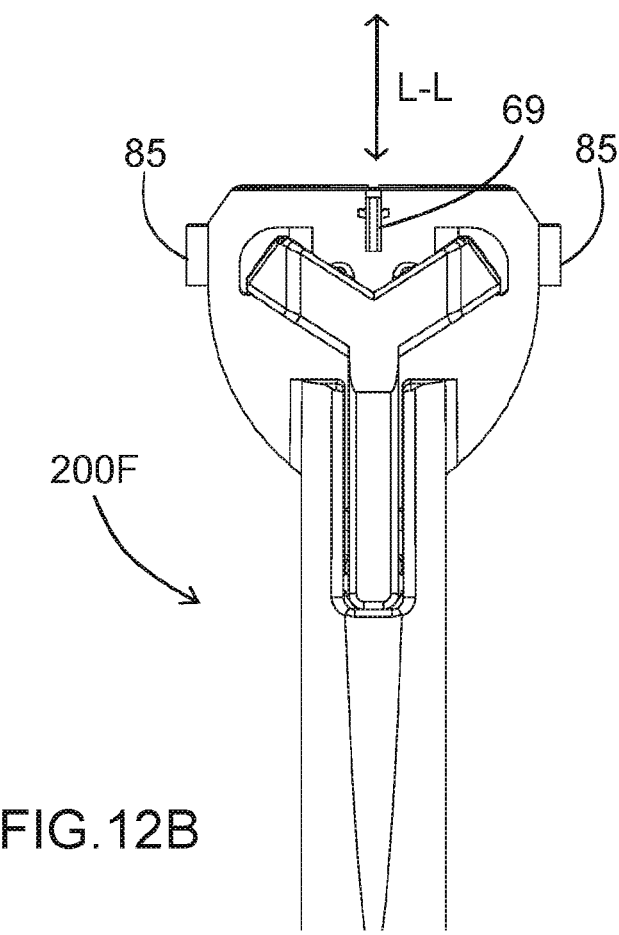
Figure 12C:
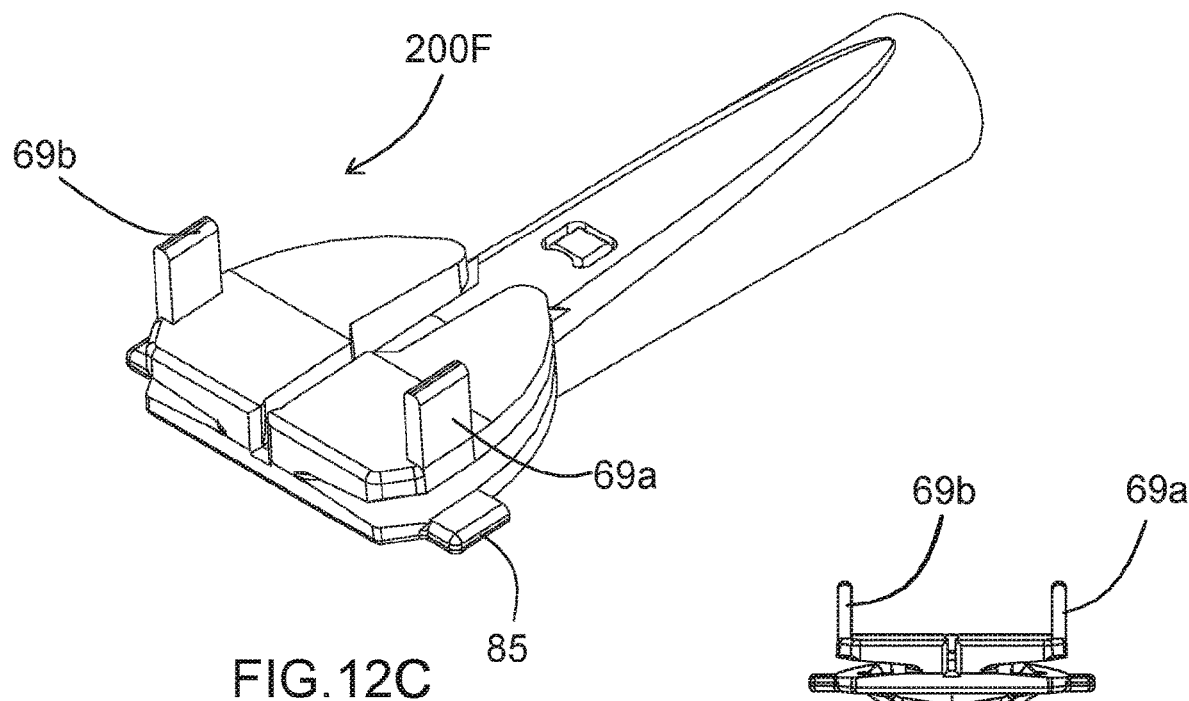
Figure 12D:
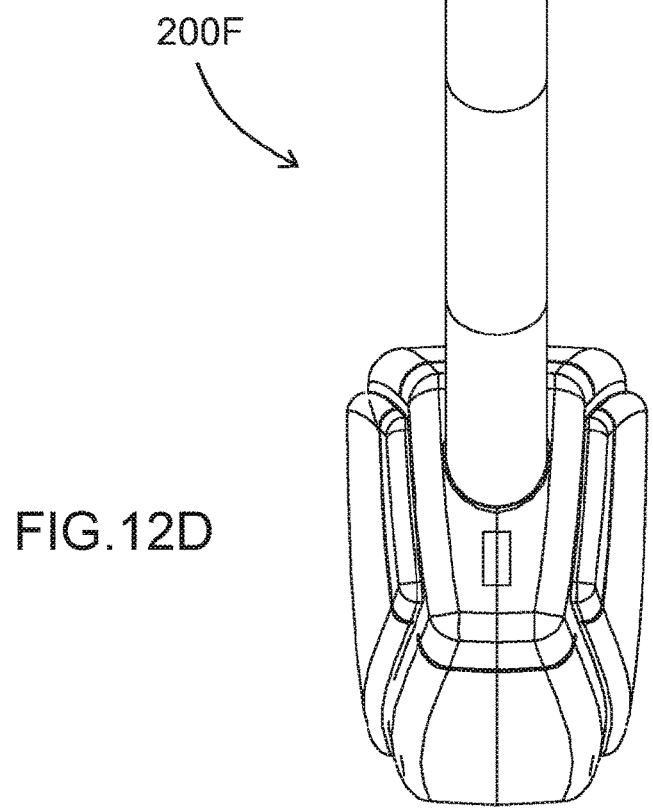

In a further alternative, as shown in FIGS. 12A-12B, a knot pusher 200F is shown where the guiding edge 65 extends substantially along the longitudinal axis L-L of the distal head 30 for teasing the two limbs of suture to maintain a separation there-between to facilitate loading thereof into the respective side grooves 40A, 40B. The guiding edge 65 extends away from the bottom wall 34 in a top to bottom direction as shown. In the illustrated embodiment, the guiding edge 65 is a substantially linear guiding edge 69 that comprises a substantially rectangular configuration. In additional embodiments as shown in FIGS. 12C-12D, the knot pusher 200F may comprise a guiding edge 65 that comprises one or more projections. In the particular example, the guiding edge comprises two upwardly extending projections 69a and 69b to help facilitate the two limbs of suture to be loaded individually into the side grooves 40A, 40B. The projections 69a, 69b provide a wall which allows the suture limb to rest against the wall to be guided into the side grooves 40A or 40B.

In alternative embodiments of the present invention, as shown in FIG. 13A, the side grooves 40A, 40B extend proximally from the knot pushing surface 38 along the distal head 30 at least partially along a top face 32' of the top wall 32 forming top facing side grooves 40A' and 40B'. More specifically, the top facing side grooves 40A' and 40B' are formed along the plane that is defined by the top most surface of the top wall 32. Alternatively, in some such embodiments, the top facing side grooves 40A' and 40B' may be formed within the distal head 30. In some such examples, the top facing side grooves 40A', 40B' are defined between said top and bottom walls 32, 34 as shown in FIG. 13A, and are each operable to receive one of the two limbs of suture during advancement of said distal head 30 to aid in pushing a knot. The top facing side grooves 40A', 40B' may provide additional visibility in loading the suture limbs within the knot pusher and as such may enhance the ease of use by providing a knot pusher that may be more intuitive to use.

Figure 13C:
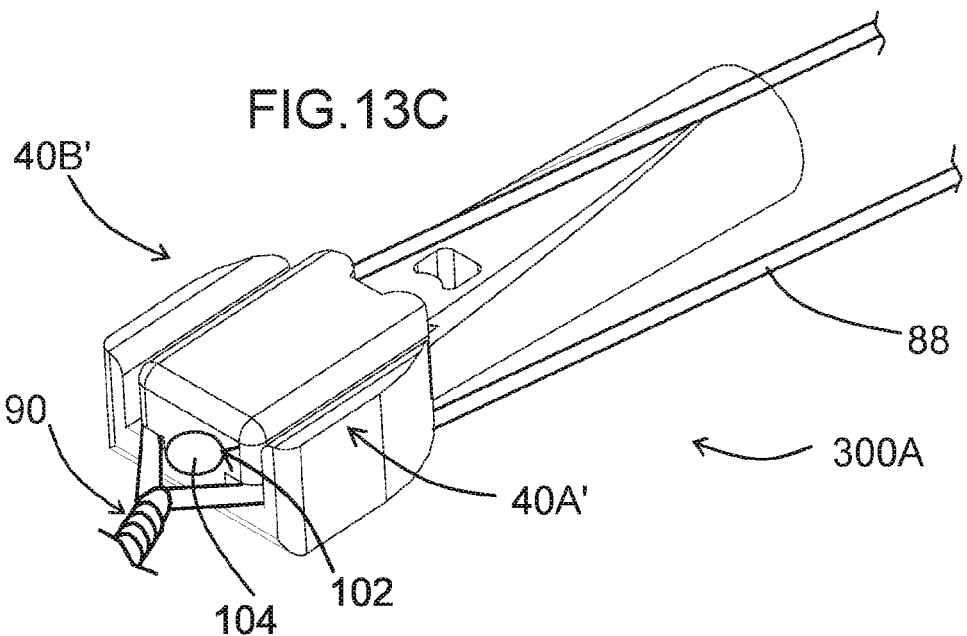
Figure 13D:
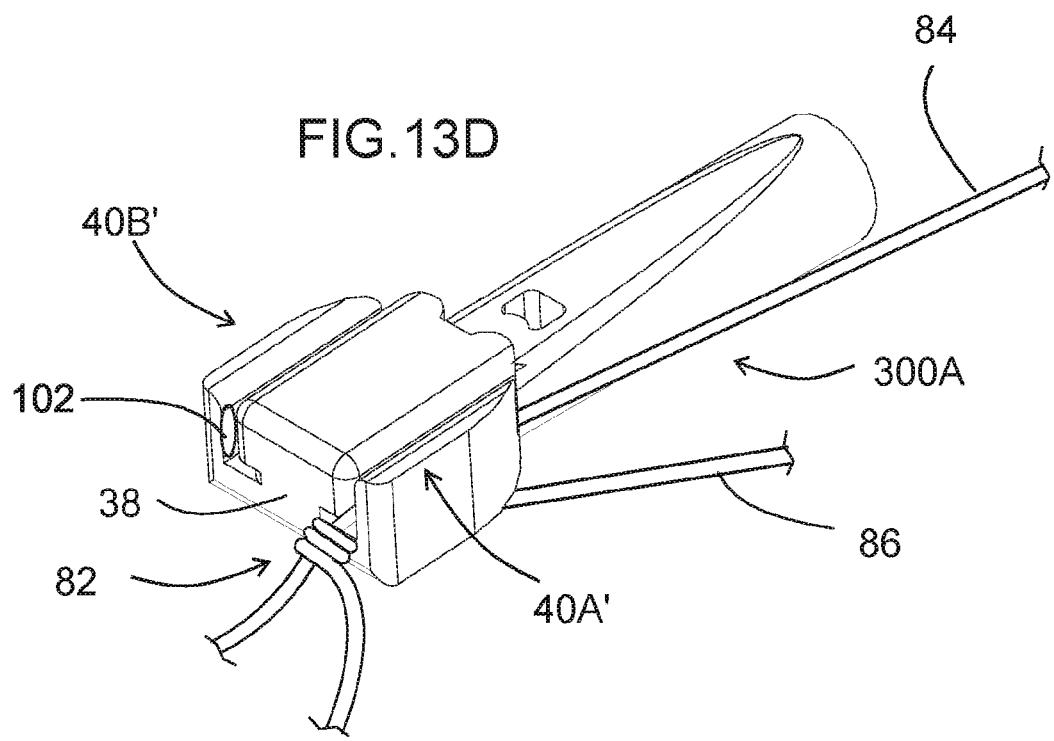

The knot pusher 300A may be usable for pushing various types of knots including sliding knots and overhand knots formed from a suture using the top facing side grooves 40A' and 40B', as will be described in further detail herein below. In some such embodiments, the knot pusher 300A is initially used to push or advance a sliding knot as shown in FIG. 13D. In some such embodiments the post 84 is passed through and held within one of the top facing side grooves 40A', 40B' such as the top facing side groove 40A' such that the sliding knot 82 being positioned against the distal knot pushing surface 38. A longitudinally directed force is applied against the sliding knot 82 by the distal knot pushing surface 38, such that it slides along the post 84 distally until it is positioned at a desired tissue site for example to approximate a defect. Thus, tension is maintained on post 84 as the knot pusher 300A is advanced. The top facing side grooves 40A', 40B' may additionally be used to push an overhand knot 90 to the tissue site for example to secure the sliding knot 82, as shown in FIG. 13C. In some such embodiments the two limbs of suture 88 exiting an overhand knot 90 are passed through the top facing side grooves 40A', 40B' respectively to aid in advancement of one or more overhand knots 90, as shown. Similar to embodiments shown and discussed herein above including embodiments shown in FIGS. 9A-12D, the side grooves 40A and 40B, such as the top facing side grooves 40A', 40B' are laterally spaced apart or are distanced from one another to enable the two suture strands to be oriented at an angle of about 180° with respect to the overhand knot 90 and with respect to one another, to permit effective tightening and locking of the overhand knot 90.

Thus, some embodiments of the present invention provide a method of using the knot pusher 300A comprising the step of advancing a sliding knot 82 using one of the top facing side grooves 40A', 40B' prior to advancing the one or more overhand knots 90, where one of the two limbs of suture is held within one of the top facing side grooves 40A', 40B' during the advancement of the sliding knot 82. The method further comprises the step of individually advancing one or more overhand knots 90 using both of the top facing side grooves 40A', 40B' where one of the two limbs of suture is held within a respective one the top facing side grooves 40A', 40B' during advancement of the one or more overhand knots 90.

Figure 13E:
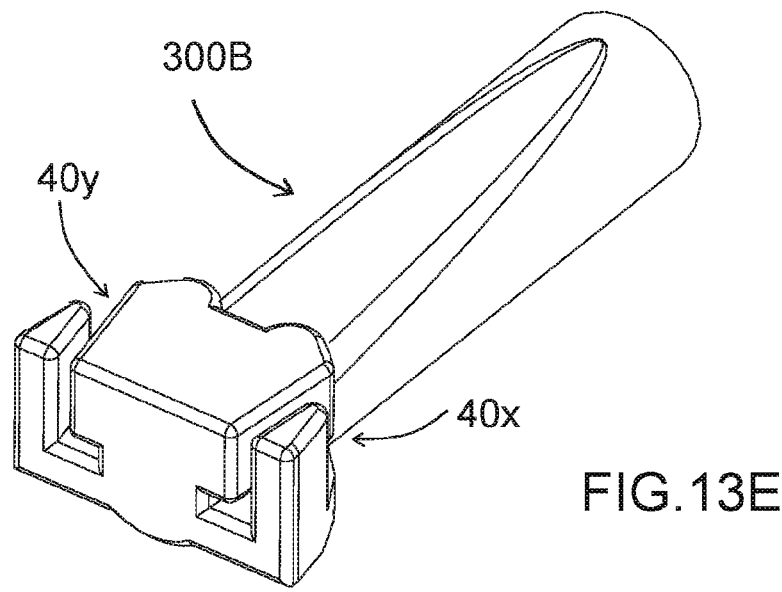
FIGS. 13E-13F, illustrate a further alternative embodiment of a knot pusher, with oblique top facing side grooves, in accordance with an embodiment of the present invention.
Figure 13F:
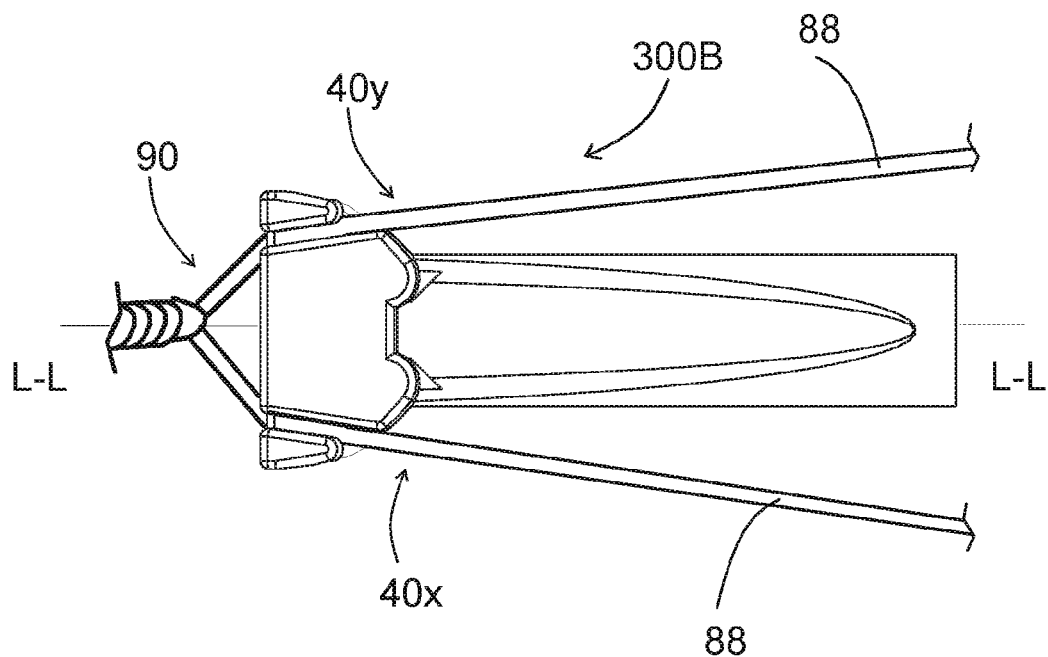

In additional embodiments, as shown in FIGS. 13E and 13F, the top facing side grooves 40A',40B' may be oriented at an angle with respect to the longitudinal axis of said knot pusher 300B forming oblique top facing side grooves 40x, 40y. In one specific example as shown, the oblique top facing side grooves 40x, 40y are oriented at an angle such that they extend away from said longitudinal axis L-L towards said proximal direction, such that the distance between the top facing side grooves 40A', 40B' is narrower adjacent said distal knot pushing surface 38 than along a proximal portion of the distal head. In other words, the oblique top facing side grooves 40x, 40y taper away from the distal knot pushing surface 38 towards the lateral edge of the distal head 30. The orientation of the oblique top facing side grooves 40x, 40y may facilitate loading of the two limbs of suture within the knot pusher 300B by allowing the suture limbs 88 to be routed along a path that provides some strain relief. As such, the oblique top facing side grooves 40x, 40y may reduce strain exerted on the suture limbs as for example an overhand knot 90 is being advanced to the desired tissue site, as illustrated in FIG. 13F. In some such embodiments the oblique top facing side grooves 40x, 40y reduce strain on the suture limbs 88 in a normal configuration in which the suture limbs are held during use, where the limbs may extend outwards in a distal to proximal direction to be held within the user's hands during manipulation of the suture and/or advancement of one or more knots. In some such embodiments, one or more of the top facing side grooves 40x, 40y may comprise at least one side groove suture retaining element to retain one of the two limbs of suture within the at least one said top facing side grooves as described previously herein above. In some such embodiments, the at least one side groove suture retaining element comprises a resilient snap arm 44 that forms a portion of one of the top and bottom walls. Furthermore, in some such embodiments, the knot pusher may further comprising a top wall suture receiving element such as intermediate groove 40C, associated with the top wall 32 for receiving one of the two limbs of the suture during advancement of the distal head 30 to facilitate advancement of a sliding knot 82.

In other embodiments, as shown in FIG. 13G, the distal head 30 may be provided with a guiding edge 65 as described earlier with reference to FIG. 11F. As shown the guiding edge 65 comprises a tapered guiding edge 67 that facilitates loading of the suture limbs into the knot pusher 300C. In the particular implementation shown, the tapered guiding edge 67 extends between the top facing side grooves 40x, 40y along the top wall 32. The tapered guiding edge 67 provides tapered edges 67' that are functional to contact the two limbs of suture exiting the overhand knot 90. The tapered edges 67' function to tease the two limbs of suture apart and guide them into the top facing side grooves 40x, 40y.

Figure 14A:
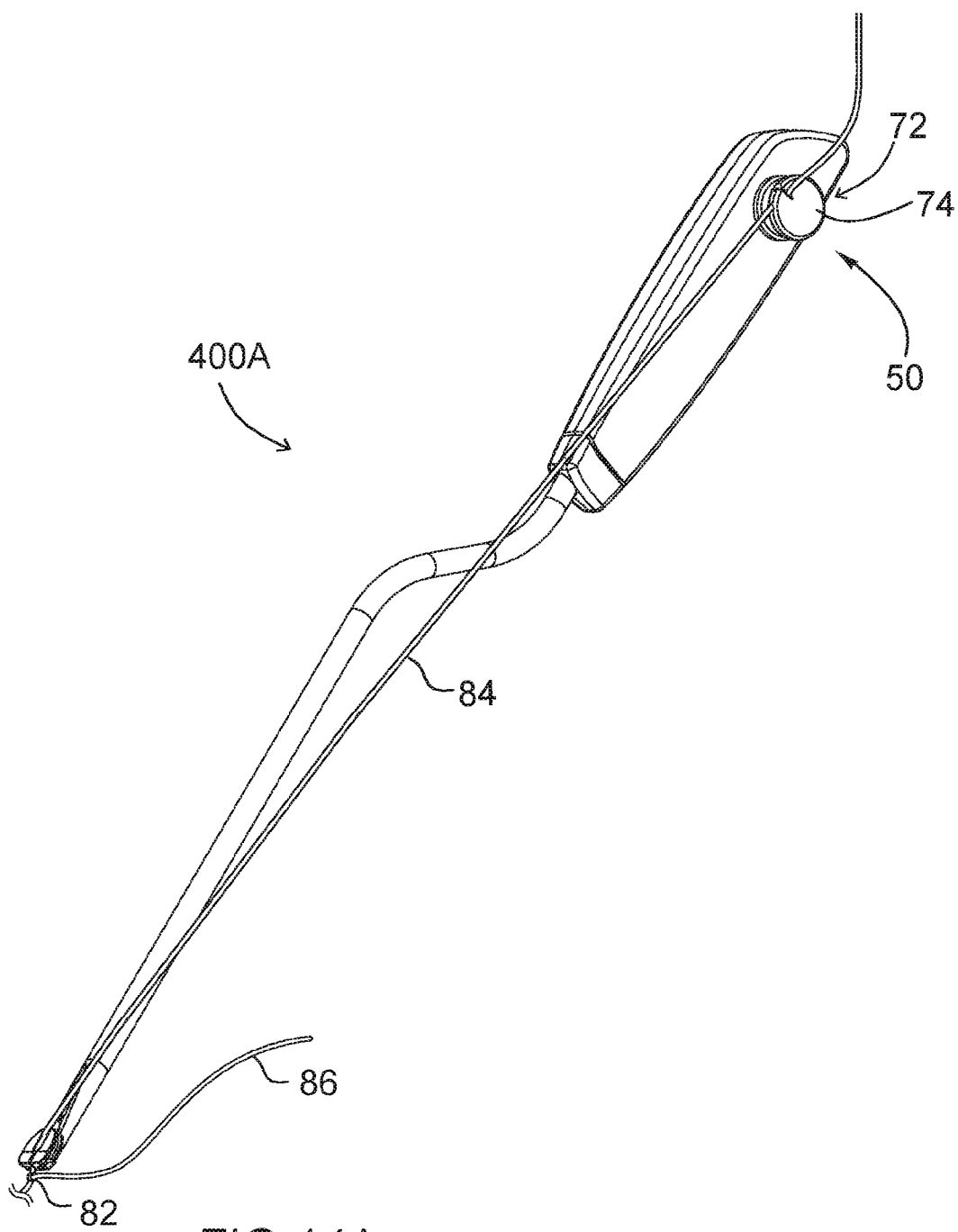
FIG. 14A-14C, illustrate a further alternative embodiment of a knot pusher, with a tensioning maintaining element, in accordance with an embodiment of the present invention.
Figure 14B:
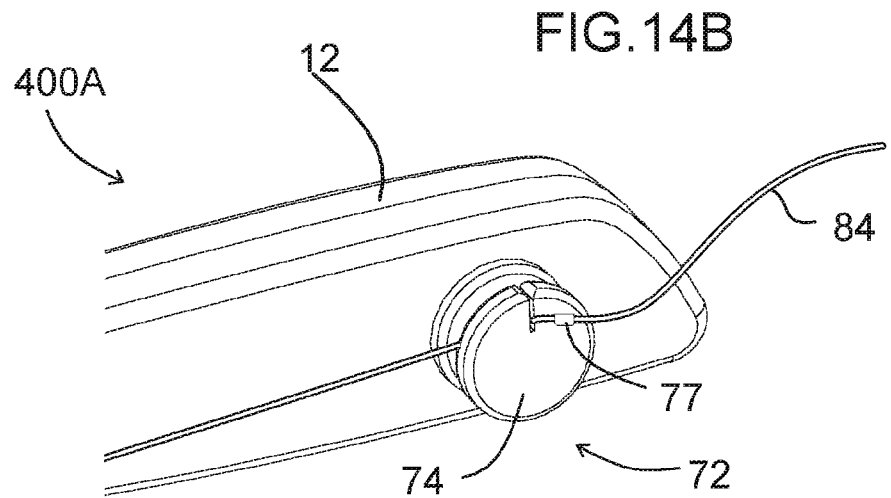
Figure 14C:
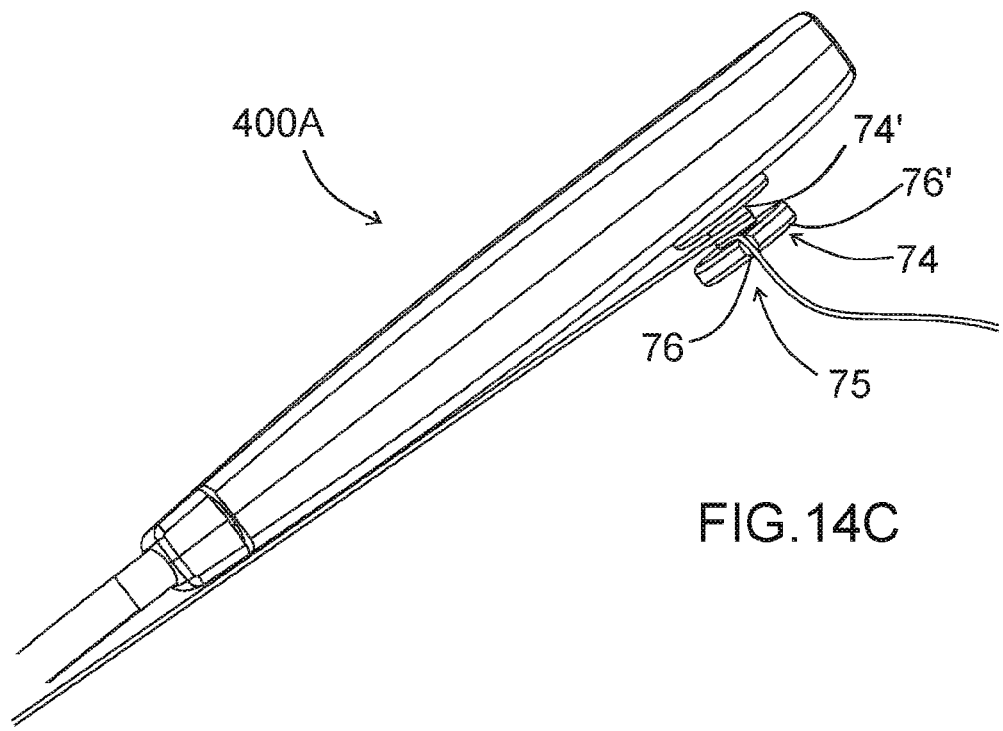

In an additional embodiment, similar to embodiments discussed previously herein above with reference to FIG. 1K, a the knot pusher 400A is provided as illustrated in FIGS. 14A and 14B, that additionally comprises a tensioning aid or tension maintaining element or tensioner 50 that is positioned, for proximal portion of the knot pusher 400A, such as along the handle 12. In other embodiments, the tensioning aid 50 may be positioned along the shaft 14 of the knot pusher 400A. In still other configurations the tensioning aid 50 may be positioned along a front or top face of the shaft 14 or handle 12. The tensioning aid 50 functions to keep tension on the strand of suture that is held within the intermediate groove 40C for example during advancement of a sliding knot. In one specific example, as shown in FIG. 14B, the tensioning aid 50 defines at least one post or peg 72 (which may alternatively be referred to as a finger 72) that is mounted on the side of the handle and extends laterally away from the surface of the handle 12. In some such embodiments, the tensioning aid 50 peg or finger 72 of the tensioning aid 50 is embodied on the shaft 14 or at a location along the device that is somewhere other than where the user needs to hold the device. The finger 72 allows one of the two suture limbs (which may comprise a post 84), to be wrapped on or around it so that it can be held in tension. In the specific example shown, the finger 72 comprises a spool 74. As shown in FIG. 14C, the strand of suture such as the post 84 may be wound about a leg 74' of the spool 74 to be held in tension. In some embodiments of the present invention the tension maintaining element or tensioning aid additionally comprises a friction element 75 for frictionally engaging said one of the two suture limbs to retain the suture limb in tension. In the specific example shown, a wall 76' of the spool that extends radially outwards from the leg 74' and provides means to frictionally engage the suture limb. The wall 76' defines a friction element in the form slot 76 for receiving a segment of the at least one limb of suture therein. More specifically, the suture limb may be held in frictional engagement within the slot 76 after it has been wound about the leg portion 74' of the spool 74. In further embodiments the friction element 75 may additionally comprise a clip 77 having a press-fit mechanism for press-fit engagement of one of the two suture limbs to allow the suture limb to be held within the slot 76 and/or against the suture spool 74 or a portion of the knot pusher 400A as shown in FIG. 14B.

The method of use of the tensioning aid 50 is described further herein below with reference to FIGS. 14A-14C that illustrate a method of using the knot pusher 400A comprising a tensioning aid 50. More specifically, when advancing a sliding knot 82 as shown, the post 84 is passed through the central groove 40C with the sliding knot 82 held against the distal knot pushing surface 38. The knot pusher 400A is then advanced till the tissue site while the post 84 is held in tension. Once the sliding knot 82 has been deployed at the tissue site the post 84 may be tightened further and may be pulled taut in order to tighten the sliding knot 82 for example to approximate tissue at a defect. As the sliding knot 82 tightens it pulls the tissue together closing the defect. A segment of the post 84 may then be wound about the tensioning aid or tension maintaining element such as the spool 74 and held in frictional engagement therewith in order to maintain the post 84 in tension. As such the tensioning aid 50 prevents the tension from being released from the post 84 and thus prevents the sliding knot 82 from sliding back along the post 84 due to force exerted by the tissue and may prevent the sliding knot 82 from loosening or unravelling. This may free up one of the hands of the user such as the physician by allowing the post 84 and the knot pusher 400A to be held in one hand while maintaining tension on the post 84, and at the same time allowing the physician to use the other hand to tension the locker 86 to lock the sliding knot 82. Thus, the tensioning aid or tension maintaining element 50 facilitates deployment and locking of a sliding knot 82 within a desired tissue location.

Figure 14D:
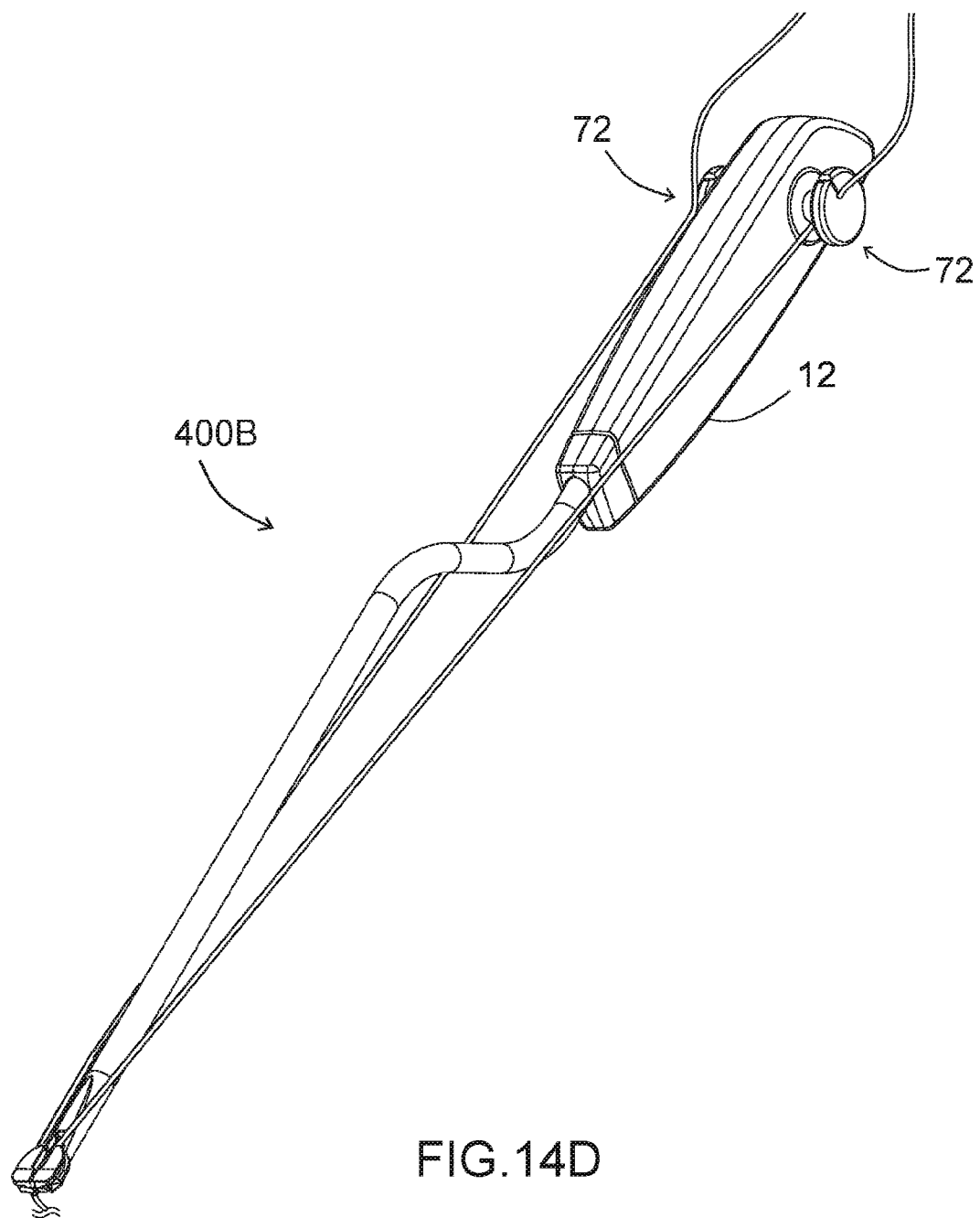

In alternative embodiments of the present invention, a knot pusher 400B is provided as shown in FIG. 14D, 14E and 14F, the knot pusher 400B comprises two tension maintaining elements or tensioners 50. In one particular example the dual tension maintaining elements or tensioners 50 comprise two fingers 72. In some such examples the two fingers comprise spools 74 that are mounted on opposing lateral sides of the handle 12 that may be used to maintain tension on one of the two limbs of suture respectively. In the particular example one of the two limbs of suture such as the post 84 may be held in tension using a preferred one of the two fingers 72 depending for example on physician preference. Alternatively, the two fingers 72 may each be used to hold a suture limb in tension respectively for example if there are more than two limbs of suture that are involved for example in a knot construct. In additional embodiments the fingers 72 may be moveable with respect the distal head 30 and may be functional to tighten an overhand knot as described further with reference to FIGS. 15A-17B.

In some such embodiments of the present invention the knot pusher additionally allows relative movement between one of the fingers 72 and the distal head 30 to exert a tensioning force on one of the limbs of suture (such as the post 84) in order to further tighten the sliding knot 82 prior to locking it. Thus, in addition to retaining the limb of suture (e.g. post 84) in tension using the fingers 72, the knot pusher additionally provides a means to exert tension on the limb of suture (e.g. post 84) in order to further tighten the sliding knot 82. Generally, a means is provided to tension a limb of suture by providing relative movement between the point at which the limb of suture is held along a portion of the knot pusher (such as the finger 72) and the sliding knot (or more specifically the surface of the knot pusher in contact with the sliding knot). Some such embodiments are described herein below where at least one finger 72 and the distal head 30 are moveable with respect to one another.

In one such example, embodiments of the present invention provide a knot pusher 500A that comprises a finger 72 that is moveable with respect to the distal head 30 to exert tension on the post 84 in order to tighten the sliding knot. In a specific implementation of this as shown in FIGS. 15A-15B, the finger 72 is moveable within a slot 73 within the handle 12. More specifically the finger 72 is moveable proximally with respect to the distal head 30, from its first position 72A to its second position 72B in order to tension the post 84 to tighten the sliding knot. Once the post 84 has been tensioned using the moveable finger 72, the locker end 86 of the suture may be pulled in order to tighten the sliding knot 82.

In another example, embodiments of the present invention provide a knot pusher 600A that comprises a finger 72 that is flexible and is moveable with respect to the distal head 30 to exert tension on the post 84 in order to tighten the sliding knot. In a specific implementation of this as shown in FIGS. 16A-16B, a flexible finger 71 is provided that extends laterally from the handle 12. The flexible finger 71 is operable to flex or pivot in the proximal direction from a first position 71A to a second position 71B to tension the post 84 to tighten a sliding knot. As such the flexible finger 71 is moveable in the proximal direction with respect to the distal head 30 in order to tension the post. Once the post 84 has been tensioned using the moveable flexible finger 71, the locker end 86 of the suture may be pulled in order to tighten the sliding knot 82. This may help facilitate tightening of the sliding knot as much as it can be tightened, prior to locking the sliding knot.

In an additional embodiment of the present invention, a knot pusher 700A is provided that comprises a distal head 30 that is moveable with respect to the finger 72 to exert tension on the post 84 in order to tighten the sliding knot. In a specific implementation of this, as shown in FIGS. 17A-17B, a tension maintaining means is providing where the distal head 30 is moveable distally with respect to the handle 12. More specifically the knot pusher comprises a plunger 79 that is coupled to the distal head via the shaft 14. The plunger 79 is moveable distally from a first position 79A to a second position 79B creating a corresponding movement in the distal head 30, which is also moveable distally, from its first position 30A to its second position 30B to tension the post 84 in order to tighten the sliding knot 82. Once the post 84 has been tensioned using the moveable head 30, the locker end 86 of the suture may be pulled in order to tighten the sliding knot 82.

In some embodiments, the knot pusher 500A as discussed in FIGS. 15A-15B may comprise two laterally opposed fingers 72 (similar to embodiments shown in 14D, 14E and 14F) for securing the two limbs of suture at a position along each of the laterally opposed fingers 72 to maintain the two limbs of suture in tension. Each of the two laterally opposed fingers 72 are moveable proximally within a slot 73 to enable proximal movement of the position or location at which the limbs of suture are secured, to enable the tensioning force to be exerted on each of the two limbs of suture to facilitate tightening of an overhand knot. The knot pusher 400B described previously herein may also comprise moveable fingers and may also function in a similar manner. In alternative embodiments the knot pusher 600A as shown in FIGS. 16A-16B may comprises two laterally opposed fingers 72 for securing the two limbs of suture at a position along each of the laterally opposed fingers 72 to maintain the two limbs of suture in tension. The two laterally opposed fingers 72 are flexible and are pivotable proximally to enable proximal movement of the position or location at which the limbs of suture are secured, to enable the tensioning force to be exerted on each of said two limbs of suture to facilitate tightening of an overhand knot. Furthermore, the knot pusher 700A, as discussed with reference to FIGS. 17A-17B, may also comprise two laterally opposed fingers and an overhand knot may be positioned adjacent the distal knot pushing surface 38 of the distal head 30 with the suture limbs exiting the overhand knot being coupled to the fingers. The distal head 30 is moveable distally upon actuation of the plunger 79 to relative movement between the distal head 30 and the position or location at which the limbs of suture are secured, to enable the tensioning force to be exerted on each of the two limbs of suture to facilitate tightening of an overhand knot. Thus, tensioning means described herein in FIGS. 14A-17B are usable to assist in advancement of one or both of sliding and overhand knots.

With reference again to FIGS. 14A-17B, the embodiments described herein provide relative movement between a finger 72 and the distal head 30 and as such provides a means to tension one of the limbs of suture to tighten a knot. Such embodiments, provide the additional advantage of providing a greater force than that can generally be applied by hand, in order to tighten the sliding knot. In some examples, the tensioning force exerted on the suture with reference to FIGS. 14A-17B, may be between about 20 Newton to about 30 Newton. In some such examples the suture is a 2-0 suture that is a force fiber comprising ultra high molecular weight polyethylene. Furthermore, in some such examples the knot pusher may additionally comprises a force limiter to limit the amount of tensioning force applied by said knot pusher. In the embodiments described herein above with reference to FIGS. 14A-17B, the tensioning force is lower than a breaking force of the suture.

Thus some embodiments of the present invention provide a knot pusher that is usable for pushing various types of knots including sliding knots and overhand knots formed from a suture, two limbs of the suture extending from the knots, the knot pusher comprising: a distal head defining top and bottom walls terminating in a distal knot pushing surface, the distal head defining a longitudinal axis; side grooves defined between the top and bottom walls, the side grooves extending proximally from said knot pushing surface along said distal head, each operable to receive one of the two limbs of suture during advancement of said distal head to aid in pushing said overhand knot; and top wall suture receiving element associated with said top wall for receiving one of the two limbs of the suture during advancement of said distal head to facilitate advancement of said sliding knot; and a tension maintaining element or tensioner associated with said knot pusher for frictionally engaging one of the two limbs of suture along a portion of said knot pusher to enable said one of said two limbs of suture to be held in tension during use.

In still additional embodiments of the present invention, a knot pusher is provided that is usable for pushing various types of knots formed from a suture including overhand knots and sliding knots, where a knot measurement or tracking means is associated with the knot pusher to enable tracking of the number of knots advanced with said knot pusher during use.

Similar to embodiments described previously the knot pusher comprises one or more grooves defined by said top and bottom walls, said grooves extending proximally from said knot pushing surface each operable to receive one of the two limbs of suture during advancement of said distal head to aid in pushing the knot. The grooves may comprise one or more of side grooves 40A, 40B to facilitate advancement of an overhand knot and intermediate grove 40C to facilitate advancement of a sliding knot. In some such embodiments the knot measurement or tracking means comprises a pressure sensor. In a particular example, as shown in FIG. 13C, a knot tracking or measurement means or component 102 is provided that comprises a pressure sensor 104 that is mounted on the distal knot pushing surface 38. Alternatively the knot measurement or tracking means 102 may be associated with one of the side grooves 40A, 40B, as shown in FIG. 13D. In some such embodiments, the knot tracking means 102 may be used to track the number of overhand knots that are advanced with the knot pusher. For example, this may held the physician to keep count of the number of overhand knot that have been advanced within the procedure. Alternatively the knot tracking means 102 may also be used to track other knots such as sliding knots. In one such example, the knot pusher additionally comprises a side groove suture retaining element (such as snaps 46a, 46b) for retaining a limb of the suture within one of the side grooves 40A, 40B, and the knot measurement or tracking means is associated with the side groove suture retaining element, in order to determine the number times the suture limb is inserted within one of the side grooves 40A, 40B. In still a further example of this the side groove suture retaining element comprises a resilient snap arm 44, where the snap arm 44 forms a portion of one of the top and bottom walls 32, 34. As shown in FIG. 9B, in a specific example of this, the knot measurement or tracking means 102 comprises a pressure sensor 104 that mounted on the resilient snap arm 44 In another alternative the knot measurement or tracking means 102 is associated with a top wall suture receiving element such as the intermediate groove 40C, as shown, and may comprise any of the variations of the knot tracking means as described herein above with respect to the side grooves 40A, 40B.

Thus, as described hereinabove, various embodiments of a knot pusher, and methods of use thereof, are disclosed. In some such embodiments the knot pusher is usable for pushing a knot formed from a suture, two limbs of the suture extending from the knot. The knot pusher comprises a distal head defining top and bottom walls terminating in a distal knot pushing surface. The distal head includes at least two side grooves defined between the top and bottom walls that extend proximally from the knot pushing surface. Each of these side grooves is operable to receive one of the limbs of suture. The distal head additionally comprises at least one suture guide coupled to the top and bottom walls for guiding the one of the limbs of suture into one of the side grooves The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A knot pusher usable for pushing a knot formed from a suture, two limbs of the suture extending from the knot, the knot pusher comprising:
    a distal head defining top and bottom walls terminating in a distal knot pushing surface;
    at least two side grooves defined between said top and bottom walls and extending proximally from said distal knot pushing surface, each of said at least two side grooves operable to receive one of the limbs of the suture; and
    at least one suture guide coupled to said top and bottom walls for guiding one of the limbs of the suture into one of the at least two side grooves;
    wherein the knot pusher comprises at least one side groove suture retaining element for retaining the one of the limbs of the suture within said one of said at least two side grooves, wherein the at least one side groove suture retaining element is positioned within at least one of the at least two side grooves, wherein the at least one suture guide guides said one of the limbs of the suture to said at least one side groove suture retaining element;
    wherein said at least one suture guide comprises a suture containment element that defines a barrier for co-operating with the at least one side groove suture retaining element to retain said one of the limbs of the suture within said one of the at least two side grooves;
    wherein the suture containment element defines a cavity on an internal surface of one of said top and bottom walls, wherein the at least one side groove suture retaining element is receivable within the cavity forming said barrier to encompass the at least one side groove suture retaining element therein.

2. The knot pusher of claim 1, wherein the knot pusher further comprises a top wall suture receiving element associated with said top wall for receiving one of the two limbs of the suture during advancement of said distal head to facilitate advancement of a sliding knot.

3. The knot pusher of claim 2, further comprising a tension maintaining element associated with said knot pusher for frictionally engaging one of the limbs of the suture along a portion of said knot pusher to enable said one of the limbs of the suture to be held in tension after advancement of said sliding knot.

4. The knot pusher of claim 1, wherein the at least one suture guide defines a guiding channel that is in communication with the one of the at least two side grooves for guiding the one of the limbs of suture into said one of the at least two side grooves to facilitate insertion of said one of the limbs of suture therein.

5. The knot pusher of claim 4, wherein the at least one suture guide comprises a pair of flanges that extend at an angle from said top and bottom walls, wherein said pair of flanges define said guiding channel.

6. The knot pusher of claim 1, wherein said suture containment element comprises an extending portion of one of said top and bottom walls that extends about the at least one side groove suture retaining element forming the barrier to encompass the at least one side groove suture retaining element therein to prevent said one of the limbs of suture received within said one of the at least two side grooves from being removed therefrom.

7. The knot pusher of claim 6, wherein the at least one side groove suture retaining element comprises a resilient material that grips the suture in order to retain said one of the limbs of the suture within said one of the at least two side grooves.

8. The knot pusher of claim 6, wherein the at least one side groove suture retaining element comprises a resilient snap arm, said snap arm forming a portion of one of said top and bottom walls.

9. The knot pusher of claim 8, wherein said snap arm is receivable within the cavity.

10. The knot pusher of claim 9, wherein the snap arm forms a portion of said bottom wall, wherein said at least one suture guide comprises an extending portion of said bottom wall.

11. The knot pusher of claim 1, wherein said at least one suture guide comprises a guiding edge that extends away from said distal head along a plane that is perpendicular to said distal head to maintain a separation between the two limbs of the suture to enable loading of said two limbs of the suture into the at least two side grooves while said two limbs of the suture are held substantially parallel to one another during use.

12. The knot pusher of claim 1, further comprising a knot tracking member associated with said knot pusher to enable tracking of a number of overhand knots advanced by said knot pusher.

13. The knot pusher of claim 1, wherein the at least one side groove suture retaining element is positioned on one of said top or bottom walls.

14. The knot pusher of claim 1, wherein the distal knot pushing surface is planar.

15. The knot pusher of claim 1, wherein the at least one side groove suture retaining element allows said one of the limbs of suture to enter into the one of the at least two side grooves upon force exerted by the suture.

* * * * *